(12) United States Patent
Blum

(10) Patent No.: US 6,955,873 B1
(45) Date of Patent: *Oct. 18, 2005

(54) DIAGNOSIS AND TREATMENT SYSTEM FOR REWARD DEFICIENCY SYNDROME (RDS) AND RELATED BEHAVIORS

(76) Inventor: Kenneth Blum, 1211 Lost Stone, San Antonio, TX (US) 78258

( * ) Notice: Subject to any disclaimer, the term of this patent is extended or adjusted under 35 U.S.C. 154(b) by 470 days.

This patent is subject to a terminal disclaimer.

(21) Appl. No.: 09/632,838

(22) Filed: Aug. 4, 2000

Related U.S. Application Data
(60) Provisional application No. 60/147,229, filed on Aug. 4, 1999.

(51) Int. Cl.$^7$ .................... C12Q 1/68; A61K 39/385; A61K 31/555; A01N 37/42
(52) U.S. Cl. .................... 435/6; 424/195.1; 514/188; 514/561
(58) Field of Search .................... 435/6; 424/195.11; 514/188, 561

(56) References Cited

U.S. PATENT DOCUMENTS 5,919,638 A  *  7/1999  Russell et al. ............. 435/7.23
6,132,724 A  *  10/2000  Blum ....................... 424/195.1

FOREIGN PATENT DOCUMENTS

WO          9848785      *  11/1998

* cited by examiner

*Primary Examiner*—Kenneth R. Horlick
*Assistant Examiner*—Joyce Tung

(57) ABSTRACT

The present invention relates to a kit and an intervenously administrable preparation, both, with a signal transmitter precursor, an enhancer of precursor uptake, and an inhibitor of neurotransmitter reuptake or signal transmitter catabolism. The kit also contains an appropriate swab for obtaining oral cells suitable for allelic analysis. The intervenous formulation contains similar materials and, in some cases, ethanol. Either the kit composition or the intervenous formulation may be used as guided by a subjects allelic analysis. Collections of particular alleles, especially those relating to neural system are comprehensible in terms of likelihood of success in the administration of an interveinous formulation or ingestion of components of the subject kit.

33 Claims, No Drawings

DIAGNOSIS AND TREATMENT SYSTEM FOR REWARD DEFICIENCY SYNDROME (RDS) AND RELATED BEHAVIORS

BACKGROUND OF THE INVENTION

This application claims benefit of 60/147,229 filed Aug. 4, 1999

The following pending applications are hereby incorporated by reference: 09/481,426 and 09/069,886 and 09/356,266 and 09/423,040 and PCT US 98/08684.

SynerGene NutraLife Essentials, which is a division of CyberPharm Corporation, is a new line of patent protected nutraceuticals and neutraceuticals. All products in the SynerGene line provide high quality nutrients consisting of amino acids, trace minerals, vitamins, minerals, and herbals. When combined into numerous blends they have demonstrable therapeutic health benefits. The uniqueness of this particular line is that each product is specifically formulated to achieve synergistic activity from the active ingredient which has been shown by specific studies as well as functional combinations which have not been previously available. The products are backed up by double blind, placebo, controlled open label research studies on humans as well as other rigorous studies (including both human and animal studies) and extensive anecdotal reports.

Another aspect contributing to the uniqueness of the SynerGene products is the fact that the origin of action of all the products is in the central nervous system. Some of the products ultimately affect the peripheral nervous system and some of them ultimately affect the central nervous system. However, all are formulated to affect the health of the central and peripheral nervous system.

The Reward Deficiency Syndrome (RDS) results from a dysfunction in the Brain Reward Cascade which directly links abnormal craving behavior with a deficit in the DRD2 Dopamine Receptor Gene. Dopamine is a very powerful neurotransmitter in the brain which controls feelings of well being. This sense of well being is produced through the interaction of dopamine and neurotransmitters such as serotonin, the opioids, and other powerful brain chemicals. Low serotonin levels are associated with depression. High levels of the opioids (the brain's opium) are associated with a sense of well being. The complex interactions of these powerful neurotransmitters ultimately regulating the Dopaminergic Activity in the Reward Center of the Brain has been termed "The Brain Reward Cascade".

In individuals possessing an abnormality in the DRD2 Dopamine Receptor Gene, the brain lacks enough Dopamine receptor sites to use the normal amount of Dopamine in the Reward Center of the brain and thus reduces the amount of Dopamine produced in this area of the brain. In individuals not possessing the variant in the Dopamine Receptor Gene who lived certain lifestyles (heavy cocaine abuse, extremely low caloric diet, high levels of stress over an extend ed period of time, etc.) their brains function as if the persons have the DRD2 genetic variant.

Nutraceuticals are nutritional supplements which have been shown to affect the peripheral by nervous system or other systems of the body. These include products for symptoms such as pain, inflammation, cardiovascular disorders, immune system responses, etc. Neutraceuticals are also nutritional supplements which have been shown to affect the central nervous system of the body. These products are for disorders such as addictions to alcohol, cocaine, nicotine, carbohydrates, sex, gambling, etc. and disorders such as attention deficit hyperactivity disorder, Tourette Disorder, personality disorders, depression, premenstrual syndrome, premenstrual dysphoria disorder, etc.

The overall effect is inadequate Dopaminergic Activity in the Reward Center of the Brain. This defect drives individuals to engage in activities which will increase brain Dopamine function. Consuming large quantities of alcohol or carbohydrates (carbohydrate binging) stimulate the brain's production of and utilization of Dopamine. So too does the intake of crack/cocaine and the abuse of nicotine. Also, it has been found that the genetic abnormality is associated with aggressive behavior which also stimulates the brain's use of Dopamine.

The Reward Deficiency Syndrome involves a form of sensory deprivation of the brain's reward or pleasure mechanisms. The Reward Deficiency Syndrome can be manifested in relatively mild or severe forms that follow as a consequence of an individual's biochemical inability to derive reward from ordinary, everyday activities. We believe that we have discovered at least one genetic aberration that leads to an alteration in the reward pathways of the brain. It is a variant form of the gene for the dopamine D2 receptor, called the A1 allele. This genetic variant also is associated with a spectrum of impulsive, compulsive, and addictive behaviors. The concept of the Reward Deficiency Syndrome unites those disorders and may explain how simple genetic anomalies give rise to complex aberrant behavior.

The Biology of Reward

The pleasure and reward system in the brain was discovered by accident in 1954. The American psychologist James Olds was studying the rat brain's alerting process, when he mistakenly placed the electrodes in a part of the limbic system, a group of structures deep within the brain that are generally believed to play a role in emotions (Olds, 1995). When the brain was wired so that the animal could stimulate this area by pressing a level, Olds found that the rats would press the lever almost nonstop, as much as 5,000 times an hour. The animals would stimulate themselves to the exclusion of everything else except sleep. They would even endure tremendous pain and hardship for an opportunity to press the lever. Olds had clearly found an area in the limbic system that provided a powerful reward for these animals. Research on human subjects revealed that the electrical stimulation of some areas of the brain (medial hypothalamus, which is in the limbic system) produced a feeling of quasi-orgasmic sexual arousal. If certain other areas of the brain were stimulated, an individual experienced a type of light-headedness that banished negative thoughts. These discoveries demonstrated that pleasure is a distinct neurological function that is linked to a complex reward and reinforcement system (Hall, eta!. 1977).

During the past several decades research has been able to establish some of the brain regions and neurotransmitters involved in reward. A neuronal circuit deep in the brain involving the limbic system and two regions called the nucleus accumbens and the *globus pallidus* appears to be critical in the expression of reward for people (Wise and Bozarth, 1984). Although each substance of abuse (listed above) and each activity of abuse (listed above) appears to act on different parts of this circuit, the end result is the same.

Dopamine is released in the nucleus accumbens and the hippocampus (Koob and Bloom, 1988). Dopamine appears to be the primary neurotransmitter of reward at the reinforcement sites. It is useful to think of the brain's reward system as a cascade in which one reaction triggers another. At the level of individual neurons, the Brain Reward Cascade (Blum and Kozlowski, 1990) is catalyzed by a number of neurotransmitters. Each neurotransmitter binds to certain types of receptors and serves a specific function. The binding of the neurotransmitter to a receptor on a neuron triggers a reaction that is part of the cascade. Disruption of these intercellular cascades results in one form or another of the Reward Deficiency Syndrome.

The Cascade Theory of Reward

During the past decades, considerable attention has been devoted to the investigation of the neurochemical and neuroanatomical systems that underlie a variety of substance seeking behaviors. In a normal person, neurotransmitters (the messengers of the brain) work together in a pattern of stimulation or inhibition, the effects spreading downward from complex stimuli to complex patterns of response like a cascade, leading to feelings of well being, which is the ultimate reward (Cascade Theory of Reward) (Cloninger, 1983; Stein and Belluzzi, 1986; Blum and Koslowski, 1990).

In the reward areas, the following interactions take place (Stein and Belluzzi, 1986; Blum, 1989):

1. serotonin in the hypothalamus indirectly activates opiate receptors and causes a release of enkephalins in the ventral tegmental region A~The enkephal ins inhibit the firing of GABA which originates in the substantia nigra A~region;
2. GABA/Es normal role, acting through GABA B receptors, is to inhibit and control the amount of dopamine released at the ventral tegmental regions for action at the nucleus accumbens. When the dopamine is released in the nucleus accumbens it activates dopamine D 2 receptors, a key reward site. This release is also regulated by enkephalins acting through GABA. The supply of enkephalin s is controlled by the amount of the neuropeptidases which destroy them.
3. dopamine may also be released into the amygdala. From the amygdala, dopamine reaches the hippocampus and the CA, cluster cells stimulates dopamine D 2 receptors, another reward site.
4. an alternate pathway involves norepinephrinein the locus of ceruleus whose fibers project into the hippocampus at a reward area centering around cluster cells which have not been precisely identified, but which have been designated a CAx. When GABA A receptors in the hippocampus are stimulated, they cause the release of norepinephrine at the CAx site.

It is to be noted that the glucose receptor (GR) in the hypothalamus is intricately involved and "links" the serotonergic system with opioid peptides leading to the ultimate release of dopamine at the n. accumbens.

In the Brain Reward Cascade (Blum and Kozlowski, 1990), these interactions may be viewed as activities of subsystems of a larger system, taking place simultaneously or in sequence, merging in cascade fashion toward anxiety, anger, low self-esteem, or other bad feelings or toward craving or a substance that will make these bad feelings go away, for example alcohol, carbohydrates, etc. Genetic anomalies, long-term continuing stress, or long-term abuse of substances can lead to a self-sustaining pattern of abnormal craving behavior in both animals and humans. Animal model support for the cascade theory can be derived from a series of experiments carried out by T. K. Li et. al., (Russell, Lanin, and Taljaard, 1988; McBride, 1990; Zhou, 1990; McBride, et. al. 1993) upon their alcohol-preferring (P) and non-preferring (NP) rat lines. They found that the P rats have the following neurochemical profile:

1. lower serotonin neurons in the hypothalamus;
2. higher levels of enkephalin in the hypothalamus (due to a lower release);
3. more GABA neurons in the nucleus accumbens;
4. reduced dopamine supply at the nucleus accumbens;
5. reduced densities of dopamine D 2 receptors in the meso-limbic areas.

This suggests a four-part cascade sequence leading to a reduction of net dopamine release in a key reward area. This was further confirmed when they found that by administering substances that increase the serotonin supply at the synapse, or by stimulating dopamine D 2 receptors directly, they could reduce craving for alcohol (McBride et al. 1994). Specifically, D2 receptor agonists reduce alcohol intake in high alcohol preferring rats whereas D2 dopamine receptors antagonists increase alcohol drinking in these inbred animal s (Dyr, et al. 1993). Human support for the Brain Reward Cascade also can be derived from a series of clinical trials with neuronutrients (precursor amino acid loading technique and enkephalinase inhibition) indicating reduced craving, reduced stress rates, facilitated recovery and reduced relapse rates (Brown et al. 1990; *Blum and Tractenberg,* 1988; Blum et al. 1989).

Most recently, the notion of dopamine as the final common pathways for a number of diverse drugs of abuse such as cocaine, morphine, and alcohol is supported by Ortiz and associates at Yale University School of Medicine and University of Connecticut Health Services Center demonstrating that chronic treatment of either cocaine, morphine, or alcohol similarly results in several biochemical adaptations in the meso-limbic dopamine system, which may underlie prominent changes in the structural and functional properties of the neuronal pathways related to the above (Also see Routtenberg, DiChiara, and Inperato, 1988). We propose that the Reward Deficiency Syndrome gives rise to a wide range of disorders that can be classified as impulsive-addictive-compulsive disorders. Impulsive disorders include attention deficit hyperactivity disorder and Tourette's Disorder. Addictive disorders include substance-seeking behaviors involving alcohol, drugs, nicotine, and food. Compulsive diseases include pathological gambling and excessive sexual activity.

CyberPharm, Incorporated through an intellectual property license from 1899 LLC controls the following related art with the specified limitations:

Anti-Inflammatory, Analgesics

1. U.S. Pat. No. 39,452, issued Mar. 27, 1984, entitled CLASS OF ANALGESICS AND/OR ANTI-INFLAMMATORY AGENTS CONSISTING OF INHIBITORS OF BREAKDOWN OF ENDOGENOUS ENKEPHALIN AND/OR ENDORPHIN, AND COMBINATIONS OF SAID ANALGESICS WITH ANTIPYRETIC, ANTI-INFLAMMATORY (ASPIRIN-TYPE) DRUGS refers to a new class of analgesics provided by substances that inhibit breakdown of endogenous substance such as enkephalins and/or endorphins. The analgesic effect of an enkephalin breakdown inhibitor is greatly enhanced by being combined with an antipyretic, anti-inflammatory analgesic, herein designated as an aspirin-type drug. Specifically, both D-phenylalanine and D-leucine, each an enkephalin breakdown inhibitor, when used separately provides excellent analgesia in animals and man without developing tolerance or addiction in either species. Use of a combination of D-phenylalanine and D-leucine provides a greatly enhanced analgesia approaching the analgesia achieved by morphine. Analgesia by the latter combination is very long-lasting in animals. The injection of a combination of D-phenylalanine and an aspirin-like drug that is antipyretic and anti-inflammatory in an animal provides a greatly enhanced analgesia approaching the analgesia achieved by morphine. Analgesia by D-phenylalanine is very long-lasting in humans. D-phenylalanine also exhibits anti-inflammatory character, as demonstrated in animal tests.

2. U.S. Pat. No. 4,579,843, issued Apr. 1, 1986, entitled ANALGESIC AND ANTI-INFLAMMATORY COMPOSITIONS, describes analgesic and anti-inflammatory compositions which comprise a therapeutically effective amount of a first agent selected from the group consisting of D-phenylalanine, DL-phenylalanine, D-leucine, and DL-leucine and synergistically effective amount of a second therapeutic agent selected from the group consisting of aspirin and an aspirin-type non-steroidal anti-inflammatory, anti-pyretic agent.

3. U.S. Pat. No. 4,687,781, issued Aug. 18, 1987, entitled ANALGESIC AND ANTI-INFLAMMATORY COMPOSITIONS, describes analgesic and anti-inflammatory compositions are provided which comprise a therapeutically effective amount of a hydrocinnamic acid alone, or in combination with one or more amino acids selected from the group consisting of D-phenylalanine, DL-phenylalanine, D-leucine, and DL-leucine and synergistically effective amount of a second therapeutic agent selected from the group consisting of aspirin and an aspirin type non-steroidal anti-inflammatory, anti-pyretic agent.

4. U.S. Pat. No. 4,730,007, issued Mar. 8, 1988, entitled NOVEL ANALGESIC COMPOSITIONS describes an analgesic composition comprising an effective amount of an analgesic, anti-inflammatory agent selected from the group consisting of D-phenylalanine, DL-phenylalanine, D-leucine, DL-leucine and hydrocinnamic acid and a synergistically effective amount of acetaminophen is provided by the present invention.

5. A Canadian application entitled CLASS OF ANALGESICS AND/OR ANTI-INFLAMMATORY A GENTS CONSISTING OF INHIBITORS OF BREAKDOWN OF ENDOGENOUS ENKEPHALIN AND/OR ENDORPHIN, AND COMBINATION S OF SAID ANALGESICS WITH ANTIPYRETIC, ANTI-INFLAMMATORY (ASPIRIN-TYPE) DRUGS describes a new class of analgesics provided by substances that inhibit breakdown of endogenous substance such as enkephalins and/or endorphins. The analgesic effect of an enkephalin breakdown inhibitor is greatly enhanced by being combined with an antipyretic, anti-inflammatory analgesic, herein designate d as an aspirin-type drug. Specifically, both D-phenylalanine and D-leucine, each an enkephalin breakdown inhibitor, when used separately provides excellent analgesia in animals and man without developing tolerance or addiction in either species. Use of a combination of D-phenylalanine and D-leucine provides a greatly enhanced analgesia approaching the analgesia achieved by morphine. Analgesia by the latter combination is very long-lasting in animals. The injection of a combination of D-phenylalanine and an aspirin-like drug that is antipyretic and anti-inflammatory in an animal provides a greatly enhanced analgesia approaching the analgesia achieved by morphine. Analgesia by D-phenylalanine is very long-lasting in humans. D-phenylalanine also exhibits anti-inflammatory character, as demonstrated in animal tests.

6. Japanese Patent Number 1435284, issued Jul. 8, 1986, entitled CLASS OF ANALGESICS AND/OR ANTI-INFLAMMATORY A GENTS CONSISTING OF INHIBITORS OF BREAKDOWN OF ENDOGENOUS ENKEPHALIN AND/OR ENDORPHIN, AND COMBINATIONS OF SAID ANALGESICS WITH ANTIPYRETIC, ANTI-INFLAMMATORY (ASPIRIN-TYPE) DRUGS describes a new class of analgesics provided by substances that inhibit breakdown of endogenous substance such as enkephalins and/or endorphins. The analgesic effect of an enkephalin breakdown inhibitor is greatly enhanced by being combined with an antipyretic, anti-inflammatory analgesic, herein designated as an aspirin-type drug. Specifically, "both D-phenylalanine and D-leucine, each an enkephalin breakdown inhibitor, when used separately provides excellent analgesia in animals and man without developing tolerance or addiction in either species. Use of a combination of D-phenylalanine and D-leucine provides a greatly enhanced analgesia approaching the analgesia achieved by morphine. Analgesia by the latter combination is very long-lasting in animals. The injection of a combination of D-phenylalanine and an aspirin like drug that is antipyretic and anti-inflammatory, in an animal provides a greatly enhanced analgesia approaching the analgesia achieved by morphine. Analgesia by D-phenylalanine is very long-lasting in humans. D-phenylalanine also exhibits anti-inflammatory character, as demonstrated in animal tests.

7. A U.S. Patent Disclosure dated Mar. 18, 1999, entitled CLASS OF ANALGESICS AND/OR ANTI-INFLAMMATORY A GENTS CONSISTING OF INHIBITORS OF BREAKDOWN OF ENDOGENOUS ENKEPHALIN AND COMBINATIONS OF SAID ANALGESIC S WITH GANODERMA LUCIDUM describes a new class of analgesics provided by substances that inhibit breakdown of endogenous substance such as enkephalins and/or endorphins. The analgesic effect of an enkephalin breakdown inhibitor is greatly enhanced by being combined with an antipyretic, anti-inflammatory analgesic, herein designated as an aspirin-type drug. Specifically, both D-phenylalanine and D-leucine, each an enkephalin breakdown inhibitor, when used separately provides excellent analgesia in animals and man without developing tolerance or addiction in either species. Use of a combination of D-phenylalanine and D-leucine provides a greatly enhanced analgesia approaching the analgesia achieved by morphine. Analgesia by the latter combination is very long-lasting in animals. The unique combination of inhibitors of amino peptidaises and extracts of ganoderma lucidum provides synergistic analgesic and antiinflammatory effects in both animals and humans.

RDS Gene Testing

8. U.S. Pat. No. 5,210,016, issued May 11, 1993, entitled ALLELIC ASSOCIATION OF THE HUMAN DOPAMINE (D~) RECEPTOR GENE IN COMPULSIVE DISORDERS SUCH AS ALCOHOLISM relates to a method for diagnosing compulsive disease predisposition of an individual. The method comprises initially obtaining a DNA sample of said individual and then determining the presence or absence of a particular human D 2 receptor gene allele in said sample. Detection of said allele in the sample is indicative of predilection to compulsive disease. A most preferred embodiment is to detect predisposition to alcoholism, particularly because said allele has bee n found to be present in a majority of clinically diagnosed alcoholics. The human D 0.2 receptor gene A1 allele is most preferably detected in said sample.

9. U.S. Pat. No. 5,550,343, issued Mar. 19, 1996, entitled ALLELIC ASSOCIATION OF THE HUMAN DOPAMINE (D~) RECEPTOR GENE IN COMPULSIVE DISORDERS relates to an important embodiment, this invention concerns a method for detecting compulsive disorder susceptibility of a human. The method comprises initially obtaining a DNA sample of said human and then determining the presence or absence of a particular human D2 receptor gene allele in said sample. Detection of said allele in the sample is indicative of susceptibility to compulsive disorder. A most preferred embodiment is to detect a susceptibility to alcoholism and cocaine dependence, particularly because said allele has been found to be present in a majority of clinically diagnosed alcoholics and cocaine users. The human D2 receptor gene A1 and Bi alleles are most preferably detected in said sample.

10. U.S. Pat. No. 5,550,021, issued Aug. 27, 1996, entitled ALLELIC ASSOCIATION OF THE HUMAN DOPAMINE (D~) RECEPTOR GENE IN COMPULSIVE DISORDERS SUCH AS ALCOHOLISM describes a method for diagnosing compulsive disease predisposition of an individual. The method comprises initially obtaining a DNA sample of said individual and then determining the presence or absence of a particular human D 2 receptor gene allele in said sample. Detection of said allele in the sample is indicative of predilection to compulsive disease. A most preferred embodiment is to detect predisposition to alcoholism, particularly because said allele has been found to be present in a majority of clinically diagnosed alcoholics. The human D 2 receptor gene A1 allele is most preferably detected in said sample.

RDS Genetic Treatment

11. Li. U.S. Pat. No. 5,189,064, issued Feb. 23, 1993, entitled TREATMENT OF COCAINE ADDICTION describes cocaine addiction treated by administration of an endorphinase or enkephalinase inhibitor, and optionally, a dopamine precursor, or a serotonin precursor, a GABA precursor, or an endorphin or enkephalin releaser. These components promote restoration of normal neurotransmitter function and are non-addictive. Use of the dopamine precursors L-phenylalanine or L-tyrosine, the enkephalinase inhibitor D-patent opinion letters and infringement judgement).

12. U.S. Pat. No. 4,761,429, issued Aug. 2, 1988, entitled ENKEPHALINASE AND ENDORPHINASE INHIBITORS AS ANTI-CRAVING COMPOSITIONS, describes a new class of anti-craving compositions provided by substances which inhibit breakdown of endogenous substances such as enkephalins and/or endorphins. An anti-alcohol craving effect is observed with an enkephalin breakdown inhibitor. Specifically, D-phenylalanine, DL-phenylalanine, D-leucine, DL-leucine, and hydrocinnamic acid, each an enkephalin breakdown inhibitor, significantly lowered alcohol intake in animals and humans. The anti-alcohol desire effect is observed in animals genetically prone to choose alcohol over water solutions.

13. A U.S. patent application filed Apr. 29, 1998, entitled ALLELIC POLYGENE DIAGNOSIS OF REWARD DEFICIENCY SYNDROME AND TREATMENT describes enhancement of attentional processing attained by administration of an endorphinase inhibitor or enkephalinase inhibitor and optionally, a dopamine precursor, or a serotonin precursor, a GABA precursor, or an endorphin or enk ephalinase releaser, or certain herbal compounds including rhodiola rosea extract (pharmaline) and/or huperzine. These components promote restoration of normal neurotransmitter function and the components combined enhance the release of dopamine at the nucleus accumbens and are non-addictive. Use of the dopamine precursors L-phenylalanine, or L-Tyrosine, the enkephalinase inhibitor D-phenylalanine, and/or the serotonin precursor-hy droxytryptophan and a natural acetylcholenesterase inhibitor and chromium salts (i.e. picolinate, nicotinate, etc.) is especially preferred, but not limited to assist in relieving symptoms associated with brain phenylalanine deficiency.

14. A PCT Patent Application filed Apr. 29, 1998, entitled ALLELIC POLYGENE DIAGNOSIS OF REWARD DEFICIENCY SYNDROME AND TREATMENT, describes enhancement of attentional processing by administration of an endorphinase inhibitor or enkephalinase inhibitor and optionally, a dopamine precursor, or a serotonin precursor, a GABA precursor, or an endorphin or enkephalinase releaser, or certain herbal compounds including Rhodiola rosea extract (Pharmaline) and/or Huperzine. These components promote restoration of normal neurotransmitter function and the components combined enhance the release of dopamine at the nucleus accumbens and are non-addictive. Use of the dopamine precursors L-phenylalanine, or L-Tyrosine, the enkephalinase inhibitor D-phenylalanine, and/or the serotonin precursor-hydroxytryptophan and a natural acetylcholenesterase inhibitor and chromium salts (i.e. picolinate, nicotinate, etc.) is especially preferred, but not limited to assist in relieving symptoms associated with brain phenylalanine deficiency (See Table 4).

15. A U.S. Provisional Patent filed Jan. 12, 1999, entitled NEW CLASS OF ANTI-HYPERTENSIVE AGENTS INCLUDING INHIBITORS OF THE BREAKDOWN OF ENKEPHALINS AND/OR ENDORPHINS, AND COMBINATIONS OF SAID ANTI-HYPERTENSIVE AGENTS WITH OTHER ANTI-HYPERTENSIVE DRUGS AND NATURAL SUBSTANCES, describes the invention involving the combination of certain inhibitors of Endorphinase or Enkephalinase or other related inhibitors of enzymes involved in the breakdown of natural opioid peptides. These inhibitors could be from a group of D-amino acids and, their metabolites (i.e. D-phenylalanine, Hydrocinnamic acid D-leucine, etc.) and other precursor amino-acids, especially those which effect dopamine synthesis (i.e. L-tyrosine) as well as herbal-based natural substances (fairylike acid, pharmaline, hopers, hawthorn). The addition of chromium salts (picolinate, nicotinate & poly nicotinate etc.) to promote a reduced risk for diabetes, reduced cholesterol, and reduced blood pressure will be most beneficial. Other important nutrients include Co-enzyme Q and Pycnogenol and D-Ribose. The combination of D-amino acids or other similar inhibitors of opioid peptidyl degradation with known anti-hypertensive agents is also considered (See Table 2).

Synergene Nutralife System

Research into the potential market (See Table 5) prompted the development of the exclusive SynerGene NutraLife System natural essentials, which specifically has been designed to address health issues the natural way. In this regard, people today are quite concerned with health and well being issues.

TABLE 5

Health Concerns and Incidence of Illnesses

| | |
|---|---|
| Americans Concerned with General Well Being | 271,800,000 |
| Americans Over Age 40 Concerned with General Well Being | 250,056,000 |
| Americans Concerned with Mortality or Life Expectancy | 200,000,000 |
| Incidence of Common Cold and Influenza | 157,000,000 |
| Americans Concerned with Cognition/memory/focusing | 92,000,000 |
| Incidence of Battling Obesity or Being Overweight | 91,000,000 |
| Incidence of Hypertension | 60,000,000 |
| Incidence of Sexual Dysfunction | 56,000,000 |
| Incidence of Arthritis | 35,000,000 |
| Incidence of Adult Children of Alcoholics | 28,000,000 |

Use of the products described herein to address what is termed dysfunctions of the "The Brain Reward Cascade" through precursor amino-acid therapy and inhibition of the enzymatic breakdown of opioid peptides, such as the endogenous endorphins, is essential to establishing well being and a healthy life-style. If properly addressed, especially via natural ways, ultimately will lead to a successful prescription which allows people to achieve their life goal in better health through the SynerGene life style change system termed SMART (SynerGene Management Amino-Acid Replacement Therapy). A principal of this unique approach is the recognition that well being involves the interaction of both our genes and the environment.

In this regard, this is entering a new phase in the search for answers to the ancient questions:
What causes diseases?
How can they be Prevented?
How they can be cured?

The past century has seen breakthroughs that led to an understanding of bacteria and infections; to extraordinary progress in the technology of diagnostics and to the art of surgery; to a new understanding of the role of emotion in disease states; to an equally extraordinary expansion of the pharmacopeia; and to a new understanding of the role of nutrition in brain function.

Now, we are approaching the most exciting period in the history of the human science. On the one hand, we are watching the efforts of researchers as they push the investigational envelop:

1. viral infections responsible for afflictions such as ADDS and certain of the cancers;
2. genetic anomalies that appear to be determining factors in neurological diseases such as cystic fibrosis, and impulsive-compulsive-addictive disorders we term "Reward Deficiency Syndrome" and related behaviors.
3. the design and synthesis of drugs that target specific receptor sites and enzymes;
4. plants and organisms that manufacture natural substances with therapeutic value. From earliest times individuals and sometimes whole societies have self-medicated with substances such as coca leaves, opium, and fermented sugars to relieve their fears or discomforts. Now, scientists are carrying out systematic searches in the forests and the oceans that will enrich the pharmacopeia.

CyberPharm scientists are watching the development of a new orientation toward the interaction of brain, emotion, and behavior that may affect us even more profoundly. As in the years when we watched psychosomatic medicine clarifying the role of emotions in a variety of illnesses, we are now beginning to understand that genetic defects leading to deficiencies and imbalances in neurotransmitters, enzymes, and receptors may give rise to a wide range of behavioral disturbances. These somatic syndromes constitute exciting new frontiers in prevention and treatment of diseases or disorders.

Just as emotional and mental disturbances cause organic disturbances leading to physical illness, so somatic predispositions, deficiencies, or imbalances may cause emotional and mental disturbances such as "Reward Deficiency Syndrome" (See Table 6) and related behaviors but also anxiety, hostility, depression, or reclusive or anti-social attitudes and responses.

TABLE 6

Reward Deficiency Syndrome Behaviors

| | | | | |
|---|---|---|---|---|
| Addictive Behaviors | Severe Alcoholism | Polysubstance Abuse | Nicotine Dependence | Carbohydrate Bingeing |
| Impulsive Behaviors | Attention Deficit Hyperactivity Disorder | | Tourette Disorder | Autism |
| Compulsive Behaviors | Aberrant Sexual Behavior | | Pathological Gambling | |
| Personality Disorders | Conduct Disorder | Antisocial Personality | Aggressive Behavior | |

The inventor believes that behavioral as well as certain physical anomalies may not be primary aberrations, but may represent instead, the effort of the mind to adapt to the consequences of defects in genes.

The SynerGene NutraLife SMART Composition

It is relevant to point out that claim 10 of U.S. Pat. No. 5,189,064, issued Feb. 23, 1993 essentially reads as follows:
A pharmaceutical composition which consists essentially of:
an opiate destruction-inhibiting amount of at least one substance which inhibits enzymatic destruction of a neuropeptidyl opiate, such as a substance being selected from the group consisting of:

1 an amino acid 2 peptides 3 analogues or derivatives of (1) or (2) above, and a neurotransmitter synthesis —promoting amount of at least one neurotransmitter precursor selected from the group consisting of the dopamine precursors—1-Tyr. I-Phe and 1-dopa; the serotonin precursors—I—Trp and 5-hydroxytryptophan; and the gamma amino butyric acid (GABA) precursors—1-glutamine, I-glutamic acid, the amount of said substance and said neurotransmitter precursor being chosen so that the composition is effective in reducing the subject's craving.

The SynerGene NutraLife Essentials have been designed by utilizing a composition to affect brain chemistry through amino-acid precursors and opioid peptide enzymatic breakdown inhibitors and herbals and essential botanicals to promote a health life style change.

It should be understood that the SMART blend, based on the above referenced patent, is used in all the Neutraceutical products. In this regard each product consists of a SMART blend composition designed specifically for the disorder in question. The neutraceuticals which contain a SMART blend include KRA vEx, STIMEX, NicoEx, PMX and PROCOG. While Table 7 generally describes a number of these essentials, specific details of a number of products are presented emphasizing the rationale for basic activity, animal and clinical research support and active ingredient list, as well as benefits and features.

TABLE 7

SynerGene ™
Product Descriptions

| PRODUCT NAME[1] | Type of Product | PURPOSE | NEUROTRANSMITTER MECHANISM |
|---|---|---|---|
| Dorfamin | Neutraceutical (CNS) | Branded name of racemic formulation of dl-phenylalanine | CyberPharm's patented, branded combination of d-phenylalanine and l-phenylalanine which is the major constituent of all neutraceuticals. |
| KravEx[2] | Neutraceutical (CMS) | Reduces craving in Severe Alcoholism | Designed to increase activity of the opioid peptide system leading to dopamine release at the reward site. |
| Alcotox | Neutraceutical (CNS) | Reduces withdrawal symptoms of alcoholism during acute phase of withdrawal | Replenishes important electrolytes and enhances neurotransmitter balance. |
| BodySynergy[3] ™ | Neutraceutical (CNS) | Reduces craving in Carbohydrate Bingeing | Designed to Stimulate the Brain Glucose Receptor Leading to Dopamine Release at the Reward Site. |
| StimEx[3,4] | Neutraceutical (CNS) | Reduces craving in Crack/Cocaine Dependence | Designed to maintain normal neurotransmipper balance in brain reward sites while enhances the release of Dopamine |
| NicoEx[1] ™ | Neutraceutical (CNS) | Reduces craving in Nicotine Dependence and Smoking Behavior | Designed to Activate Both the Dopamine Reward Site and the Anxiety Brain Site including herbal calming essentials. |
| GamboEx | Neutraceutical (CNS) | Reduces compulsive behavior in Pathological Gambling | Designed to Work Through Serotonergic and Opioid Activation, the Neutraceutical Will Enhance Dopamine Release into the Reward Site of the Brain. |
| PolyEx | Neutraceutical (CNS) | Reduces drug craving and drug seeking behavior in patients with multiple addictions. | Designed to maintain normal neurotransmitter balance in brain reward sites while enhances the release of Dopamine |
| PMX ™ | Neutraceutical (CNS) | Relieves symptoms of premenstrual stress or premenstrual dysphoric disorder | During the luteal phase, PMX enhances the neurotransmitter pathways such as serotonergic, opioidergic, GABAergic, and catecholeminergic including herbal female support essentials. |
| ProCog ™ | Neutraceutical (CNS) | Attention Deficit Hyperactivity Disorder (ADHD) and Tourette's Disorder | Designed to Stimulate the O, Receptor Sites. Similar to Ritalin but is Accomplished via Natural Processes, includes herbal cognitive essentials. |
| ProFlex | Nutraceutical (PNS) | Reduces systemic pain, muscle and joint inflammation thereby increasing joint mobility and reducing pain in intractable pain patients | Enhances opioid peptide activity by inhibiting breakdown of the opioids. Provides synergistic analgesic and anti-flammatory properties by combining dl-Phenylalanine and *gamoderma lucidum* and other herbs working through multiple mechanisms including prostaglandins |
| CardioPlex | Nutraceutical (PNS) | Long term reduction of high blood pressure without affecting normal blood pressure | Enhances opioid peptide activity by inhibiting breakdown of the opioids resulting in peripheral dopamine release. Includes natural cognitive enhancers and anti-hypertensive agents. |
| Stess-Ex | Neutraceutical (CNS) | Reduces general background stress, anxiety, and depression; provides symptomatic treatment of posttraumatic stress disorder | Enhances opioid peptide activity by inhibiting breakdown of the opioids resulting in peripheral dopamine release. May affect phenylethylamine activity. Includes herbal calming essentials. |

TABLE 7-continued

SynerGene ™
Product Descriptions

| PRODUCT NAME[1] | Type of Product | PURPOSE | NEUROTRANSMITTER MECHANISM |
|---|---|---|---|
| ImunoPro | Nutraceutical (PNS) | Enhance immune response | Enhances opioid peptide activity by inhibiting breakdown of the opioids resulting in peripheral dopamine release including zinc complexes of dl-Phenylalanine and other immune enhancing herbals. |

[1] Subject to name search and regulation
[2] The use of our amino acid formulation in "Alcostat" has resulted in a six fold reduction in the number of patients leaving treatment Against Medical Advice, or leaving treatment before completion.
[3] The amino acid found in "StimEx" is a patented nutraceutical of CyberPharm's called Tropamine. Of all commonly used medications for the treatment of cocaine addiction, Tropamine has been clinically determined to be the most effective in preventing or reducing detoxification symptoms.
[4] The amino acid found in Tropamine has been found to be the most effective of all commonly used medications for the treatment of cocaine addiction in preventing relapse and in providing maintenance after treatment.

SynerGene NutraLife Essentials, Neutraceuticals, is a selective grouping of products providing unique dietary supplements comprised of SMART Blend and specific vitamins and minerals formulated to support healthy brain chemistry balance which promotes the normal physiological drives of hunger, drinking and sex. The basic concept of this important category resides in the understanding that impulsive-compulsive-addictive behaviors constitute a very significant proportion of the world population. In the United States alone there are 28 million adult children of alcoholics, twenty-two million a alcoholics, fifty-four million smokers, ninety-two million overeaters/obese, ten million cocaine dependent persons, five to eight million young children with attention deficit-hyperactivity (ADSD), over three million pathological gamblers and millions of sex addicts. Over the last three decades our understanding of this grave societal dilemma has grown and today in the 90's we are in the decade of the brain. Certainly, even more rapid advances will come before the millennium. While the basic pharmacology, biochemistry, neurochemistry, toxicology, and pharmacogenetics of abusable drugs have not changed much over the years, the psycho-biology and molecular genetic aspects of a new discipline known as Addiction Medicine (supported by the American Medical association), have significantly increased with better understanding of the meaning of the addiction process in general.

One important outcome of the basic understanding of addiction medicine is "Reward Deficiency Syndrome". In this term scientists embrace the fact that addictive impulsive compulsive behaviors including alcoholism, attention deficit disorder, drug abuse, smoking behavior and food binging—may have a common genetic root. The SynerGene NutraLife neutraceuticals were designed to address this dilemma. The inventor foresees the possibility for promoting a healthier life-style change in those victims carrying the genetic predisposition to related "reward seeking" behaviors.

Scientific evidence reveals the healing powers of botanicals, herbals and amino-acids. These natural substances have been associated with stress reduction, anti-hypertension, enhancement of mood, improve d immune response, stimulation of sexual performance, increased focus and cognition, reduced carbohydrate binging, and anti-craving action. Herbs and phyto-medicines are experiencing explosive growth in pharmacies and other mass-market retail outlets. An estimated 30 percent of American adults (60 million persons) are reported to be using herbs and phyto-medicinal products, spending an estimated $ 3.24 billion in 1996 and much more in the years to follow. An excellent example of the mainstream acceptance of well-researched herbs and phyto-medicines can be seen in a huge increase in sales of St. John's Wort, Ginko, Ginsing, Garlic, Echinacia and Saw Palmetto. Granting herbs some legal protection as dietary supplements in the United States, was clarified in the report from the senate committee on Labor and Human Resources that accompanied Senate Bill 784, the HatchHarkin bill, eventually passed and became the DSHEA.

The natural healing powers of many herbals and botanicals have been known for thousands of years, and even more profound is the understanding that brain endogenous mechanisms seed natural healing processes leading to well being. Therefore, combining nature's photo-medicines and amino-acid precursors to alter brain chemistry (affect on the mind), contributes to a powerful healing approach.

The SynerGene NutraLife Essentials meet established standards for purity and all products are subject to testing through rigorous quality-control methods.

Nutraceuticals are the category the products address peripheral disorder that are still influenced by the brain but the products are a combination of specific herbals and natural patented substances having very specific uses which have end actions on organs controlled by the peripheral nervous system. For example, the uses of D-amino acids such as d-phenylalanine have analgesic and anti-inflammatory actions as well as the use of water extracts of gandermalucidum as an anti-inflammatory. Another example of CyberPharm nutraceutical products involves the anti-hypertensive properties of enkephalinase inhibitors including d-phenylalanine. In the area of immune enhancement, CyberPharm has products involving the combination of zinc-dlphenylalanine and herbals which promote a positive immune response. The products in this category include PRoFLEx, CARDIOPLEX, and MuNoPRo (See the Intellectual Property Section above for amore detailed description of the science and technology behind these products). The Neutraceutical Product, KRAVEX, consists of amino-acid precursor amines, natural enkephalinase inhibitors, minerals, vitamins trace metals, and herbals. The product is designed to promote normal physiological drive especially in individuals prone to addictive behavior of the depressant kind. Based on a number of clinical trials (See Table 4), the KRAVEX essential is designed to affect abnormal cravings for depressant type abusable substances such as alcohol, barbiturates and benzodiazepine anti-anxiety agents.

TABLE 4

SUMMARY OF COMPLETED CLINICAL STUDIES WITH 1899 L.L.C. NEUTRACEUTICAL SUPPLEMENTATION
A Literature Review

| DRUG ABUSED OR DYSFUNCTION | SUPPLEMENT USED | NO. OF PTS. | NO. OF DAYS | STUDY TYPE | SIGNIFICANT RESULTS | PUBLICATION |
|---|---|---|---|---|---|---|
| Alcohol | SAAVE | 22 | 28 | TO IP | 100 percent decrease in BUD scores. Detoxification measures: reduction in benzodiazepine requirement, reduction in withdrawal tremors after 72 hours, reduction in depression | Blum K, Trachenberg M C, Ramsey J. improvement of inpatient treatment of the alcoholic as a function of neuronutrient restoration: a pilot study. Int J Addiction. 1988; 23:991-98. Blum K, Trachenberg M C. Neurogenic deficits caused by alcoholism: restoration by SAAVE. Journal of Psychoactive Drugs. 1988; 20:297. |
| Alcohol plus Polydrugs | SAAVE | 62 | 21 | DBPC IP | Reduction in psychosocial stress reduction as measured by SCL, reduced BESS score, improved physical score, six-fold decrease in likelihood of leaving AMA after five days. | Blum et al. Enkephalinase inhibition and precursor amino acid loading improves inpatient treatment of alcoholics and poly-drug abusers: a double-blind placebo-controlled study of the neuronutrient intervention adjunct SAAVE. Alcohol. 1989; 5:481. |
| Cocaine | Tropamine | 54 | 30 | TO IP | Drug hunger significantly reduced in patients taking SAAVE as compared to controls; 4.2 percent AMA rate for patients on Tropamine versus 28 percent for patients on SAAVE and 37 percent for controls. | Blum et al. Reduction of both drug hunger and withdrawal against advice rate of cocaine abusers in a 30 day inpatient treatment program with the neuronutrient tropamine. Curr Ther Res. 1988; 43:1204. |
| Alcohol and Cocaine | SAAVE and Tropamine | 60 | 379 | TO CP | At end of one year over 50 percent of the alcoholic DUI offenders not using SAAVE dropped out of the program while less than 15 percent of those using SAAVE dropped out. For the cocaine abusers over 90 percent of the Non-Tropamine group dropped out, but less than 25 percent of the patients in the control group. | Brown et al. Neurodynamics of relapse prevention: a neuronutrient approach to outpatient DUI offenders. J. Psychiatric Drugs. 1990; 22:173. |
| Over-Eating | PCAL 103 | 27 | 90 | TO OP | The PCAL 103 group lost an average of 27 pounds in 90 days compared with an average loss of 10 pounds for the control group. Only 18.2 percent of the PCAL 103 patient group relapsed compared to 82 percent of the patients in this control group. | Blum et al. Neuronutrient effects on weight loss on carbohydrate bingeing in a bariatric setting. Curr Ther Res. 1990; 48:2a17. |
| Over-Eating | PCAL 103 | 247 | 730 | PCOT OP | After two years, craving and binge eating were reduced one-third in group of patients on PCAL 103, as compared to the control patients. PCAL 103 group regained 14.7 pounds of their lost weight compared with 41.7 percent weight regained in control patients. | Blum K, Cull J G, Chen J H T, Garcia-Swan S, Holder J M, Wood R, et al. Clinical relevance of PhenCal in maintaining weight loss in an open-label, controlled 2-year study. Curr Ther Res. 1997; 58:745-63. |
| Over-Eating | Chromium Picolinate (CP) and L-Carnitine | 40 | 112 | RDBPC CP | 21 percent increase (p < 0.001) in resting metabolic rate (RMR), no change in lean body mass (LBM), RMR:LBM increased 25 percent (p < 0.001). Body fat decreased approximately 1.5 lbs./week, and reduction in serum cholesterol while increasing RMR with no loss of LBM | Kaats F E et al. The short-term therapeutic effect of treating obesity with a plan of improved nutrition and moderate caloric restriction. Curr Ther Res. 1992; 51:261. |
| Over-Eating | Chromium Picolinate | 32 | 180 | DBPC OP | After six months the CrP group had an increase in lean body mass and avoided non-fat related weight loss. Difference between groups was significant at | Bahadori B, Habersack S, Schneider H, Wascher T C, Topiak H. Treatment with chromium picolinate improves lean body mass |

TABLE 4-continued

SUMMARY OF COMPLETED CLINICAL STUDIES WITH 1899 L.L.C. NEUTRACEUTICAL SUPPLEMENTATION
A Literature Review

| DRUG ABUSED OR DYSFUNCTION | SUPPLEMENT USED | NO. OF PTS. | NO. OF DAYS | STUDY TYPE | SIGNIFICANT RESULTS | PUBLICATION |
|---|---|---|---|---|---|---|
| Over-Eating | Chromium Picolinate | 154 | 72 | RDBPC OP | $p < 0.001$. 200 and 400 mcg of CrP brought about significant changes in Body Mass composition indicies when compared with placebo | in patients following weight reduction. Federation Am Soc Exp Bio 1995. Kaats F E, Blum K, Fisher J A, Aldeman J A. Effects of chromium picolinate supplementation on body mass composition: a randomized, double-blind, placebo-controlled study. Curr Ther Res. 1996; 57:747–56 |
| Over-Eating | Chromium Picolinate | 122 | 90 | RDBPC OP | After controlling for differences in caloric expenditure and caloric intake as compared with the placebo group, 400 mcg CrP group lost significantly more weight ($p < 0.001$) and body fat ($p < 0.004$), had a greater reduction in body fat ($p < 0.001$), significantly improve body composition ($p < 0.004$). | Kaats F E, Blum K, Pullin D, Keith S C, Wood R. A randomized double-masked placebo-controlled study of the effects of chromium picolinate supplementation on body composition: a replication of previous study. Curr Ther Res. 1998; 59:379–88. |
| Over-Eating | Chromium Picolinate | 122 | 90 | RDBPC OP | Measures of changes in fat weight, change in body weight, percent change in weight, and body weight changes in kgms were all significant in A2/A2 group, and non-significant in A1/A2 and A1/A1 carriers. | Blum K, Kaats G, Eisenberg A, Sherman M, Davis K, Comings D E, Cuill J G, Chen T H J, Wood R, Bucci L, Wise J A, Braverman E R, and Pullin D. Chromium Picolinate induces Changes in Body Composition as a Function of the Taq1 Dopamine D2 Receptor A1 Alleles. Submitted to Journal of the American College of Nutrition. |
| Over-Eating | Chromium Picolinate and Chromium Picolinate comparison | 43 | 63 | ROTPC OP | CrP supplementation resulted in significant weight gain, while exercise training combined with CrP supplementation resulted in significant weight loss and lowered insulin response to an oral glucose load. Concluded high levels of CrP supplementation are contraindicated for weight loss, in young obese women. Moreover, results suggested that exercise combined with CrP supplementation may be more beneficial than exercise training alone for modification of certain CAD or NIDDM risk factors | Grant K E, Chandler R M, Castle A L, Ivy J L. Chromium and exercise training; effect on obese women. J Am Sports Med 1997; 29(8):992–8. |
| Healthy Volunteers | Tropagen | 15 | 30 | DBPC OP | Non-drug subjects with Tropagen performed better on computer memory and performance tasks as measured with P300 wave evoked potential. Changes in P300 wave evoked potential result in better focusing ADHD patients | Defrance J J, Hymel C, Trachtenberg M C et al. Enhancement of attention processing by Kantrol in healthy humans: A pilot study. Clin Electroencephalgr. 1997; 28:68–75. |

Abbreviations used:
BUD—building up to drink; AMA—withdrawal against medical advice; OP—outpatient; MMPI—Minnesota Multiphasic personality inventory; DB—double-blind; IP—inpatient; SCL—skin conductance level; BESS—behavioral, emotional, social, spiritual; DBPC—double-blind placebo-controlled; DUI—driving under the influence; R—randomized; TO—open trial Our brain chemistry could be compromised either at birth through genetic variants and/or through environmental elements resulting in an impaired Brain Reward Cascade and a hypodopaminergic dysfunction. In fact it is important to realize that as we get older we tend to lose dopamine function which leads to craving behavior in our senior citizens. It is for this reason that many of our older population abuse psychoactive prescription medication (tranquilizers) and even alcohol. Because of this, proper nourishment is essential for the health of brain function to reduce aberrant cravings for certain substances like alcohol or depressant drugs.

KRAVEX is a unique, scientifically advanced product that provides a multi-nutritional approach to normal brain function. It supplies your brain with a proprietary blend of amino-acids to mimic the Brain Reward Cascade providing proper balance consisting of chromium salts to enhance penetration of select precursor amino-acids (tryptophan to assist in the synthesis of serotonin), minerals, vitamins, riboflavin and folic acid to act as co-factors for the production of A neurotransmitters, and Kava Kava as a natural calming substance, as well as both calcium and magnesium to regulate neurotransmitter release, and Arctic root, known as Rhodiola rosea (the Russian alpine plant) which promotes healthy serotonergic and dopaminergic balance, thereby promoting balanced mood. In this essential, arctic root extract is standardized to 1.0 percent rosavins and 1.0 percent salidrsides.

TABLE 8

| BENEFITS | FEATURES |
| --- | --- |
| Formulated to Increase Well Being* | Features Patented Blend of Amino-acids. |
| Helps Your Body to Adjust to Stress* | Contains Chromium with Active Compounds Such as Riboflavin, Pantothenic Acid, and Cyanocobalamin. |
| Designed to Balance the "Brain Reward Cascade"* | Includes Such Herbals as Kava Kava and *Rhodiola Rosea*, a Russian Alpine Plant with Neurotransmitter Balancing Activity. |
| Induces the Brain to Have Normal Physiological Urges* | Includes Patented Natural Endorphin Enhancers. |
| Reduces Craving for Depressant-like Substances* | Consists of Calcium and Magnesium for Proper Dopamine Release. |

*These statements have not been evaluated by the Food and Drug Administration. This product is not intended to diagnose, treat, cure or prevent disease.

In terms of craving behavior each product developed will address a specific type of craving. In this regard, KRAVEx, has been designed to effect addiction to depressant-like drugs such as alcohol, barbiturates an d tranquilizers. The basic pharmacological principal, is like treats like. Therefore, the ingredients found in this neutraceutical promotes a feeling of calm and increased well being. In general, since deficits have been found in brain chemical functions underlying craving behavior, and since these deficits may be alleviated by facilitated dopamine release consequent to the use of drugs such as alcohol, combining amino-acid precursors and enkephalinase inhibition may simulate the brain's reward system and compensate for neurotransmitter imbalance (thereby attenuating craving behavior). In an attempt to understand that depressant-drug abuse seeking behavior (craving), is a subset of generalized craving behavior (Reward Deficiency Syndrome), due in part to low dopamine function (an impaired reward cascade), scientists believe individuals self-heal through biochemical attempts to alleviate the low dopaminergic brain activity via drug (alcohol)-reward site interaction. Since the brain is made up of 200 billion cells and these: cells require good nutrition, which includes minerals, vitamins, trace metals and amino acids, this neutraceutical provides these important elements in a special brain stabilizing blend along with ancient calming herbals (benzodiazepinelike) which together reduce craving and enhances well being.

Nutritional Information

TABLE 9

Supplement Facts
Serving Size: 1 Caplet
Servings Per Container: 90

| Amount per Serving | % Daily Value |
| --- | --- |
| Blend | + |
| Arctic Root Extract (*Rhodiola Rosea*) 300 mg Standardized to 1.0% Rosavins, 25 mg Standarized to 1.0% Salidrosaides | + |
| Kava Kava (Root) 90 mg | + |
| German Chamomile (Flower Heads) | + |
| Hops (Strobiles) | + |

+ Minimum Daily Requirements not established for this ingredient.
Important Notes:
Do not take this product if you are pregnant or nursing, if you are taking an MAO inhibitor type anti-depressant or if you are known to have PKU. Do not exceed the recommended dose except under the supervision of a physician. Do not use with other substances that cause drowsiness (alcohol). Use caution when operating a motor vehicle or machinery. If you are under a physician's care or taking medication, consult your health care practitioner.

It is important to realize that each product consists of the SMART~Blend, (See Table 10).

TABLE 10

SMART ™ Blend Composition in KravEx ™ and Rationale for Use
(Amounts are for a daily dose of six Caplets)

| Ingredient | Amount | Restorative Action | Mechanism | Behavioral Change |
| --- | --- | --- | --- | --- |
| d-Phenylalanine | 750 mg. | Enkephalins | Enzyme Inhibition | Anti-Craving Anti-Depression |
| l-Phenylalanine | 750 mg. | Dopamine Norepinephrine | Precursor Loading | Reward Anti-Depression |
| l-5-Hydroxytryptophan | 20 mg. | Seratonin | Precursor Loading | Anti-Craving Anti-Depression Anti-Insomnia |
| l-Glutamine | 300 mg. | GABA | Precursor Loading | Anti-Craving Anti-Stress |

TABLE 10-continued

SMART ™ Blend Composition in KravEx ™ and Rationale for Use
(Amounts are for a daily dose of six Caplets)

| Ingredient | Amount | Restorative Action | Mechanism | Behavioral Change |
|---|---|---|---|---|
| Vitamin B Complex | | Neurotransmitter Synthesis | Enzyme Co-Factor in Neurotransmitter Synthesis | Facilitates Action of Neurotransmitter |
| Thiamin HCL | 100 Mg. | Vitamin B | Enzyme Co-Factor in Neurotransmitter Synthesis | Facilitates Action of Neurotransmitter |
| Riboflavin | 15 mg. | Vitamin $B_7$ | Enzyme Co-Factor in Neurotransmitter Synthesis | Facilitates Action of Neurotransmitter |
| Niacinamide | 100 mg. | Vitamin $B_3$ | Enzyme Co-Factor in Neurotransmitter Synthesis | Facilitates Action of Neurotransmitter |
| Pantothenic Acid | 90 mg. | Vitamin $B_3$ | Enzyme Co-Factor in Neurotransmitter Synthesis | Facilitates Action of Neurotransmitter |
| Pyridoxal-5-phosphate | 20 mg. | Vitamin $B_2$ Active Metabolite | Promotes Gastrointestinal Absorption of Amino Acids | Facilitates Action of Neurotransmitter |
| Cyanocobalamin | 6 µg | | | Facilitates Action of Neurotransmitter |
| Ascorbate (Calcium) | 750 mg. | Neurotransmitter Synthesis | Enzyme Co-Factor | Facilitates Action of Neurotransmitter |
| Folic Acid | 400 µg. | Neurotransmitter Synthesis | Enzyme of Co-Factor | Facilitates Action of Neurotransmitter |
| Zinc (Chelate) | 30 mg. | Neurotransmitter Synthesis | Enzyme Co-Factor | Facilitates Action of Neurotransmitter |
| Calcium (Chelate) | 150 mg. | Neurotransmitter Modulator | Regulates Neurotransmitter Release | Facilitates Action of Neurotransmitter |
| Magnesium (Oxide) | 150 mg. | Neurotransmitter Modulator | Regulates Neurotransmitter Release | Calmative |
| Chromium Picolinate | 1500 µg | Neurotransmitter Modulator | Enhances Amino Acid Brain Penetration | Facilitates Action of Neurotransmitter |

STIMEX consists of amino-acid precursor amines, natural enkephalinase inhibitors, minerals, vitamins trace metals, and herbals. The product is designed to promote normal physiological drive especially in individuals prone to addictive behavior of the stimulant kind. Based on a number of clinical trials (See Table 4) the STIMEX essential is designed to affect abnormal cravings for stimulant-like drugs (i.e. cocaine).

Our brain chemistry can be compromised either at birth through genetic variants and/or through environmental elements resulting in an impaired Brain Reward Cascade and a hypodopaminergic dysfunction. It is well known that low dopamine function induces aberrant cocaine-seeking behavior in both animals and humans. Blocking dopamine receptors with specific dopamine type 2 receptor antagonists has been shown to induce abnormal cravings for stimulant-like drugs such amphetamines and cocaine. In the February 1999 issue of the American Journal of Psychiatry (I 999) it was reported that chronic cocaine abusers have a low number of total dopamine nerve terminals and a high number of cocaine metabolizing sites (dopamine transporter binding sites). These dopaminergic abnormalities contribute to cocaine craving behavior.

Because of this, proper nourishment is essential for the health of brain function to reduce aberrant cravings for substances that release dopamine from the neurons in the reward sites of the brain such as certain stimulants like cocaine. STIMEX is a unique, scientifically advanced product that provides a multi-nutritional approach to normal brain function. The product supplies your brain with a proprietary blend of amino-acids to mimic the reward cascade providing proper balance, chromium salts to enhance penetration of select precursor amino-acids (tryptophan to assist in the synthesis of serotonin) minerals, vitamins, riboflavin and folic acid to act as co-factors for the production of neurotransmitters, certain stimulant type herbals—Ginger Root, Siberian Ginsing Root, and a mood enhancer proprietary blend (Gotu Kola Leaf, Cola Nut, and Mate) as well as both calcium and magnesium to regulate neurotransmitter release, and Fairylike acid, a natural substance which promote s brain chemistry balance by its action on the serotonergic, opioid peptidergic (Endorphins) and dopaminergic pathways.

TABLE 11

| BENEFITS | FEATURES |
|---|---|
| Formulated to Increase Well Being* | Features Patented Blend of Amino-acids. |
| Helps Your Body to Adjust to Stress* | Contains Chromium with Active Compounds Such as Riboflavin, Pantothenic Acid, and Cyanocobalamin. |
| Designed to Balance the "Brain Reward Cascade"* | Includes such herbals as Ferrulic acid, Ginsing, Ginger, Cola Nut, Mate, and Gotu Kola |
| Induces the Brain to Have Normal Physiological Urges* | Includes Patented Natural Endorphin Enhancers. |
| Reduces Craving for Stimulant-like Substances* | Consists of Calcium and Magnesium for Proper Dopamine Release. |

*These statements have not been evaluated by the Food and Drug Administration. This product is not intended to diagnose, treat, cure or prevent disease.

STIMEX is designed to affect addiction to stimulant-like drugs such as cocaine, amphetamines, caffeine The basic pharmacological principal, is like treats like. Therefore, the ingredients found this addiction essential promotes a feeling of well being. In general, since deficits have ben found in brain chemical functions underlying craving behavior, and since these deficits may be activated by facilitated dopamine release consequent to the use of stimulant-type drugs like cocaine and amphetamines, combining amino acid precursors and enkephalinase inhibition may simulate the brain's reward system and compensate for neurotransmitter imbalance (thereby attenuating craving behavior). It is now understood that stimulant-like drugs induce dopamine release in the reward sites of the brain and stimulant drug seeking behavior (craving) is a subset of generalized craving behavior ("Reward Deficiency Syndrome"), due in part to low dopamine function (an impaired cascade). Scientists believe that, for example cocaine addicts, self-heal through biochemical attempts to alleviate the low dopaminergic brain activity via cocaine-reward site interaction. Since the brain is made up of 200 billion cells and these cells require good nutrition, which includes minerals, vitamins, trace metals and amino acids, this addiction-essential provides these important elements in a special brain stabilizing blend along with well-being enhancer herbals (dopaminergic-like) which reduces craving for stimulants by enhancing dopaminergic function through natural replacement therapy.

Nutritional Information

TABLE 12

Supplement Facts
Serving Size: 1 Caplet
Servings Per Container: 90

| Amount per Serving | % Daily Value |
|---|---|
| Blend | + |
| Methionine 60 mg | + |
| Octacosinol 2 mg | + |
| Stim Blend 75 mg | |
| Ginger Root | + |
| Siberian Ginsing | + |
| Mood Enhancer Blend 200 mg | |
| Gotu Kola Leaf | + |
| Cola Nut | + |
| Mate Folium | + |
| Ferulic Acid 50 mg | + |

+ Minimum Daily Requirements not established for this ingredient.
Important Notes:
Do not take this poduct if you are pregnant or nursing, if you are taking an MAO inhibitor type anti-depressant or if you are known to have PKU. Do not exceed the recommended dose except under the supervision of a physician. Reduce intake of caffeine if you are under a physician's care or taking medication, consult your health care practitioner.

It is important to realize that each product consists of the SMART blend, which varies with each specific product (See Table 13).

TABLE 13

SMART ™ Blend Composition in StimEx ™ and Rationale for Use
(Amounts are for a daily dose of six Caplets)

| Ingredient | Amount | Restorative Action | Mechanism | Behavioral Change |
|---|---|---|---|---|
| d-Phenylalanine | 750 mg. | Enkephalins | Enzyme Inhibition | Anti-Craving Anti-Depression |
| l-Phenylalanine | 750 mg. | Dopamine Norepinephrine | Precursor Loading | Reward Anti-Depression |
| l-Tyrosine | 900 mg. | Dopamine Norepinephrine | Precursor Loading | Reward Anti-Depression Anti-Stress |
| l-5-Hydroxytryptophan | 20 mg. | Serotonin | Precursor Loading | Anti-Craving Anti-Depression Anti-Insomnia |
| l-Glutamine | 300 mg. | GABA | Precursor Loading | Anti-Craving Anti-Stress |
| Vitamin B Complex | | Neurotransmitter Synthesis | Enzyme Co-Factor in Neurotransmitter Synthesis | Facilitates Action of Neurotransmitter |
| Thiamin HCL | 100 Mg. | Vitamin B | Enzyme Co-Factor in Neurotransmitter Synthesis | Facilitates Action of Neurotransmitter |
| Riboflavin | 15 mg. | Vitamin $B_7$ | Enzyme Co-Factor in Neurotransmitter Synthesis | Facilitates Action of Neurotransmitter |
| Niacinamide | 100 mg. | Vitamin $B_3$ | Enzyme Co-Factor in Neurotransmitter Synthesis | Facilitates Action of Neurotransmitter |
| Pantothenic Acid | 90 mg. | Vitamin $B_3$ | Enzyme Co-Factor in Neurotransmitter Synthesis | Facilitates Action of Neurotransmitter |
| Pyridoxal-5-phosphate | 20 mg. | Vitamin $B_2$ Active Metabolite | Promotes Gastrointestinal Absorption of Amino Acids | Facilitates Action of Neurotransmitter |
| Cyanocobalamin | 6 µg. | | | Facilitates Action of Neurotransmitter |
| Ascorbate (Calcium) | 500 mg. | Neurotransmitter Synthesis | Enzyme Co-Factor | Facilitates Action of Neurotransmitter |
| Folic Acid | 400 µg. | Neurotransmitter Synthesis | Enzyme Co-Factor | Facilitates Action of Neurotransmitter |
| Zinc (Chelate) | 30 mg. | Neurotransmitter Synthesis | Enzyme Co-Factor | Facilitates Action of Neurotransmitter |
| Calcium (Chelate) | 150 mg. | Neurotransmitter Modulator | Regulates Neurotransmitter Release | Facilitates Action of Neurotransmitter |
| Magnesium (Oxide) | 150 mg. | Neurotransmitter Modulator | Regulates Neurotransmitter Release | Calmative |
| Chromium Picolinate | 1500 µg. | Neurotransmitter Modulator | Enhances Amino Acid Brain Penetration | Facilitates Action of Neurotransmitter |

NICOEX consists of amino-acid precursor amines, natural enkephalinase inhibitors, minerals, vitamins trace metals, and herbals. The product is designed to promote normal physiologic drive especially in individuals prone to addiction to nicotine.

While there is a paucity of research with regard to NICOEX, in contrast, there are a number of clinical trials with regard to the Addiction-Essential Blend and alcoholism (See Table 4). Scientists are in agreement that both nicotine and alcohol commonly induce the release of dopamine from reward site neurons. In fact, there is strong evidence that the increase in dopamine levels in the brain reward site (n. accumbens) produced by alcohol is mediated by nicotinic receptors. In the February 1999 issue of Alcohol it was reported that alterations in the nicotinic system affects alcohol self-administration in animals. Taken together this suggests that since the neutraceutical was quite effective in reducing alcohol craving then other dopamine releasing drugs like nicotine also would be similarly affected. Because of this, proper nourishment is essential for the health of brain function to reduce aberrant cravings for substances that release dopamine from the neurons in the reward sites of the brain such as nicotine.

NICOEX is a unique, scientifically advanced product that provides a multi-nutritional approach to normal brain function. The product supplies your brain with a proprietary blend of amino-acids to mimic the Brain Reward Cascade providing proper balance, chromium salts to enhance penetration of select precursor amino-acids (tryptophan to assist in the synthesis of serotonin), minerals, vitamins, riboflavin and folic acid to act as co-factors for the production of neurotransmitters, certain calming herbals-Ashwagandha Root Extract, Valerian Root Extract, Kava Kava (root), Chamomile (flower-head), and Hops (strobiles). Other ingredients include Lecithin, and Beta-Carotene. This essential could be part of a NicoEx Quit Kit which will be comprised of a Life Style Change Plan, and a specially designed anti-nicotine cigarette filter using an ion exchange resin. The kit also could include a homeopathic quit smoking blend.

TABLE 14

| BENEFITS | FEATURES |
|---|---|
| Formulated to reduce nicotine craving* | Features Patented Blend of Amino-acids. |
| Helps Your Body to Adjust to Stress* | Contains Chromium with Active Compounds Such as Riboflavin, Pantothenic Acid, Cyanocobalamin, Lecithin, and Beto-Carotene. |
| Designed to Re-Balance the "Brain Reward Cascade"* | Includes such herbals as Ashwaganda Root, Valerian Root, Kava Kava, and Chamomile |
| Induces the Brain to Have Normal Physiological Urges* | Includes Patented Natural Endorphin Enhancers. |
| Designed to Offset Weight Gain from Smoking Withdrawal* | Consists of Calcium and Magnesium for Proper Dopamine Release. |
| Formulated to Increase a Sense of Well Being* | Includes Ascorbic Acid to Assist in Withdrawal |

*These statements have not been evaluated by the Food and Drug Administration. This product is not intended to diagnose, treat, cure or prevent disease.

Smoking involves far more than physical addiction to nicotine. The road to stop smoking is not simply a matter of "just saying no". Similar to other addictive substances (i.e. alcohol, cocaine, glucose etc.), the most successful approach is to bring about a life-style change. The SMART approach to quitting corrects nutritional deficits and emphasizes improved nutritional intake, exercise and behaviors that will help the smoker become smoke-free. As a smoker, the body constantly is being robbed of vital nutrients. Moreover, the 54 million smokers are not only placing their bodies under the influence of stress-inducing substances like nicotine, but may indeed be more genetically prone to overreact toward stressful events. This is based on a number of reports linking one variant of the dopamine D2 receptor gene to smoking behavior. This same variant has been linked to alcoholism, carbohydrate binging, cocaine dependence, pathological gambling and an inability to cope with stress. In this regard, nicotine is known to release dopamine from neurons in the brain reward site and this effect is paramount to its addictive qualities. Scientists believe that nicotine dependent persons, self-heal through biochemical attempts to alleviate the low dopaminergic brain activity via nicotine—reward site interaction. Stress is an inescapable element in life which can negatively impact your health and is linked to many disorders such as substance abuse, cancer, cardiovascular disorders, headaches, ulcers, weakened immune response as well as other health problems. It is noteworthy, that abuse of nicotine via smoking is linked to stress and smoking behavior leads to poor nutrition. Since the brain is made up of 200 billion cells and these cells require good nutrition, which includes minerals, vitamins trace metals, and amino acids, this addiction—essential provides these important elements in a special natural calming blend along with the anti-craving composition which reduces craving for nicotine by enhancing dopaminergic function through natural replacement therapy.

Nutritional Information

TABLE 15

Supplement Facts
Serving Size: 1 Caplet
Servings Per Container: 90

| Amount per Serving | % Daily Value |
|---|---|
| Blend | + |
| Lecithin 120 mg | + |
| Beta Carotine 25,000 I.U. | 500 |
| Ashwaganha Root Extract 200 mg Standarized to 1.5% Withanolides, 3 mg Standarized to !% Alkaloids, 2 mg | + |
| Valerian Root Extract 67 mg Standardized to 0.8% Valeranic Acid, 0.5 mg | + |
| Calming Blend 133 mg | + |
| Kava Kava (root) | + |
| German Chamomile (flower-head) | + |
| Hops (strobiles) | + |

+ Minimum Daily Requirements not established for this ingredient.
Important Notes:
Do not take this product if you are pregnant or nursing, if you are taking an MAO inhibitor type anti-depressant or if you are known to have PKU. Do not exceed the recommended dose except under the supervision of a physician. Do not use with other substances that cause drowsiness (alcohol). Use caution when operating a motor vehicle or machinery. If you are under a physician's care or taking medication, consult your health care practitioner.

It is important to realize that each product consists of the SMART Blend, which varies slightly with each specific product (See Table 16).

TABLE 16

SMART ™ Blend Composition in NicoEx ™ and Rationale for Use
(Amounts are for a daily dose of six Caplets)

| Ingredient | Amount | Restorative Action | Mechanism | Behavioral Change |
|---|---|---|---|---|
| d-Phenylalanine | 750 mg. | Enkephalins | Enzyme inhibition | Anti-Craving Anti-Depression |
| l-Phenylalanine | 750 mg. | Dopamine Norepinephrine | Precursor Loading | Reward Anti-Depression |
| l-Tyrosine | 750 mg. | Dopamine Norepinephrine | Precursor Loading | Reward Anti-Depression Anti-Stress |
| l-5-Hydroxytryptophan | 20 mg. | Serotonin | Precursor Loading | Anti-Craving Anti-Depression Anti-Insomnia |
| l-Glutamine | 400 mg. | GABA | Precursor Loading | Anti-Craving Anti-Stress |
| Vitamin B Complex | | Neurotransmitter Synthesis | Enzyme Co-Factor in Neurotransmitter Synthesis | Facilitates Action of Neurotransmitter |
| Thiamin HCL | 100 Mg. | Vitamin B | Enzyme Co-Factor in Neurotransmitter Synthesis | Facilitates Action of Neurotransmitter |
| Riboflavin | 15 mg. | Vitamin $B_7$ | Enzyme Co-Factor in Neurotransmitter Synthesis | Facilitates Action of Neurotransmitter |
| Niacinamide | 130 mg. | Vitamin $B_3$ | Enzyme Co-Factor in Neurotransmitter Synthesis | Facilitates Action of Neurotransmitter |
| Pantothenic Acid | 90 mg. | Vitamin $B_3$ | Enzyme Co-Factor in Neurotransmitter Synthesis | Facilitates Action of Neurotransmitter |
| Pyridoxal-5-phosphate | 20 mg. | Vitamin $B_2$ Active Metabolite | Promotes Gastrointestinal Absorption of Amino Acids | Facilitates Action of Neurotransmitter |
| Cyanocobalamin | 6 μg. | | | Facilitates Action of Neurotransmitter |
| Ascorbate (Calcium) | 500 mg. | Neurotransmitter Synthesis | Enzyme Co-Factor | Facilitates Action of Neurotransmitter |
| Folic Acid | 600 μg. | Neurotransmitter Synthesis | Enzyme Co-Factor | Facilitates Action of Neurotransmitter |
| Zinc (Chelate) | 30 mg. | Neurotransmitter Synthesis | Enzyme Co-Factor | Facilitates Action of Neurotransmitter |
| Calcium (Chelate) | 150 mg. | Neurotransmitter Modulator | Regulates Neuro-transmitter Release | Facilitates Action of Neurotransmitter |
| Magnesium (Oxide) | 150 mg. | Neurotransmitter Modulator | Regulates Neuro-transmitter Release | Calmative |
| Chromium Picolinate | 1500 μg | Neurotransmitter Modulator | Enhances Amino Acid Brain Penetration | Facilitates Action of Neurotransmitter |

PMX consists of amino-acid precursor monoamines, natural enkephalinase inhibitors, minerals, vitamins, trace metals, and herbals. The product is designed to promote normal physiologic drive especially in individuals prone to Premenstrual Dysphoric Disorder (PMD b). a premenstrual mood disorder that recurs cyclically during the majority of menstrual cycles.

While there is a paucity of research with regard to PMX in contrast there are number of clinical trials with regards to the neutraceutical and "Reward Deficiency Syndrome" and related behaviors (See Table 4). It is noteworthy, a former product known as SAAVE, in which over 100,000 female alcoholics used to reduce craving, many reported attenuation of PMDD symptoms. The scientific basis for this effect resides in the affect PMX will have on the brain's "Brain Reward Cascade". The four pathways involved include Serotonergic, Opioidergic (endorphins), GABAergic and Adrenergic. In women with severe premenstrual dysphoria it was found that compared with asymptomatic controls, symptomatic women have lower levels of serotonin. It also has been found that during the luteal phase platelet serotonin uptake is decreased with PMDD as compared to controls. In addition, depleting the serotonin precursor tryptophan is significantly more likely to provoke premenstrual symptoms during both luteal and follicular phases in PMDD patients compared to asymptomatic women. In four studies it was found that lower luteal phase Beta-endorphin levels in symptomatic patients compared with controls. More over, during the premenstrual period, levels of both endorphin and estrogen change rapidly and there are reports that narcotic antagonists reduce PMDD symptoms. Others have found decreases in plasma gamma-aminobutyric acid levels during the luteal phase in women with PMDD symptoms. Recently, it was found that plasma methionine-enkephalin and a decrease in plasma norepinephrine levels on day 22 in menstrual migraine group and an increase in plasma methionine, norepinephrine during pain. Moreover, while the above biological evidence does not definitively implicate any single, neurobiological system, changes in serotonin levels, endorphinergic activity, GABA levels and adrenergic binding activity, suggest neurobiological abnormalities associated with an impaired "Brain Reward Cascade" and subsequent expression of PMD. Because there is no single-neurotransmitter involved but instead it is a multi-neurotransmitter phenomenon, proper nourishment is essential for the health of brain function to reduce PMDD expression.

PMX is a unique, scientifically advanced product that provides a multi-nutritional approach to normal brain function. The product supplies your body with a patented blend of amino-acids to mimic the reward cascade providing proper balance, chromium salts to enhance penetration of select precursoramino-acid (tryptophan to assist in the synthesis of serotonin), minerals, vitamins, riboflavin and folic acid to act as co-factors for the production of neurotransmitters, certain natural patented pain killers-d-phenylalanine (See U.S. Pat. No. 4,687,781) and belladonna, a natural anti-anxiety blend-passionflower, hops, and, Female Support Blend-black cohash root, chaste tree fruit, ipriflavone, and natural anti-spasmotics-peppermint leaf, Scopolia root, and licorice root. In the largest study ever conducted on PMDD, patients administered 1200 mg of calcium reported symptoms at a rate of fifty percent of those patients on the placebo.

TABLE 17

| BENEFITS | FEATURES |
|---|---|
| Formulated to reduce PMDD and PMS Symptoms* | Features Patented Blend of Amino-acids. |
| Helps Your Body to Adjust to Stress* | Includes Patented Natural Pain Killer |
| Designed to Re-Balance the "Brain Reward Cascade"* | Includes Patented Natural Endorphin Enhancers. |
| Helps Your Body to Reduce Pain, and Elevate Mood* | Contains Chromium with Active Compounds Such as Riboflavin, Pantothenic Acid, Cyanocobalamin, Calcium and Magnesium for Both Co-factors and Neurotransmitter Release. |
| Formulated to Enhance a Sense of Well Being* | Consists of Anti-anxiety, Anti-spasmodic and Female Support Blends. |

*These statements have not been evaluated by the Food and Drug Administration. This product is not intended to diagnose, treat, cure or prevent disease.

SYNOPSIS

These statements have not been evaluated by the Food and Drug Administration. This product is not intended to diagnose, treat, cure or prevent disease.

Premenstrual Dysphoric Disorder (PMDD) is a premenstrual mood disorder that recurs cyclically during the majority of menstrual cycles. It is included under the category of Depressive Disorders not otherwise specified in the American Psychiatric Association's DSM-IV. However, a number of factors (biological and cognitive treatment responses) differentiate PMDD from other mood disorders. Despite the predictability of luteal phase symptom expression, the etiology of this disorder has not been established. Theories regarding hormonal and vitamin deficiencies have been associated with PMDD. Moreover, neither absolute nor relative deficits of progesterone, estrogen, prostaglandin, insulin, vitamin B 6 or thyroid hormone have been established in patient groups with PMDD.

It is noteworthy, that certain drugs have been used to treat PMDD such as antidepressants (clonipramine, fluoxitine, buprion, paroxetine, maprotiline, sertraline, and fenfluramine). Most scientists would agree that one-single drug with only limited effects on one single or possibly even two individual neurotransmitters is insufficient to overcome the abnormal state of the "reward" system which occurs by hormonal shifts in the female pre-, during, and post-menstrual phase. There is enough literature to indicate that the function of four neurotransmitter pathways (serotonergic, opioidergic, GABAergic, and adrenergic) have been associated with PMDD and related symptoms.

Therefore, the SMART approach will influence the "Brain Reward Cascade" causing neurotransmitter release which induces an enhanced well being. Moreover, the combination of providing pain relief, anti-spasmodic, anti-anxiety herbal blends will have significant impact on effecting symptoms associated with PMDD. For up to 10 days each month, some 25 million women suffer from bloating, cramping, moodiness, breast tenderness, migraines, acne and food cravings.

TABLE 18

Supplement Facts
Serving Size: 1 Caplet
Servings Per Container: 90

| Amount per Serving | % Daily Value |
|---|---|
| Blend | |
| Dandelion root 35 mg | + |
| Belladonna root 50 mg | + |
| Standardized to 0.125 mg total alkaloids, | |
| calculated as hyoscyamine. | |
| Calming Blend 150 mg | |
| Passionflower (passiflorae) | + |
| Hops (strobile) | + |
| German Chamomile (flower heads) | + |
| Female Support Blend 100 mg | |
| Black Cohash (root) | + |
| Chaste Tree Fruit | + |
| Ipriflavone | + |
| Anti-Spasmotic Blend | |
| Peppermint leaf 50 mg | + |
| Scopolia root | + |
| Standardized to 0.1 mg total alkaloids | |
| calculated as hyoscyamine | |
| Licorice root (equivalent to 25 mg glycyrrhizin) | + |

+ Minimum Daily Requirements not established for this ingredient.

Important Notes:

Do not take this product if you are nursing, if you are taking an MAO inhibitor type anti-depressant or if you are known to have PKU. Do not exceed the recommended dose except under the supervision of a physician. Do not use with other substances that cause drowsiness (alcohol). Use caution when operating a motor vehicle or machinery. If you are under a physician's care or taking medication, consult your health care practitioner.

It is important to realize that each consists of the SMART Blend, which varies slightly with each specific essential (See Table 19). Below is the recommended formulation of the supplement for PMS and PMDD; however, this basic formulation can be modified by the selective addition of Cramp Bark (A Muscle Relaxant), Lavender Oil (A Topical Analgesic and Muscle Relaxant); Vitex (A Hormone Balancer That Stimulates Production of Progesterone to Alleviate Breast Tenderness, Mood Swings, Food Cravings, Acne, and Constipation); Valerian Root (A Sedative Which Relaxes Muscles and Reduces Anxiety and Moodiness Through Depressing the Central Nervous System); Devil's Club (Eliminates Irritability, Fatigue, and Headaches), Dong Qual (relieves menstrual cramping, Evening Primrose (reduces breast tenderness), Flaxseed (reduces menstrual bleeding).

TABLE 19

SMART ™ Blend Composition in PMX ™ and Rationale for Use
(Amounts are for a daily dose of six Caplets)

| Ingredient | Amount | Restorative Action | Mechanism | Behavioral Change |
|---|---|---|---|---|
| d-Phenylalanine | 750 mg. | Enkephalins | Enzyme Inhibition | Anti-Craving Anti-Depression |
| l-Phenylalanine | 750 mg. | Dopamine Norepinephrine | Precursor Loading | Reward Anti-Depression |
| l-5-Hydroxytryptophan | 20 mg. | Serotonin | Precursor Loading | Anti-Craving Anti-Depression Anti-Insomnia |
| l-Glutamine | 500 mg. | GABA | Precursor Loading | Anti-Craving Anti-Stress |
| Vitamin B Complex | | Neurotransmitter Synthesis | Enzyme Co-Factor in Neurotransmitter Synthesis | Facilitates Action of Neurotransmitter |
| Thiamin HCL | 100 Mg. | Vitamin B | Enzyme Co-Factor in Neurotransmitter Synthesis | Facilitates Action of Neurotransmitter |
| Riboflavin | 15 mg. | Vitamin $B_7$ | Enzyme Co-Factor in Neurotransmitter Synthesis | Facilitates Action of Neurotransmitter |
| Niacinamide | 100 mg. | Vitamin $B_3$ | Enzyme Co-Factor in Neurotransmitter Synthesis | Facilitates Action of Neurotransmitter |
| Pantothenic Acid | 90 mg. | Vitamin $B_3$ | Enzyme Co-Factor in Neurotransmitter Synthesis | Facilitates Action of Neurotransmitter |
| Pyridoxal-5-phosphate | 20 mg. | Vitamin $B_2$ Active Metabolite | Promotes Gastrointestinal Absorption of Amino Acids | Facilitates Action of Neurotransmitter |
| Cyanocobalamin | 6 µg. | | | Facilitates Action of Neurotransmitter |
| Ascorbate (Calcium) | 750 mg. | Neurotransmitter Synthesis | Enzyme Co-Factor | Facilitates Action of Neurotransmitter |
| Folic Acid | 400 µg. | Neurotransmitter Synthesis | Enzyme Co-Factor | Facilitates Action of Neurotransmitter |
| Zinc (Chelate) | 30 mg. | Neurotransmitter Synthesis | Enzyme Co-Factor | Facilitates Action of Neurotransmitter |
| Calcium (Chelate) | 1200 mg. | Neurotransmitter Modulator | Regulates Neurotransmitter Release | Facilitates Action of Neurotransmitter |
| Magnesium (Oxide) | 150 mg. | Neurotransmitter Modulator | Regulates Neurotransmitter Release | Calmative |
| Chromium Picolinate | 1500 µg. | Neurotransmitter Modulator | Enhances Amino Acid Brain Penetration | Facilitates Action of Neurotransmitter |

PROCOG consists of amino-acid precursor monoamines, natural enkephalinase inhibitors, minerals, vitamins, trace metals and herbals. The product is designed to promote normal physiological drive, enhance focus and memory and bring about normal behavioral activity in inattentive, compulsive hyperactive individuals.

There is clinical evidence that the neutraceutical PROCOG significantly enhances cognitive event-related potentials associated with performance. In fact, in young adult healthy volunteers the SMART Blend amino-acid composition enhanced visual attention tasks, spacial orientation, contingent continuous performance and P300 wave magnitude and latency. In terms of cognition, it is well known that brain electrical activity analysis has revealed the existence of subtle neurological change in a wide variety of disorders including depressions, criminal pathology, Alzheimers, auto-immune-deficiency syndrome (AIDS), drug addictions and attention deficit hyperactivity disorder (ADHD). With regard to the latter, a study in the early 70's showed that a major ingredient in PROCOG, dl-phenylalanine, a natural enhancer of opioid peptides (endorphins), by preventing the breakdown of these biologically active peptides, increased the mood and reduced anxiety in subjects diagnosed with ADHD.

Our brain is an intricate organ that controls every thought, every move and every gesture we make moment by moment. In order to carry out these complex functions the brain depends on oxygen. Oxygen is vital for nerve cells to properly transmit chemical messengers. It is noteworthy, that experiments in swine, provide evidence that the natural opioid methionine-enkephalin when administered to the swine resulted in enhancement of blood flow in specific brain sites especially in the basal ganglia, frontal cortex, and hippocampus, important reinforcement and memory sites. It is logical that increases of the neurotransmitter enkephalin, by inhibition of the enzyme enkephalinase, would augment brain oxygenation via increased blood flow.

It also is important to point out that cognition is associated with the chemical messenger dopamine. Recent human studies reveal substances such as bromocriptine, that mimic dopamine at its receptor sites, increase short term memory. In this regard, the neutraceutical provides the brain with precursor amino-acids leading to the release of dopamine in the reward site. The product supplies your body with a patented blend of amino-acids to mimic the reward cascade providing proper balance, chromium salts to enhance penetration of select precursor amino-acid (tryptophan to assist in the synthesis of serotonin), minerals, vitamins, riboflavin, and folic acid to act as co-factors for the production of neurotransmitters, a natural patented enhancer of brain blood flow, d-phenylalanine (See U.S. Patent Pending and PCT application) and certain herbals that effect cognition including; huperzine, bacopa monalera, ginko biloba, ginsing, gotu kola, ferulic acid, and rhodiola rosea extract promotes mental sharpness and alertness.

TABLE 20

| BENEFITS | FEATURES |
| --- | --- |
| Improves Circulation and Oxygenation of the Brain.* | Features Patented Natural Endorphin Enhancer. |
| Helps Promote Memory Enhancement and Focus.* | Includes Patented Brain Blood Flow Enhancer. |
| Promotes the Release of Dopamine to Assist in Cognition.* | Consists of Memory and Focus Herbals for Alertness Such as Huperzine, Ferulic Acid and Pharmaline. |
| Designed to Enhance Well Being.* Reduces Hyperactivity.* | Provides Bacosides from Bacopa. Contains Ginkosides, Active Constituents Found in Ginko Biloba Extract. |
| Increases Ability to Cope with Stress* | Includes Rosemary and Gotu Kola |

*These statements have not been evaluated by the Food and Drug Administration. This product is not intended to diagnose, treat, cure or prevent disease.

SYNOPSIS

These statements have not been evaluated by the Food and Drug Administration. This product is not intended to diagnose, treat, cure or prevent disease.

Attentional processing has been shown to be dependent on biogenic amine regulation. Since the precursors for synthesizing the amines are dependent upon dietary intake, it is possible that dietary supplements can alter available biogenic amine stores in the brain. This has led to various clinical strategies that target nutritional improvement of the brain's chemistry for enhancing memory and focus. Defects in dopamine metabolism have long been implicated in attentional processing (short-term memory) as well as ADHD. There are specific reasons for this relationship: studies in rodents show that destruction of dopaminergic brain nerve cells results in hyperactivity and, poor response to stress; studies in rodents showing that the chemical destruction of frontal lobe dopaminergic neurons shortly after birth produces an animal model of ADHD that responds to stimulants; an association of low levels of dopamine metabolites in children with ADHD; brain imaging studies show deficits of dopaminein ADHD subjects; hyperactivity is produced in mice when dopaminergic genes (dopamine transporter and dopamine D3 receptor genes) are knocked out; and, effectiveness of drugs which mimic dopamine in the treatment of poor cognition including ADHD.

The brain is one of the most active body tissues. Although it constitutes only about five percent of body weight and it consumes 20 percent of the available oxygen, it is indeed the master organ. PRoCoG is formulated to maintain healthy levels of oxygen and blood flow as well as enhancing well being. With this combination of a patented amino-acid composition and phyto-medicines, the brain is better able to maintain its vitality and stay alive. Also using a similar formula we could develop a product for the sports market place. The product, named Endorphin Boost, would be an endorphin replacement supplement needed after strenuous exercise.

TABLE 21

Supplement Facts
Serving Size: 1 Caplet
Servings Per Container: 90

| Amount per Serving | % Daily Value |
| --- | --- |
| Blend | + |
| Ferulic Acid 50 mg | + |
| Huperzine 0.15 mg | + |
| Arctic Root Extract (*Rhodiola rosea*) 25 mg | + |
| Standardized to 1.0% Rosavins, 0.25 mg | + |
| Standardized to 1.0% Salidrosides, 0.25 mg | + |
| Bacopa Monolera Leaf Extract 100 mg | + |
| Standardized to 20% of active ingredient. | |
| Ginko Biloba Leaf extract 40 mg | + |
| Standardized to 24% ginko flavone | |
| Glycosides, 14.4 mg | |
| Standardized to 6% Terpene lactones 3.6 mg | |
| Panax Ginseng 60 mg | + |
| Standardized to 14% ginsenosides | |
| Rosemary Leaf 50 mg | + |

+ Minimum Daily Requirements not established for this ingredient.

Important Notes:

Do not take this product if you are pregnant or nursing, if you are taking an MAO inhibitor type anti-depressant, if you have high blood pressure, or if you are known to have PKU. Do not exceed the recommended dose except under the supervision of a physician. Reduce intake of caffeine. If you are under a physician's care or taking medication, consult your health care practioner.

It is important to realize that the SMART Blend, which varies with each specific essential. (See Table 22).

TABLE 22

Composition of ProCog ™ and Rationals for Use
(Amounts are for a daily dose of six Caplets)

| Ingredient | Amount | Restorative Action | Mechanism | Behavioral Change |
| --- | --- | --- | --- | --- |
| d-Phenylalanine | 750 mg. | Enkephalins | Enzyme inhibition | Anti-Craving Anti-Depression |
| l-Phenylalanine | 750 mg. | Dopamine Norepinephrine | Precursor Loading | Reward Anti-Depression |
| l-Tyrosine | 900 mg. | Dopamine Norepinephrine | Precursor Loading | Reward Anti-Depression Anti-Stress |
| l-Glutamine | 300 mg. | GABA | Precursor Loading | Anti-Craving Anti-Stress |

TABLE 22-continued

Composition of ProCog ™ and Rationals for Use
(Amounts are for a daily dose of six Caplets)

| Ingredient | Amount | Restorative Action | Mechanism | Behavioral Change |
|---|---|---|---|---|
| Vitamin B Complex | | Neurotransmitter Synthesis | Enzyme Co-Factor in Neurotransmitter Synthesis | Facilitates Action of Neurotransmitter |
| Thiamin HCL | 100 Mg. | Vitamin B | Enzyme Co-Factor in Neurotransmitter Synthesis | Facilitates Action of Neurotransmitter |
| Riboflavin | 15 mg. | Vitamin $B_7$ | Enzyme Co-Factor in Neurotransmitter Synthesis | Facilitates Action of Neurotransmitter |
| Niacinamide | 100 mg. | Vitamin $B_3$ | Enzyme Co-Factor in Neurotransmitter Synthesis | Facilitates Action of Neurotransmitter |
| Pantothenic Acid | 90 mg. | Vitamin $B_3$ | Enzyme Co-Factor in Neurotransmitter Synthesis | Facilitates Action of Neurotransmitter |
| Pyridoxal-5-phosphate | 20 mg. | Vitamin $B_2$ Active Metabolite | Promotes Gastrointestinal Absorption of Amino Acids | Facilitates Action of Neurotransmitter |
| Cyanocobalamin | 6 µg. | | | Facilitates Action of Neurotransmitter |
| Ascorbate (Calcium) | 600 mg. | Neurotransmitter Synthesis | Enzyme Co-Factor | Facilitates Action of Neurotransmitter |
| Folic Acid | 600 µg. | Neurotransmitter Synthesis | Enzyme Co-Factor | Facilitates Action of Neurotransmitter |
| Zinc (Chelate) | 30 mg. | Neurotransmitter Synthesis | Enzyme Co-Factor | Facilitates Action of Neurotransmitter |
| Calcium (Chelate) | 1200 mg. | Neurotransmitter Modulator | Regulates Neurotransmitter Release | Facilitates Action of Neurotransmitter |
| Magnesium (Oxide) | 150 mg. | Neurotransmitter Modulator | Regulates Neurotransmitter Release | Calmative |
| Chromium Picolinate | 1500 µg. | Neurotransmitter Modulator | Enhances Amino Acid Brain Penetration | Facilitates Action of Neurotransmitter |

PROFLEX consists of amino-acid natural enkephalinase inhibitor, mushroom, minerals, vitamins, and herbals with specific analgesic and anti-inflammatory effects. The product is designed to promote mobile joints, rebuild cartilage and maintain connective tissue. PROFLEX helps provide temporary relief of minor pains from arthritis.

While there is a paucity of research with regard to PROFLEX specifically, there are numerous animal and clinical reports regarding the pain killing and anti-inflammatory properties of certain d-amino acids such as d-phenylalanine. The amino acid, d-phenylalanine, is a natural inhibitor of opioid peptides (i.e. enkephalins, endorphins, and dynorphins) in both animals and humans. D-phenylalanine has been shown to enhance the analgesic effects of acupuncture. In double-blind studies the compound has induced analgesia in patients reactive to approved analgesic drugs including opiates. In cross-over studies in humans D-phenylalanine reduced pain associated with osteo- and rheumatoid arthritis. The anti-inflammatory mechanism of action of the D-amino acids appears to involve the prostaglandins via an opioid peptide interaction. The product also includes *ganoderma lucidum* extract which has been shown to have a number of biological actions. In mice the water extract of *ganoderma lucidum* was found to be a potent anti-inflammatory agent. An extracted and characterized compound was as active as hydrocortisone without the typical side effects (thymic involution and gastropathy).

Since the anti-inflammatory effect observed in mice worked in both the carrageenan and croton oil experiments, indicates that the mushroom based compound may have multiple mechanisms. CyberPharm's scientists believe the combination of d-phenylalanine with *ganoderma lucidum* could have powerful synergistic actions. The combination of d-phenylalanine and a number of non-steroidal substances like aspirin are synergistic in animal carrageenan experiments. A benefit of this essential is the addition of glucosamine, a substance known to act as a building block of the proteoglycons, an essential constituent of collagen, which gives cartilage its cushioning property. It has been suggested that glucosamine is require d to make the material that binds water in the cartilage matrix.

The product supplies your body with patented natural pain killers having anti-inflammatory properties such as DL-phenylalanine and an extract of the mushroom *ganoderma lucidum*, as well as white willow bark a natural, aspirin-like form of salicin. The product also consists of a blend of herbals such as boswellia, bromelian nettle leaf, and a homeopathic osteo-blend including active ingredients such as monkshood, deadly nightshade, wild hops, leopard's bane, and poison ivy which support healthy joint function. PROFLEX also contains calcium and magnesium for bone density support.

TABLE 23

| BENEFITS | FEATURES |
|---|---|
| Reduces Pain Associated with Joint Swelling* | Provides a Patented Natural Pain Killer and Anti-inflammatory Composition. |
| Promotes Cartilage Repair and Regeneration* | Includes Patent Pending Natural Anti-inflammatory Agent. |
| Supports Healthy Joint Function and Mobility* | Features Glucosamine for Healthy Cartilage. |

TABLE 23-continued

| BENEFITS | FEATURES |
|---|---|
| Prevents Muscle Fatigue* | Includes Natural Homeopathic Ingredients. |
| Provides Active Anti-Inflammatory Action* | Supplies the Mobility Support of Herbals. |

*These statements have not been evaluated by the Food and Drug Administration. This product is not intended to diagnose, treat, cure or prevent disease.

The PROFLEX SYNERGY PACK is a selective companion system which consists of natural pain killers, anti-inflammatory agents, herbals, and homeopathic ingredients which when taken together supplies the body with active substances known to promote healthy joint function in a synergistic manner. It is well known that as our bodies age, connective tissue and cartilage needs important nutrients to maintain vitality. It is also well known that in seniors the ability to produce some of these nutrients necessary for cartilage building declines. Proper nutrients safe guard against inflammation of all the 143 different joints in the human body such as hands, feet, fingers, wrists, elbows, neck, shoulders, knee, back, hip, and ankles. The patented PROFLEX-SYNERGY-SYSTEM is the most natural scientifically advanced product that provides a nutritional approach to both reduction of pain and inflammation through its DL-Phenylalanine (See U.S. Pat. No. 4,730,007) and its natural (1899 LLC and the University of Texas System) extract of ganodermalucidum, which has been shown to be a very potent anti-inflammatory agent. Using gas chromatography and mass spectral analysis along with NMR and X-ray techniques two isomers were identified out of several hundred triterpines in the mushroom, both having significant anti-inflammatory properties. The product supplies your body with the Indian herb boswellia, known for its anti-inflammatory effects in humans, glucosamine, a naturally occurring amino-sugar found in the body, which plays a role in maintaining and rebuilding cartilage and acts as a "shock absorber"

It is anticipated that the gene test will involve a gene recently discovered by George UHL and colleagues involving one's sensitivity to pain related to an endogenous opioid.

TABLE 24

Supplement Facts
Serving Size: 1 Caplet
Servings Per Container: 90

| Amount per Serving | % Daily Value |
|---|---|
| dl-Phenylalanine 750 mg | + |
| Glucosamine HCL 500 mg | + |
| Calcium (Chelate) 225 mg | |
| Magnesium (Oxide) 150 mg | |
| White Willow Bark 60 mg | + |
| Standardized to 1 percent total Salicin | |
| Ganoderma Lucidum 750 mg | + |
| Standardized to Percent of Isomer X | |
| Flex Blend 120 mg | |
| Bozwellia serrata Gum Resin | + |
| Bromelein | + |
| Nettle Leaf | + |
| HOMEOPATHIC FLEX PACK | |
| Aconitum Napellus (Monkshood) | 6x |
| Belladonna (Deadly Nightshade) | 6x |
| Bryonia Alba (Wild Hops) | 6x |

TABLE 24-continued

Supplement Facts
Serving Size: 1 Caplet
Servings Per Container: 90

| Amount per Serving | % Daily Value |
|---|---|
| Arnica Montana (Leopard's Bane) | 6x |
| Rhus Toxiconendron (Poison Ivy) | 6x |

+ Minimum Daily Requirements not established for this ingredient.
Important Notes:
Do not use this product in cases with PKU, if you are pregnant or nursing. If you are under the care of a physicians or taking medication consult your health professional before taking product. If you are allergic to shellfish or mushrooms do not take. For severe pain or if minor pain persists for seven days consult a health care professional immediately. Take as directed and keep away from children.

CARDIOPLEX consists of amino-acid precursor monoamines, natural enkephalinase inhibitors, minerals, vitamins, trace metals and herbals. The product is designed to promote healthy cardiovascular function and normal blood pressure.

To date, there are no clinical trials on CARDIOPLEX per se, but certain ingredients have been tested in both animals and humans. There are a number of classes of drugs which currently are in use to treat hypertension. These consist of the following: drugs which modify the adrenergic part of the autonomic nervous system; drugs which dilate blood vessels; diuretics, drugs that inhibit angiotensin converting enzyme; drugs that block calcium channels; and, drugs that block angiotensin receptors. With this in mind, the inventor has CyberPharm's scientists have discovered a natural anti-hypertensive substance which by itself lowers blood pressure in hypertensive individuals without causing blood pressure lowering in normals. A provisional patent was filed on Jan. 12, 1999 entitled Hypertensive Agents Including Inhibitors of the Breakdown of Enkephalins and/or Endorphins and Combinations of SAID, Anti-Hypertensive Agents with other AntiHypertensive Drugs and Natural Substances. The enkephalins and endorphins are peptides which are present in blood and in the central nervous system. Although their main function appears to be control of the pain response, they have other important actions including lowering blood pressure in some animal species, but these compounds have many drawbacks when administered.

Ehrenpreis discovered the natural enkephalinase inhibitor d-phenylalanine is highly effective in lowering blood pressure in animals and in man and is the major ingredient of CARDIOPLEX. In this regard, our scientists found that D-phenylalanine significantly lowered both systolic and diastolic blood pressure with no change in heart rate in genetically bred spontaneously hypertensive rats (SHR). D-Phenylalanine was able to lower systolic blood pressure of these rats close to normal (average drop of 36.7 mm Hg). It is noteworthy that this effect is blocked by the narcotic antagonist and the effect on blood pressure is synergistic with the beta-blocker popranolol. Even more important is that the lowering of blood pressure by d-phenylalanine lasted several days. A single dose of d-phenylalanine lowers blood pressure for one or more days in human 5 having no effect in normotensive individuals.

Because there is no single neurotransmitter involved in controlling blood pressure, we have designed CARDIOPLEX as a combination of substances which have been shown in numerous studies to promote a healthy heart. In fact d-ribose is included, since it plays a role in myocardial metabolism and post-myocardia schemia. The product also includes the trace metal chromium nicotinate because it has been shown to reduce blood pressure in humans. Moreover the patented SMART composition was found in one study to reduce blood pressure when given on a chronic basis. Unique to this product is the addition of certain herbs that enhance cognition including huperzine, rhodiola rosea extract, and ganoderma lucidum as well as other natural anti-hypertensive agents like hawthorn berry, Co-enzyme Q, and Pycogenol. It also is important to supply the body with two amino-acids, Lysine and Proline, which help in preventing fat buildup.

TABLE 25

| BENEFITS | FEATURES |
| --- | --- |
| Lowers Blood Pressure* | Includes Patented Natural Anti-Hypertensive. |
| Promotes Oxygenation of Cells* | Includes a Chromium as an Anti-Hypertensive. |
| Enhances Cognition, Especially for Seniors* | Contains Anti-Oxidants and Vitamins. |
| Prevents Free Radical Damage* | Includes Huperzine, Rhodiola Rosea, and Ganoderma Lucidum |
| Helps Maintain Elasticity of the Arteries* | Contains the Patented Pyncogenol. |
| Stimulates Cell Growth and Healthy Tissue | Includes Patented SMART Composition |
| Reduces Fatty Deposits in Arteries | Contains Synergistic Amino Acids |
| Stimulates Natural Endorphinergic Healing Functions | Contains d-Ribose |

*These statements have not been evaluated by the Food and Drug Administration. This product is not intended to diagnose, treat, cure or prevent disease.

Stimulates Natural Endorphinergic Healing Functions contains d-Ribose

These statements have not been evaluated by the Food and Drug Administration. This product is not intended to diagnose, treat, cure or prevent disease.

Fifteen to 20 percent of adults in the United States have hypertension. The great majority of cases are presently undetected, untreated, or inadequately treated, and it is twice as life threatening if you do not know you have it. High blood pressure takes years to develop and up to 30 years to do its damage not just to your heart and arteries, but also to your kidneys, lungs, brain, and nervous system. Next to old age and obesity, high blood pressure is the most potent predictor of a shortened life span. Of the 60 million Americans who are hypertensive, 10 million or more may be on medication of questionable value or may be on medication of real danger. Current reports of the American Medical Association, The American Heart Association and the National Institutes of Health indicate that treating your high blood pressure with drugs in current use can reduce sex drive, produce accelerated aging of all the major organs (the heart, lungs, and kidneys) and can shorten life expectancy by 16 years. Moreover, fifty percent of all elderly patients on diuretics show severe potassium and magnesium deficiencies. Most high blood pressure medications interfere with normal brain function, decrease alertness and memory, and can cause premature senility symptoms in persons over 60 years of age. Finally, certain high blood pressure medications (e.g. Captopril, Vasotec, etc.) may worsen the quality of life for 30 to 40 percent of all individuals. Heart attacks can be caused in-part by the development of cholesterol and fatty deposits on the walls of the arteries. Lipoproteins are the sticky molecules that stick to artery walls that make up fatty deposits beside cholesterol particles. These molecules form a biological "adhesive tape" around the particles of fat and could lead to the clogging of blood vessels. L-Lysine and L-Proline prevent and neutralize the sticky particles and reduce clogging.

CARDIOPLEX provides a SMART composition which contains natural blood pressure lowering substances as well as herbs which enhance cognition. CARDIOPLEX contains the SMART composition of amino-acids, minerals, and vitamins (See Table 27).

TABLE 26

Supplement Facts
Serving Size: 1 Caplet
Servings Per Container: 90

| Amount per Serving | % Daily Value |
| --- | --- |
| SMART ™ Composition | + |
| l-Lysine 150 mg | + |
| l-Proline 150 mg | + |
| Huperzine 1 mg | + |
| Arctic Root Extract 25 mg | + |
| Standardized to 1.0% Rosavins, 0.25 mg. | |
| Standardized to 1.0% Salidrosides, 0.25 mg. | |
| Ganoderma Lucidum 750 mg. | + |
| Standardized to % of Isomer X | |
| d-Ribose 500 mg. | + |
| Co-Enzyme Q-10 10 mg | + |
| Pycnogenol 10 mg. | + |

+ Minimum Daily Requirements not established for this ingredient.
Important Notes:
Do not use this product in cases with PKU, if you are pregnant or nursing. If you are under the care of a physicians or taking medication consult your health professional before taking product. Do not exceed the recommended dose unless directed to do so by your health care professional. Do not use with other substances which cause drowsiness (such as alcohol). Take as directed and keep away from children.

TABLE 27

SMART ™ Blend Composition in CardioPlex ™ and Rationale for Use
(Amounts are for a daily dose of six Caplets)

| Ingredient | Amount | Restorative Action | Mechanism | Behavioral Change |
| --- | --- | --- | --- | --- |
| d-Phenylalanine | 750 mg. | Enkphalins | Enzyme Inhibition | Anti-Craving Anti-Depression |
| l-Phenylalanine | 750 mg. | Dopamine Norepinephrine | Precursor Loading | Reward Anti-Depression |
| l-Tyrosine | 900 mg. | Dopamine Norepinephrine | Precursor Loading | Reward Anti-Depression Anti-Stress |
| l-5-Hydroxytryptophan | 20 mg. | Serotonin | Precursor Loading | Anti-Craving Anti-Depression Anti-Insomnia |

TABLE 27-continued

SMART ™ Blend Composition in CardioPlex ™ and Rationale for Use
(Amounts are for a daily dose of six Caplets)

| Ingredient | Amount | Restorative Action | Mechanism | Behavioral Change |
|---|---|---|---|---|
| 1-Glutamine | 400 mg. | GABA | Precursor Loading | Anti-Craving Anti-Stress |
| Vitamin B Complex | | Neurotransmitter Synthesis | Enzyme Co-Factor in Neurotransmitter Synthesis | Facilitates Action of Neurotransmitter |
| Thiamin HCL | 100 mg. | Vitamin B | Enzyme Co-Factor in Neurotransmitter Synthesis | Facilitates Action of Neurotransmitter |
| Riboflavin | 15 mg. | Vitamin $B_7$ | Enzyme Co-Factor in Neurotransmitter Synthesis | Facilitates Action of Neurotransmitter |
| Niacinamide | 100 mg. | Vitamin $B_3$ | Enzyme Co-Factor in Neurotransmitter Synthesis | Facilitates Action of Neurotransmitter |
| Pantothenic Acid | 90 mg. | Vitamin $B_3$ | Enzyme Co-Factor in Neurotransmitter Synthesis | Facilitates Action of Neurotransmitter |
| Pyridoxal-5-phosphate | 20 mg. | Vitamin $B_2$ Active Metabolite | Promotes Gastrointestinal Absorption of Amino Acids | Facilitates Action of Neurotransmitter |
| Cyanocobalamin | 6 µg. | | | Facilitates Action of Neurotransmitter |
| Ascorbate (Calcium) | 600 mg. | Neurotransmitter Synthesis | Enzyme Co-Factor | Facilitates Action of Neurotransmitter |
| Folic Acid | 400 µg. | Neurotransmitter Synthesis | Enzyme Co-Factor | Facilitates Action of Neurotransmitter |
| Zinc (Chelate) | 30 mg. | Neurotransmitter Synthesis | Enzyme Co-Factor | Facilitates Action of Neurotransmitter |
| Calcium (Chelate) | 1500 mg. | Neurotransmitter Modulator | Regulates Neuro-transmitter Release | Facilitates Action of Neurotransmitter |
| Magnesium (Oxide) | 150 mg. | Neurotransmitter Modulator | Regulates Neuro-transmitter Release | Calmative |
| Chromium Picolinate | 1500 µg. | Neurotransmitter Modulator | Enhances Amino Acid Brain Penetration | Facilitates Action of Neurotransmitter |

TABLE 28

Additional CardioPlex ™ Ingredients*

| | |
|---|---|
| Vitamin C (Ascorbic Acid) | Vitamin C salt with varying molecular components to enhance overall C utilization |
| Vitamin C | A unique, essential vitamin used by the body to produce the collagen molecules necessary for proper cardiovascular function |
| Vitamin E | Important antioxidant that improves circulation, helps tissue repair, promotes normal clotting and healing, and reduces scarring from some wounds. |
| Vitamin A | Important Antioxidant essential for new cell growth and health tissue development. Beta-Carotene is a pro-vitamin which the body converts into Vitamin A as the body finds it necessary. |
| Vitamin $B_1$ | Enhances circulation and assists in the production hydrochloric acid, blood formation, and carbohydrate metabolism. |
| Vitamin $B_2$ | Necessary for red blood cell formation, anti-body production, cell respiration and growth; aids in the metabolism of carbohydrates, fats, and proteins. |
| Vitamin $B_3$ | Needed for proper circulation, and healthy skin; aids in the metabolism of carbohydrates, fats and proteins. |
| Vitamin $B_5$ | Assists in vitamin utilization and helps convert carbohydrates, fats, and proteins to energy. |
| Vitamin $B_6$ | Involved in more bodily functions than any other nutrient. Needed in the production of hydrochloric acid and in the absorption of fats and proteins. Aids in maintaining sodium and potassium balance. Enhances and promotes red blood cell formation. |
| Vitamin $B_{12}$ | Promotes red blood cell formation and cellular longevity. Required for proper digestion, absorption of foods, protein synthesis, and metabolism of fats and carbohydrates |
| Vitamin D | Important for strong bones. Necessary for phosphorus and calcium absorption and utilization. |
| Folic Acid | Needed for energy production and the formation of red blood cells. Important for red blood cell division and replication, and is involved in protein metabolism. |
| Biotin | Aids in cell growth, fatty acid production, metabolism of fats, carbohydrates, and proteins, and utilization of the B complex vitamins |
| Calcium | Importance in the maintenance of regular heartbeat and the transmission of nerve impulses, needed for muscle growth, the formation of strong bones and teeth and is essential in blood clotting. |
| Magnesium | Vital to enzyme activity, helps in maintaining stable blood pressure and converting blood sugar to energy, assists in calcium and potassium intake. |

TABLE 28-continued

Additional CardioPlex ™ Ingredients*

| | |
|---|---|
| Potassium | Important for healthy nervous system, regular heartbeat, and assists in maintaining stable blood pressure. |
| Phosphate | Required for cell growth, contraction of the heart muscle, and kidney function. Assists the body in utilization of vitamins and conversion of food into energy. |
| Zinc | Required for protein synthesis, collagen formation, and appears necessary for tissue repair. |
| Manganese | Needed for protein and fat metabolism, healthy nerves, blood sugar regulation, and is needed for energy production. |
| Copper | Aids in the formation of bone hemoglobin and red blood cells. Works in balance with zinc and vitamin C to form elastin. Involved in the healing process and energy production. |
| Selenium | Antioxidant needed for pancreatic function and tissue elasticity. |
| Chromium | Involved in the metabolism of glucose for energy and in the synthesis of fats, cholesterol, and proteins. |
| Pycnogenol | Antioxidant made from the bark of European Marine Pine. This rare patented agent has been thoroughly studied and heralded for its power to block free radical damage and its ability to be absorbed quickly and enhance activity of other antioxidants. |
| i-Proline and i-Lysine | Amino acids that have been shown in laboratory studies to limit and reverse fatty tissue development in artery tissue. |
| i-Camitine, i-Arginine, i-Cysteine | Amino acids required for optimum cell function. |
| Inositol | Helps maintain elasticity of the arteries and helps remove fats from the liver. |
| Coenzyme Q-10 | Vital cell fuel and catalyst in the creation of energy. |
| Molybdenum | Necessary for the function of several enzymes and for iron metabolism. |

*SOURCE: REXALL SHOWCASE INTERNATIONAL

IMUNOPRO ™

IMUNOPRO consists of amino-acids, trace metals, minerals, vitamins, and herbals designed to promote a naturally powerful defense mechanism known as your immune response. It is: well known that certain factors play a role in the immune response which include genetics, nutrition, stress, and other life-style changes. (See Table 31).

The common cold is the most frequent infection in all age groups in the United States. About $5.5 million are spent annually on colds in the United States. Persons have more than one billion colds each year, of which 110 million are disabling: the result is about 300 million days of restricted activity, about 60 million los t days of school and about 50 million work day. Although it is well recognized that most colds are caused by rhinoviruses, at least S37.5 million worth of antibiotics were prescribed for the common cold in 1994 in the United States. More than 100 distinct rhinoviruses exist, making it impossible to produce a useful vaccine. Therefore, leaders in the pharmaceutical industry have looked more recently to the nutrition as a possible answer to this health issue. However, this has not been an easy task, for example review of six major studies on vitamin C supplementation gave no evidence that high dose vitamin C supplementation decrease the incidence of the common cold. In contrast, a look at the trace metal zinc lead to more definitive conclusions.

In 1974 it was reported that zinc ions inhibit rhinovirus replication. A review of published clinical studies on the use of zinc lozenges in colds found four studies that reported zinc salts to be beneficial and four were did not do so. One important note is that the four studies that did not show benefit s used zinc lozenges with substances known to complex zinc ions, where as the four studies with positive results used an ionizable form of zinc without such substances. Zinc ions have other benefits that may shorten the severity and duration of non-viral symptoms associated with the common cold. In 1998, the CyberPharm scientist, Kenneth Blum, in conjunction with others in a randomized, double-masked, placebo controlled study demonstrated the effectiveness of zinc acetate lozenges on common cold symptoms in allergy tested subjects. Zinc acetate significantly shortened the duration of common cold symptoms and re3lieved symptoms associated with allergies. Moreover, zinc is an essential element in immune system functions. The inhibitory effect of zinc on histamine release from mast cells is attributed to its action on the stabilization of mast cell membranes.

Opioids (exogenous opiates and endogenous opioid peptides) have been found to modulate the immune system by regulating the function of immunocompetent cells. Several laboratories have indicated that opioids can operate as cytokinins, the principal communication signals of the immune system. Chronic activation of the endogenous opioid system augments the natural immune response. One important method to increase the activity of endogenous opioid peptides is to use D-amino acids, like D-phenylalanine, which inhibits the neuropeptidases known to breakdown the enkephalins, endorphins, and dynorphins in the brain. This in turn would enhance the natural immune response.

Two other important aspects that relate to the design of IMUNOPRO is that it is well know that catecholamines, like dopamine, seem to play an important role in the regulation of the immune function, both after chronic exercise and emotional stress. The second important aspect relates to the finding that the zinc ion is a potent inhibitor of one of the opioid peptide degrading enzymes, specifically aminotripepidase.

Experimental data available today strongly indicate that various types of physiological stressors, including physical exercise and emotional stress, can influence immune function. It is noteworthy, that natural immunity is strongly influenced by chronic exercise, and this regulation includes interaction between the nervous, endocrine, and immune systems as well as a positive effect on the endogenous opioids.

Moreover certain herbs are believed to promote immune system health and may stimulate the production and action of white blood cells, which are critical to the body's ability to promote cell repair and health.

IMUNOPRO also consists of herbs know to have an anti-oxidant and immune-stimulatory action including curcumin the active ingredient of spice tumeric which protects the body from free-radical damage. The product also features the following herbs: cat's claw, garlic, elderbery, *ganoderma lucidum*, astralgus, and echinacea, which are believed to promote immune system health.

TABLE 29

| BENEFITS | FEATURES |
|---|---|
| Increases the Endorphinergic System* | Includes Patented SMART Composition. |
| Blocks the Aminopeptidase Enzymes* | Includes d-phenylalanine to Boost Endorphins. |

TABLE 29-continued

| BENEFITS | FEATURES |
|---|---|
| Enhances the Immune System* | Contains the Novel Zinc-dl-phenylalanine Complex. |
| Protects Against Free Radical Damage* | Consists of Zinc Acetate |
| Has Anti-Oxidant Properties | Contains Curcumin of Tumeric |
| Releases Brain Dopamine and Norepinephrine | Provides the Immune Stimulant Echinacea |
| Has Anti-Viral Activity | Includes Other Herbal Immune Stimulants |

*These statements have not been evaluated by the Food and Drug Administration. This product is not intended to diagnose, treat, cure or prevent disease.

The body protects itself from infectious organisms and other harmful invaders through an elaborate network of safeguards called the host defense system. This system has three lines of defense: physical, the inflammatory response, and the immune response. Physical barriers, such as the skin and mucous membranes, prevent most organisms from invading the body. Organisms tat penetrate this first barrier simultaneously trigger the inflammatory and immune response. Both responses involve stem cells in the bone marrow that form blood cells. Four structures in the body make up the immune system: lymph nodes, thymus, spleen, and tonsils.

Certain cells have the ability to distinguish between foreign matter and what belongs to the body. When foreign substances invade the body, two types of immune responses are possible cell mediated and humoral immunity. In cell-mediated immunity, T cells respond directly to antigens (foreign substances such as bacteria or toxins that induce antibody formations). This response involves destruction of target cells—such as virus-infected cells and even cancer cells—through the secretion of lymphokines (lymph protein). Eighty percent of blood cells are T cells. In humoral immunity B cells act in a different way that T cells are responsible for humoral or immunoglobulin-mediated immunity. B cells originate in the bone marrow and mature into plasma cells that produce antibodies (immunoglobin molecules that interact with a specific antigen). Antibodies destroy bacteria and viruses, thereby preventing them from entering host cells. There are still other cells—not lymphocytes—called phagocytes, or "cell eaters", that digest microbes. IMUNMOPRO is designed to combine amino acids, vitamins, and minerals which naturally stimulate the immune system response via enhancement of the opioid peptide and the catecholamine systems as well as providing herbs that can be a powerful aid in supporting the body's defense against infections and when combined with good nutrition and exercise leads to a healthy lifestye.

Nutritional Information

TABLE 30

| Supplement Facts Serving Size: 1 Caplet Servings Per Container: 90 | |
|---|---|
| Amount per Serving | % Daily Value |
| SMART ™ Composition | + |
| Zinc-dl-Phenylalanine 100 mg | + |
| Zinc Acetate 10 mg | + |
| Tumeric Rhizome Extract 100 mg | + |
| Standardized to 85.0% Curcuminoids, 95 mg. | |
| Echinacea Purpurea Extract 100 mg. | + |
| Standardized to 4% Phenolic Compounds, 4 mg. | |
| ImunoPro Blend 200 mg. | + |
| Garlic Bulb. | + |
| Astragalus Root | + |
| Elderberry Fruit | + |
| Ganoderma Lucidum | + |
| Cats Claw Bark | + |

+ Minimum Daily Requirements not established for this ingredient.

Important Notes:

Do not use this product in cases with PKU, if you are pregnant or nursing. If you are under the care of a physician or taking an MAO-inhibitor type anti-depressant medication or a blood thinner medication consult your health professional before taking product. Do not exceed the recommended dose unless directed to do so by your health care professional. Do not use continuously for more than eight weeks. Not recommended for individuals with autoimmune disorders.

IMUNOPRO contains the SMART composition of amino-acids, minerals, and vitamins (See Table 32).

TABLE 31

Composition of ImunoPro ™ and Rationale for Use
(Amounts are for a daily dose of six Caplets)

| Ingredient | Amount | Restorative Action | Mechanism | Behavioral Change |
|---|---|---|---|---|
| d-Phenylalanine | 750 mg. | Enkephalins | Enzyme Inhibition | Anti-Craving Anti-Depression |
| l-Phenylalanine | 750 mg. | Dopamine Norepinephrine | Precursor Loading | Reward Anti-Depression |
| l-Tyrosine | 900 mg. | Dopamine Norepinephrine | Precursor Loading | Reward Anti-Depression Anti-Stress |
| l-5-Hydroxytryptophan | 20 mg. | Serotonin | Precursor Loading | Anti-Craving Anti-Depression Anti-Insomnia |
| l-Glutamine | 300 mg. | GABA | Precursor Loading | Anti-Craving Anti-Stress |
| Vitamin B Complex | | Neurotransmitter Synthesis | Enzyme Co-Factor in Neurotransmitter Synthesis | Facilitates Action of Neurotransmitter |

TABLE 31-continued

Composition of ImunoPro ™ and Rationale for Use
(Amounts are for a daily dose of six Caplets)

| Ingredient | Amount | Restorative Action | Mechanism | Behavioral Change |
|---|---|---|---|---|
| Thiamin HCL | 100 Mg. | Vitamin B | Enzyme Co-Factor in Neurotransmitter Synthesis | Facilitates Action of Neurotransmitter |
| Riboflavin | 15 mg. | Vitamin $B_7$ | Enzyme Co-Factor in Neurotransmitter Synthesis | Facilitates Action of Neurotransmitter |
| Niacinamide | 100 mg. | Vitamin $B_3$ | Enzyme Co-Factor in Neurotransmitter Synthesis | Facilitates Action of Neurotransmitter |
| Pantothenic Acid | 90 mg. | Vitamin $B_3$ | Enzyme Co-Factor in Neurotransmitter Synthesis | Facilitates Action of Neurotransmitter |
| Pyridoxal-5-phosphate | 20 mg. | Vitamin $B_2$ Active Metabolite | Promotes Gatrointestinal Absorption of Amino Acids | Facilitates Action of Neurotransmitter |
| Cyanocobalamin | 6 $\mu$g. | | | Facilitates Action of Neurotransmitter |
| Ascorbate (Calcium) | 600 mg. | Neurotransmitter Synthesis | Enzyme Co-Factor | Facilitates Action of Neurotransmitter |
| Folic Acid | 400 $\mu$g. | Neurotransmitter Synthesis | Enzyme Co-Factor | Facilitates Action of Neurotransmitter |
| Zinc (Chelate) | 30 mg. | Neurotransmitter Synthesis | Enzyme Co-Factor | Facilitates Action of Neurotransmitter |
| Calcium (Chelate) | 150 mg. | Neurotransmitter Modulator | Regulate Neurotransmitter Release | Facilitates Action of Neurotransmitter |
| Magnesium (Oxide) | 150 mg. | Neurotransmitter Modulator | Regulate Neurotransmitter Release | Calmative |
| Chromium Picolinate | 1500 $\mu$g. | Neurotransmitter Modulator | Enhances Amino Acid Brain Penetration | Facilitates Action of Neurotransmitter |

TABLE 32

Summary of Studies of the Human $D_2$ Receptor Gene and the Deficiency Syndrome Behavior-Obesity

| Investigation | Polymorphic Loci | Type Study | Population Studied | Parameter | Results | Comment |
|---|---|---|---|---|---|---|
| Blum, et al. (1999)[1] | $A_1$ | Association | Morbidly Obese Males and Females | Percent Body Fat | Positive | DRD2 $A_1$ accounted for 45.9 percent of the variance associated with percent body fat as compared with "super controls". |
| Blum, et al. (1999)[2] | $A_1$ | Association | Morbidly Obese Males and Females administered 400 mcg of CrP/day | Response to Change in Body Composition | Positive | Change in fat weight, change in body weight, percent change in weight, and body weight change in kgms all were significant in $A_2/A_2$ group and non-significant in the $A_1/A_2$ and $A_1/A_1$ carriers. |
| Blum, et al. (1996)[3] | $A_1$ | Association | Obese Patients With A Body Mass Index Over 25. Risk factors include Co-morbid Substance Abuse Disorder. | Obesity | Positive | Association of $DRD_2A_1$ allele and patients with a Body Mass Index over 25. Significant increase of $A_1$ percent prevalence with increasing severity of substance dependence. |
| Blum, et al. (1994)[4] | $A_1$ | Association | Obese and control probands | Obesity and electrophysiology | Positive | $A_1$ allele was present in 25 percent of probands having zero risk factors compared to 66 percent of obese subjects with risk factors. This work confirms the association of P300 abnormalities and the $A_1$ allele in obesity. |
| Comings, et al. (1996)[5] | $A_1$ | Association | Young Morbidly Obese females | Obesity | Positive | OB and DRD2 genes were additive in their contribution to overall variance in BMI. These two genes accounted for 22.8 percent of BMI variance. |
| Comings, et al. (1993)[6] | $DRD_2$ Haplotypes Intron 6-Exon 7 | Association | Undifferentiated Overweight Subjects And Controls | Obesity | Positive | Undifferentiated obese patients in terms of macro-selection associated with haplotype IV. |

TABLE 32-continued

Summary of Studies of the Human $D_2$ Receptor Gene and the
Deficiency Syndrome Behavior-Obesity

| Investigation | Polymorphic Loci | Type Study | Population Studied | Parameter | Results | Comment |
|---|---|---|---|---|---|---|
| Noble, et al. (1994)[7] | $A_1$ | Association | Characterized Overweight Obese Patients And Non-Obese Controls And Associated Risk Factors | Obesity/ carbohydrate bingeing | Positive | Prevalence of $A_1$ allele increases in obese patients compared to controls. While there was no association with cardiovascular factors, a positive association was found with parental alcoholism and carbohydrate bingeing |

[1] Blum K, Kaats G, Davis K, Sherman M, Eisenberg A, Cull J G, Chen T J H, Wood R, Braverman E, Bucci L, Quilici-Timmcke J, Comings D E. The Dopamine $D_2$ Receptor $A_1$ Allele is a Major Gene Variant in Morbid Obesity: Strong Association With Percent Body Fat. Submitted to Molecular Psychiatry.
[2] Blum K, Kaats G, Eisenbery A, Sherman M, Davis K, Comings D E, Cull J G, Chen T H J, Wood R, Bucci L, Wise J A, Braverman E R, and Pullin D. Chromium Picolinate Induces Changes in Body Composition as a Function of the Taq1 Dopamine $D_2$ Receptor $A_1$ Alleles. Submitted to Journal of The American College of Nutrition.
[3] Blum K, Braverman E R, Wood R C, Gill J, Li C, Chen T J H, Taub M, Montgomery A R, Cull J G, and Sheridan P J. 1996. Increased prevalence of the Taq1 A1 allele of the dopamine receptor gene in obesity with comorbid substance use disorder. Pharmacogenomics 6:297–305.
[4] Blum K, Braverman E R, Wood R, Sheridan P J. DRD2 A1 Allele and P300 abnormalities in obesity [Abstract]. Presented at the American Society of Human Genetics, Montreal, Canada. October 8th, American Journal of Human Genetics, 1994.
[5] Comings D E, Gade R, MacMurray J P, Muhleman D, Johnson P, Varde R, and Peters W R. 1996. Genetic variants of the human obesity (OB) gene: association with body mass index in young women psychiatric symptoms, and interaction with the dopamine $D_2$ receptor gene. Molecular Psychiatry 1:325–335.
[6] Comings D E, Flanagan S D, Diaz G, Muhlman D, Knelt E, and Gysin R. 1993. The dopamine $D_2$ receptor as a major gene in obesity and height. Biochemical Medicine and Metabolic Biology 50:176–185.
[7] Noble E P, Noble R E, Ritchie T, Syndulko K, St. jeor S C, Fitch R J, Brunner R L, and Sparkes R S. 1994. $D_2$ dopamine receptor gene and obesity. International Journal of Eating Disorders 15:205–217.

OBGENEMAP is the New Dopaminergic Genotypic Assessment for Obesity due to Carbohydrate Binging is now available. As a result of dramatic new findings in Reward Deficiency Syndrome Behaviors, CyberPharm, Inc. is pleased to offer the new Dopamine Receptor Gene DRD2 genotype report for genetic susceptibility to Obesity Due to Carbohydrate Binging. Genetic research reports (See Table 32):

A strong genetic correlation between variants of the dopamine D2 receptor gene, a gene which regulates the protein (receptors) involved in the reward centers of the brain and obesity, has been reported by several independent investigators.

Dopamine D2 receptor densities are lower in brain tissue obtained from patients carrying the A1 Bi and Intron6-Exon7 Haplotypes of the DRD2 gene. Similar reduced DRD2 densities have bee n found in alcohol preferring rodents compared to alcohol-non-preferring inbred animals.

Variants of the DRD2 gene has been correlated with increased risk of carbohydrate binging, obesity, attention-deficit/hyperactivity (ADH D), and Tourettes Disorder.

The association of the variants of the DRD2 gene with risk in developing compulsive diseases has been reported.

Results of independent studies suggest that individuals with two copies of the A1 allele are much more likely to develop one of the Reward Deficiency Syndrome behaviors than those who have one or none. The number of receptors are more greatly reduced in individuals with two copies than in those who have one or none.

Researchers report that vulnerability to obesity, carbohydrate binging, and food seeking behavior is likely to be the result of multiple factors and is polygenic, of which the DRD2 is one.

The A1 allele associated with almost 70 percent of deceased severe alcoholics. This value is highly confirmatory of the computed Bayes Theorem value to measure the predictive power of the A1 allele in obesity due to carbohydrate binging which is 74 percent.

Studies demonstrate that abnormal dopaminergic function results in abnormal carbohydrate seeking behavior. The D2 receptors are profoundly involved.

Test Results and Test Interpretation

The DRD2 dopamine receptor gene is evaluated by the DNA Based Multi-Plex OBGeneMap. The report specifies the following genotypes with greater than 99% accuracy:

DRD2 A1/A1
A1/A2
A2/A2

Interpretations of the genotype are provided in terms of offering confirmatory diagnostic data for the Reward Deficiency Syndrome behavior of obesity due to carbohydrate binging. Reports provide suggested therapeutic options.

This genetic diagnostic test requires no special handling or shipping. The tissue gathering aspects of the test consist of a non-invasive buccal swab. The consumer is instructed to "swab" the inside of the cheeks. The swabs then are placed in the provided mailer and shipped back to our laboratory for analysis and reporting.

SUMMARY OF INVENTION

An important aspect of the present invention is a kit comprising a buccal swab for obtaining a subject's DNA sample suitable for analysis of alleles associated with signal-transmitter production, reception or catabolism; and at least one composition comprising at least one of: a signal-transmitter precursor, an enhancer of precursor uptake, and an inhibitor of neurotransmitter reuptake or signal-transmitter catabolism; wherein allelic analysis predicts a likelihood of positive effects of a subjects intake of one or more components of the composition in effective amounts.

In an important aspect, the enhancer is a chromium salt, for example chromium nicotinate or chromium picolinate. Such chromium enhances certain neurotransmitter precursor uptake. In certain important aspects, the present invention involves a signal transmitter which includes' neurotransmitters as a subcategory. Other signal transmitters may be peptide like substances or hormones of various sorts. (Although a preferred signal transmitter is a neurotransmitter). In certain cases the inhibitor of the present invention may be an inhibitor of neurotransmitter reuptake or of various signal transmitter catabolisms. The buccal swab of the present invention is basically a method for a subject to obtain a DNA sample from the subjects oral cavity and send this DNA sample to an analytical lab where certain alleles may be determined. One preferred inhibitor of signal transmitter catabolism is D phenylanine or as it exists in DL phenylanine. Certain signal transmitters, in addition to being neurotransmitters, peptidyl transmitters or peptidyl opiates, may be agents such as nitric oxide or other secondary intercellular messengers.

In an important aspect of the present invention alleles are obtained from DNA samples originating from the subjects buccal swab. The alleles to be analyzed include alleles from the following genes: DAT1 (dopamine transporter), dopamine-beta-hydroxylase, dopamine D1 receptor, dopamine D2 receptor, dopamine D3 receptor, dopamine D4 receptor, dopamine D5 receptor, serotonin HTT, serotonin HTRIA, serotonin TDO2, adrenergic ADRA2A, adrenergic ADRA2C, adrenergic NET, catecholamine metabolizing MAOA, catecholamine metabolizing COMT, GABA-GABRA3, GABA-GABRB3, Canabinoid CNR1, NMDA Receptor NUDAR1, Nicotinic Cholinergic (CHRNA4), enkephalin (PENK), and Adrenergic Receptor (AR).

A kit of the present invention may also include, in addition to a buccal swab, the following:

a) an opiate destruction-inhibiting amount of at least one substance which inhibits the enzymatic destruction of a neuropeptidyl opiate, said substance being selected from the group consisting of amino acids, peptides, and structural analogues or derivatives thereof;

b) a neurotransmitter synthesis-promoting amount of at least one neurotransmitter precursor selected from the group consisting of dopamine precursors L-Tyr, L-Phe and L-dopa, serotonin precursors L-Trp and 5-hydroxytryptophan, and gamma amino butyric acid (GABA) precursors L-glutamine, L-glutamic acid, and L-glutamate; and c) a tryptophan concentration enhancing amount of chromium picolinate or chromium nicotinate, the amount of said substance and said neurotransmitter precursor and said chromium compound being effective in reducing the subject's RDS behaviors.

An important aspect of the present invention, a tryptophan concentration-enhancing amount of chromium nicotinate or chromium picolinate may be present. This combination now being effective in preventing or reducing a subjects unwanted weight or other RDS behaviors, such as attention deficits disorder, intentional processing or memory deficiency. Further RDS behaviors may include any in the group existing of SUD, Obesity, Smoking, Tourettes Syndrome, ADHD, Schizoid/Avoidant Behavior, Aggression, Posttraumatic stress syndrome, PMS or tobacco use. In certain aspects, composition of the present invention may include a daily dietary composition comprising 32 to 10,000 mg DL-phenylalanine, 5 to 5,000 mg L-tryptophan, 3 to 30,000 mg L-glutamine, and the composition further comprises 1–300 mg pyridoxal-5'-phosphate. When the term excess weight is involved, it is understood that this indicates obesity. In a preferred aspect, the kit involves a composition that comprises a daily dietary consumption of about 460 mg DL-phenylalanine, 25 mg L-tryptophan, 25 mg L-glutamine, and the mixture further comprises 5 mg pyridoxal-5'-phosphate. Allelic analysis may be confirmed by observation of a family history of certain RDS behaviors, this involving or confirming an improved likelihood for successful treatment by consumption of the subject composition in the kit. Various other RDS behaviors such as binge eating and cravings for various sensations are also a subject of the present invention.

In an important aspect of the present invention analysis of alleles are involved such alleles may be, for example $D_2$ TaqI A1, B1, C1 or exon 6–7 haplotype HTR2A-C allele homozygous OB-homozygosity for <208 BP alleles of 1875 dinucleotide repeat polymorphism human chromosome 2 microsatellite polymorphism, APO-D-TaqI 2.2 or 2.7 BP, or OB gene D7S 1875. One most important allele of the present invention is the DRD2A1 allele. In one possible embodiment of the present invention, various key ingredients of the composition may be contained in cyclodextrin, particularly where an interveineous or bolus injection might be part of administrating the composition of the present invention. In certain other aspects, consumption of the composition as described in the kit may be advised when the subject has at least one of the following alleles: D1 (homozygosity of Dde A1) D2 (TaqI A1) D4 (VNTR 2) D5 (dinucleotide 13 alleles range 135–159 BP) DAT1 VNTR (10/10) DβH (TaqI B1 allele). This indicating an improved likelihood for a successful response to the composition parenterally or enterally administered.

Other aspects of RDS behavior include Autism, Tourette's Syndrome or ADHD. In an important aspect, the addition of effect amounts of rhodiola or huberzine add an important aspect to the composition of the present invention. Other RDS behaviors include Pathological gambling and wherein the presence in a subject of at least one of the following alleles: D (homozygosity of Dde A), D (Taq A, B, C), indicates an improved likelihood for a successful response. Such behaviors may also include pathological violence, Schizoid/Avoidant (SAB), Aggression, Anger, Hostility, or Posttraumatic Stress Disorders, wherein the presence in the subject of at least one of the following alleles D (Taq A, B, C, exon), DAT (VNTR/), mNOSIa-homozygosity for ≦ BP allele indicates an improved likelihood for a successful response. In certain cases, the RDS behavior may be PMS wherein the presence of at least one of the following alleles DAT1 VNTR (10/10) $D_2$ TaqI A1, B1, C1, exon $^{6-7}$ haplotype, or alleles from the DRD1, DRD2, DRD4, HTT, HTRIA, TDO2, DβH, MAO, COMT, GABRAB, GABRB3, PENk, ADRA2A or ADRA2C genes indicates an improved likelihood for a successful response. Substance abuse disorder; is also an important RDS behavior, potentially treated by the by the present invention.

In another important embodiment, the alleles being detected indicate at least one RDS behavior, and in this case the allele is at least one of DRD1, DRD2, DRD3, DRD4, DRD5, DAT1, MITT, HTRIA, TDO2, DBH, ADRA2A, ADRA2C, NET, MAOA, COMT, GABRA3, GABRB3, CNR1, CNRA4, NMDAR1, PENK, AR, CR", HTRIDβ, HTR2A, HTR2C, interferon-γ, CD8A, or PS1 genes. Various other RDS behaviors are still an aspect of the present invention. These behaviors include mania, OCD, sexual, sleep, grade school behavior, gambling, learning, inattention, ADHD, ADDR, impulsivity, MDE, CD, hyperactivity, phobia, schizoid behavior, general anxiety, somatization, drugs, IV drugs, read, ODD, tics, alcohol, or tobacco use. In an important aspect, the allele being analyzed as pointing to certain RDS behaviors is the ventr polymorphism of the maoa gene as stated in claim 29. Such RDS behavior may be schizoid or avoidant.

Most often important alleles of the present invention include $DRD_2$ gene $A_1$ allele, the $DAT_1$ gene, VNTR 10/10 allele, or the DβH gene $B_1$ allele. Another allele of significance is an increased number of $(AAT)_n$ triplet repeats in the CNR1 gene. Other aspects of the present invention involve the figment of RDS behavior that includes drug use, obesity, anxiety, depression, psychoses, hostility, paranoid ideation, obsessive-compulsive behavior, neuroticism and over-conscientiousness. In certain important aspects the kit of the present invention may involve analysis of an allele selected from the group consisting of an increased number of the D7S1873, D7S1875, D7S514 or D7S680 dinucleotide repeats in the OB gene. In an important aspect, the allele detecting is by determining the existence of the $D_2A1$ allele of the DRD2 gene and an allele selected from the group comprising the an increased number of the D7S1873, D7S1875, D7S514 or D7S680 dinucleotide repeats in the OB gene.

In 1999, the present inventor conceived of the idea to develop a novel approach to both diagnose and treat RDS and related behaviors via an integrated, systematic approach involving a number of non-obvious components interacting as a commercially produced kit. The kit consists of a non-invasive buccal swab to diagnose the DNA of a suspected RDS proband (a single or multiple genes); an RDS Diagnostic Inventory Scale; a neutraceutical formula consisting of two parts (the SMART Formula plus a specific herbal remedy for each known RDS subtype behavior, i.e. alcoholism, cocaine dependence, smoking behavior, carbohydrate binging, PMS, PMDD, PTSD, ADD, ADHD, pathological gambling, episodic dyscontrol, sexual addiction etc.)

The invention first provides a composition for the treatment of Reward Deficiency Syndrome (RDS) behaviors in a subject. In certain aspects, this composition includes at least one of the following components: an opiate destruction-inhibiting amount of at least one substance which inhibits the enzymatic destruction of a neuropeptidyl opiate, the substance being either amino acids, peptides, and structural analogues or derivatives thereof; a neurotransmitter synthesis-promoting amount of at least one neurotransmitter precursor, the neurotransmitter precursor being either a dopamine precursor such as L-Tyr, L-Phe and L-dopa, a serotonin precursor such as L-Trp and 5-hydroxytryptophan, or a gamma amino butyric acid (GABA) precursor such as L-glutamine, L-glutamic acid, and L-glutamate; a tryptophan concentration enhancing amount of chromium picolinate or chromium nicotinate; a compound that releases enkephaline, the enkephaline releaser being, but not limited to, a peptide, and preferably a D-amino acid containing peptide; or an opiate antagonist amount of at least one compound which blocks the effects of an opiate at either the delta, mu, kappa, sigma, or epsilon receptors. The type of enkephalinase inhibitors, the neurotransmitter precursor, opiate destruction-inhibiting substance, opiate antagonist, and/or the chromium compound, in addition to the compounds specifically listed above, are further described herein this application and are encompassed by this invention. In certain preferred aspects of the invention, the composition is used in preventing or reducing a subject's unwanted weight. In certain other aspects of the invention, the composition is preferably used in the treatment of Attention Deficits Disorder, attentional processing or memory. In this embodiment, for the treatment of Attention Deficits Disorder, Attention-Deficit-Hyperactivity Disorder (ADH D) attentional processing or memory, the composition more preferably includes a neurotransmitter synthesis promoting amount of at least one neurotransmitter promoting substance selected from the group Rhodila or Hubazine or any substance known to enhance the functional amount of the neurotransmitter. As used herein, "derivative" may refer to a chemically modified compound, and analog refers to a different compound that is similar properties or structure to the compound it is being compared.

In certain embodiments of the invention, this composition may be used in the treatment of all RDS related behaviors disclosed herein. RDS behaviors are those behaviors related to a chemical imbalance manifests itself as one or more behavioral disorders related to an individual's feeling of well-being with anxiety, anger or a craving for a substance. RDS behaviors include, alcoholism, SUD, smoking, BMI or obesity, pathological gambling, carbohydrate binging, axis 11 diagnosis, SAB, ADD/ADHD, CD, TS, family history of SUD, and Obesity.

The invention also provides a method of treating a subject for RDS behaviors, including but not limited to SUD, Obesity, Smoking, Tourettes Syndrome, ADHD, Schizoid/Avoidant Behavior, Aggression, Posttraumatic stress syndrome, PMS or tobacco use. RDS behaviors are not specifically limited to these disorders, as many types of sub-disorders are encompassed by these conditions. For example, Attention Deficit Hyperactivity Disorder (ADHD) may manifest itself as alcohol, drugs, obsessive compulsive behaviors, learning disorders, reading problems, gambling, manic symptoms, phobias, panic attacks, oppositional defiant behavior, conduct disorder, academic problems in grade school, smoking, sexual behaviors, schizoid, somatization, depression, sleep disorders, general anxiety, stuttering, and tics disorders. All these behaviors, and others described herein as associated with RDS behaviors or genes involved in the neurological pathways related to RDS, are included as RDS behaviors as part of this invention. Additionally, many of the clinical terms used herein for many specific disorders that are RDS disorders are found in the Quick Reference to the Diagnostic Criteria From DSM-IV, The American Psychiatric Association, Washington, D.C., 1994, 358 pages. Specific disorders whose definitions can be found in this reference, and their code numbers within the DSM-IV include Anxiety disorders, include Panic Disorder Without Agoraphobia, 300.01, Panic Disorder With Agoraphobia, 300.21, Agoraphobia Without History of Panic Disorder, 300.22, Specific Phobia, 300.29, Social Phobia, 300.23, Obsessive-Compulsive Disorder, 300.3, Posttraumatic Stress Disorder, 309.81, Acute Stress Disorder, 308.3, Generalized Anxiety Disorder, 300.02, Overanxious Disorder of Childhood, 300.02, Anxiety Disorder Due to [Indicate general medical condition], 293.89, Substance Induced Anxiety Disorder, 293.89, Anxiety Disorder NOS, 300.00; Attention Deficit and Disruptive Behavior Disorders, including Attention-Deficit/Hyperactivity Disorder, Predominately Inattentive Type, 314.00, Attention-Deficit/Hyperactivity Disorder, Predominately Hyperactivity-Impulsive Type, 314.01 Attention-Deficit/Hyperactivity Disorder, Combined Type, 314.01, Attention-Deficit/Hyperactivity Disorder NOS, 314.9, Conduct Disorder, 312.8 Oppositional Defiant Disorder, 313.81, Disruptive Behavior Disorder NOS, 312.9; Bipolar Disorders including Bipolar I Disorder, 296.0×, 296.40, 296.4×, 296.6×, 296.5×, and 296.7, Bipolar II. Disorder, 296.89, Cyclothymic Disorder, 301.13, Bipolar Disorder NOS, 296.80; Depressive Disorders including Major Depressive Disorder, Recurrent, 296.3, Dysthymic Disorder, 300.4, Depressive Disorder NOS, 311, Major Depressive Disorder, Single Episode, 296.2; Eating Disorders including Bulimia Nervosa, Nonpurging Type, 307.51, Bulimia Nervosa, Purging Type, 307.51, Anorexia Nervosa, 307.1, Eating Disorder NOS 307.50; Impulse Control Disorders including Intermittent Explosive Disorder, 312.34, Kleptomania, 312.32, Pyromania, 312.23, Pathological Gambling, 312.31, Trichotillomania, 312.39, Impulse Control Disorder NOS, 312.30; Personality Disorders including Antisocial Personality Disorder, 301.7, Avoidant Personality Disorder, 301.82, Obsessive-Compulsive Personality Disorder, 301.4, Schizoid Personality Disorder, 301.20; Schizophrenia including Paranoid Type, 295.30, Disorganized Type, 295.10, Catatonic Type, 295.20, Undifferentiated Type, 295.90, Residual Type, 295.60, Schizoaffective Disorder, 295.70, Schizophreniform Disorder, 295.40; Sleep Disorders including Primary Sleep Disorders such as Dyssomnias, which include Primary Insomnia 307.42, Primary Hypersomnia 307.44, Narcolepsy 347, Circadian Rhythm Sleep Disorder, 307.45, Dyssomnia NOS 307.47, Parasomnias which include Nightmare Disorder 307.47, Sleep Terror Disorder 307.46, Sleepwalking Disorder 307.46, Parasomnia NOS 307.47, Sleep Disorders Related to Another Mental Disorder which include insomnia related to [Indicate Axis I or Axis H disorder] 307.42, Hypersomnia related to [Indicate Axis I or Axis II disorder] 307.44, Other Sleep Disorders which include Sleep Disorder due to [Indicate the General Medical Condition] 780.xx, Substance Induced Sleep Disorder 78o.xx; Substance Use Disorders including Alcohol Related Disorders such as Alcohol-Induced Psychotic Disorder, with delusions, 291.5, Alcohol Abuse, 305.00, Alcohol Intoxication, 303.00, Alcohol Withdrawal, 291.8, Alcohol Intoxication Delirium, 291.0, Alcohol Withdrawal Delirium, 291.0, Alcohol-Induced Persisting Dementia, 291.2, Alcohol-Induced Persisting Amnestic Disorder, 291.1, Alcohol Dependence, 303.90, Alcohol-Induced Psychotic Disorder, with hallucinations, 291.3, Alcohol-Induced Mood Disorder, 291.8, Alcohol-Induced Anxiety Disorder, 291.8, Alcohol-Induced Sexual Dysfunction, 291.8, Alcohol-Induced Sleep Disorder, 291.8, Alcohol-Related Disorder NOS, 291.9, Alcohol Intoxication, 303.00, Alcohol Withdrawal, 291.8, Nicotine Related Disorders which include Nicotine Dependence, 305.10, Nicotine Withdrawal, 292.0, Nicotine-Related Disorder NOS, 292.9, Amphetamine Related Disorders which include Amphetamine Dependence, 304.40, Amphetamine Abuse, 305.70, Amphetamine Intoxication, 292.89, Amphetamine Withdrawal, 292.0, Amphetamine Intoxication Delirium, 292.81, Amphetamine-Induced Psychotic Disorder with delusions, 292.11, Amphetamine-Induced Psychotic Disorders with hallucinations, 292.12, Amphetamine-Induced Mood Disorder, 292.84, Amphetamine-Induced Anxiety Disorder, 292.89, Amphetamine-Induced Sexual Dysfunction, 292.89, Amphetamine-Induced Sleep Disorder, 292.89, Amphetamine Related Disorder NOS, 292.9, Amphetamine Intoxication, 292.89, Amphetamine Withdrawal, 292.0, *Cannabis* Related Disorders which include *Cannabis* Dependence, 304.30, *Cannabis* Abuse, 305.20, *Cannabis*. Intoxication, 292.89, *Cannabis* Intoxication Delirium, 292.81, *Cannabis*-Induced Psychotic Disorder, with delusions, 292.11, *Cannabis*-Induced Psychotic Disorder with hallucinations, 292.12, *Cannabis*-Induced Anxiety Disorder, 292.89, *Cannabis* Related Disorder NOS, 292.9, *Cannabis* Intoxication, 292.89, Cocaine Related Disorders which include Cocaine Dependence, 304.20, Cocaine Abuse, 305.60, Cocaine Intoxication, 292.89, Cocaine Withdrawal, 292.0, Cocaine Intoxication Delirium, 292.81, Cocaine-Induced Psychotic Disorder with delusions, 292.11, Cocaine-Induced Psychotic Disorders with hallucinations, 292.12, Cocaine-Induced. Mood Disorder, 292.84, Cocaine-Induced Anxiety Disorder, 292.89, Cocaine-Induced Sexual Dysfunction, 292.89, Cocaine-Induced Sleep Disorder, 292.89, Cocaine Related Disorder NOS, 292.9, Cocaine Intoxication, 292.89, Cocaine Withdrawal, 292.0; Hallucinogen Use Disorders which include Hallucinogen Dependence, 304.50, Hallucinogen Abuse, 305.30, Hallucinogen Intoxication, 292.89, Hallucinogen Withdrawal, 292.0, Hallucinogen Intoxication Delirium, 292.81, Hallucinogen-Induced Psychotic Disorder with delusions, 292.11, Hallucinogen-Induced Psychotic Disorders with hallucinations, 292.12, Hallucinogen-Induced Mood Disorder, 292.84, Hallucinogen-Induced Anxiety Disorder, 292.89, Hallucinogen-Induced Sexual Dysfunction, 292.89, Hallucinogen-Induced Sleep Disorder, 292.89, Hallucinogen Related Disorder NOS, 292.9, Hallucinogen Intoxication, 292.89, Hallucinogen Persisting Perception Disorder (Flashbacks), 292.89; Inhalant Related Disorders which include Inhalant Dependence, 304.60, Inhalant Abuse, 305.90, Inhalant Intoxication, 292.89, Inhalant Intoxication Delirium, 292.81, Inhalant-Induced Psychotic Disorder, with delusions, 292.11, Inhalant-Induced Psychotic Disorder with hallucinations, 292.12, Inhalant-Induced Anxiety Disorder, 292.89, Inhalant Related Disorder NOS, 292.9, Inhalant Intoxication, 292.89; Opioid Related Disorders which include Opioid Dependence, 304.00, Opioid Abuse, 305.50, Opioid Intoxication, 292.89, Opioid Intoxication Delirium, 292.81, Opioid-induced Psychotic Disorder, with delusions, 292.11, Opioid-Induced Psychotic Disorder with hallucinations, 292.12, Opioid-induced Anxiety Disorder, 292.89, Opioid Related Disorder NOS, 292.9, Opioid Intoxication, 292.89, Opioid Withdrawal, 292.0; Polysubstance Related Disorders which include Polysubstance Dependence, 304.80; Tic Disorders which include Tourettes Disorder, 307.23, Chronic Motor or Vocal Tic Disorder 307.22, Transient Tic Disorder 307.21, Tic Disorder NOS 307.20, Stuttering 307.0, Autistic Disorder, 299.00, and Somatization Disorder 300.81. Additionally, other RDS disorders are defined as would be known to one of skill in the art, such as Novelty Seeking, defined in (Clonigen et al., 1993). Other disorders, if not specifically defined herein, are the same as commonly known to one of skill in the art, including common abbreviations. The second part of the invention includes but not limited the following genes: DRD1, DRD2, DRD5, DATI, HTT HTR IA, TDO2, DBH, ADRA 2A, ADRA2C, NET, MAQA, COMT, GABRA3, GABRB3, CNRI, CNRA4, NMDAR1, PENK, AR, CRF, DRD3, DRD4. HTRIDI3, HTR2A, HTR2C, interferon-~y, CD8A, PSi, TDO2, HTT, APOE. The third part of the patent is to include an RDS Inventory Scale. The fourth part of the patent involves the SYNERGENE Neutralife product line and includes the following information which relates to the brain reward cascade, the Reward Deficiency Syndrome and both nutraceuticals.

DETAILED DESCRIPTION OF THE PREFERRED EMBODIMENTS

The following information forms an important basis of the invention. In an embodiment of the invention, each gene studied will be specified, and the survey will pinpoint the primary presenting problem which will dictate the type of neutraceutical to be employed. It is anticipated the diagnosis and treatment unit will consist of four parts: four swabs, one scale, a bottle of the RDS neutraceutical, and a selection of herbal or other remedies to ameliorate the specific RDS behavior which is the focus of attention.

The above references do not limit in any shape or form the type of swab, envelope, survey type, or type of bottles, or caplets, capsules, liquid, gums, powder, bars or any configuration, size standard to the art.

Allelic Diagnosis of Susceptibility to Compulsive Disorder

In an important embodiment, the present invention concerns a method for diagnosing and detecting compulsive disorder susceptibility of an individual. The method comprises initially obtaining a DNA sample of said individual and then determining the presence or absence of particular human D 2 receptor gene alleles in said sample. Detection of said alleles in the sample are indicative of predilection to compulsive disorder. A most preferred embodiment is to detect predisposition to impulsive, addictive, and compulsive disorders such as, but not limited to, alcoholism, obesity, smoking, polysubstanceabuse and drug addiction, particularly because said alleles have been found to be present in a majority of individuals clinically diagnosed with these compulsive disorders. The human D 2 receptor gene A1, Bi, and~haplotype I alleles are most preferably detected in said sample.

A preferred embodiment includes a four component unit or kit comprising of a. the gene test, b. an inventory scale, c. the SM ART formula, d. the SYNERGENE herbal formula. Also, in one form of the embodiment, the Kit would contain the forms as illustrated in Tables 1 through 3.

TABLE 1

Self Observation Scale

NAME:　　　　　　　　　　　　　　　　　　　　　　　AGE:　　　　DOB:　　　　SEX:
ADDRESS:　　　　　　　　　　　　　　　　　　　　　TELEPHONE:　　FAX:
　　　　　　　　　　　　　　　　　　　　　　　　　　　E-MAIL:　　　DATE:

PHYSICAL CHARACTERISTICS: WEIGHT　　　HEIGHT　　　BLOOD PRESSURE　　/　　RESTING HEART RATE

MARITAL STATUS: MARRIED ___ DIVORCED ___ WIDOWED ___ SEPARATED ___ INDICATE HOW LONG:

EDUCATION (CHECK HIGHEST LEVEL): HIGH SCHOOL DIPLOMA ___ SOME COLLEGE ___ BUSINESS OR TECHNICAL SCHOOL ___ COLLEGE DEGREE ___ OR DOCTORATE ___

IN THE BOXES BELOW PLEASE CHECK ALL OF THE DESCRIPTIONS WHICH APPLY,

THE BOXES RANGE FROM "1" INDICATING NONE OR NON-APPLICABLE UP TO "5" INDICATING A PROBLEM OF SEVERE INTENSITY.

| BEHAVIORS WHICH NOW APPLY OR HAVE APPLIED TO YOU | | | | | | BEHAVIORS WHICH APPLY OR HAVE APPLIED TO MEMBERS OF YOUR FAMILY | | | | | |
|---|---|---|---|---|---|---|---|---|---|---|---|
| | 1 | 2 | 3 | 4 | 5 | | 1 | 2 | 3 | 4 | 5 |
| Alcoholism | ___ | ___ | ___ | ___ | ___ | Alcoholism | ___ | ___ | ___ | ___ | ___ |
| Crack/Cocaine Addiction | ___ | ___ | ___ | ___ | ___ | Crack/Cocaine Addiction | ___ | ___ | ___ | ___ | ___ |
| Carbohydrate Bingeing | ___ | ___ | ___ | ___ | ___ | Carbohydrate Bingeing | ___ | ___ | ___ | ___ | ___ |
| Nicotine Use or Abuse | ___ | ___ | ___ | ___ | ___ | Nicotine Use or Abuse | ___ | ___ | ___ | ___ | ___ |
| Hyperactivity | ___ | ___ | ___ | ___ | ___ | Hyperactivity | ___ | ___ | ___ | ___ | ___ |
| Sexual Hyperactivity | ___ | ___ | ___ | ___ | ___ | Sexual Hyperactivity | ___ | ___ | ___ | ___ | ___ |
| Pathological Violence | ___ | ___ | ___ | ___ | ___ | Pathological Violence | ___ | ___ | ___ | ___ | ___ |
| PATHOLOGICAL GAMBLING | ___ | ___ | ___ | ___ | ___ | PATHOLOGICAL GAMBLING | ___ | ___ | ___ | ___ | ___ |
| Tourette's Disorder | ___ | ___ | ___ | ___ | ___ | Tourette's Disorder | ___ | ___ | ___ | ___ | ___ |
| Autism | ___ | ___ | ___ | ___ | ___ | Autism | ___ | ___ | ___ | ___ | ___ |

I chose to buy this product because of my:

Alcoholism or Problem Drinking ___, Crack/Cocaine Addiction ___, Carbohydrate Bingeing ___, Smoking History ___, Hyperactivity ___, Sexual Hyperactivity ___, Pathological Violence ___, Pathological Gambling ___, Tourette's Disorder ___

TABLE 2

| Read each item carefully, then check the following boxes to describe yourself | none of the time | a little of the time | some of the time | a good part of the time | almost all of the time |
|---|---|---|---|---|---|
| I crave a substance or activity or behavior. | | | | | |
| I use substances such as food, alcohol, etc. to change my mood or to relax. | | | | | |
| To adjust to stress or problems, I pretend nothing is wrong: I ignore the problem. | | | | | |
| I abuse coffee, aspirin, or medications to try to cope better. | | | | | |
| I have a judgmental attitude; I complain and criticize. | | | | | |
| EMOTIONAL | well below average | below average | average | above average | well above average |
| My coping skills are: | | | | | |
| My resilience (ability to "bounce back" during times of stress or trouble) is: | | | | | |
| My desire or need to control others or situations is: | | | | | |
| My spontaneity (ability to act without being "guarded" or defensive) is: | | | | | |
| My ability to function "smoothly" and "coolly" is: | | | | | |
| My ability to function calmly in times of stress or emergency is: | | | | | |
| My ability to function patiently with others in times of stress or emergency is: | | | | | |
| My tolerance of surrounding noise and confusion is: | | | | | |
| My tolerance of surrounding flashing lights and confusion is: | | | | | |
| The number of bad emotional feelings I have is: | | | | | |
| My ability to concentrate in all types of environments is: | | | | | |

| PHYSICAL | well below average | below average | average | above average | well above average |
|---|---|---|---|---|---|
| My ability to fall asleep is: | | | | | |
| My ability to sleep throughout the night is: | | | | | |
| My ability to sleep soundly and deeply is: | | | | | |
| The number of pleasant dreams which I have are: | | | | | |
| My ability to remember my dreams is: | | | | | |
| The number of times in which I awaken refreshed and energetic is: | | | | | |
| My energy level throughout the day is: | | | | | |
| My energy level at the end of the day is: | | | | | |
| My sexual energy level is: | | | | | |
| My sexual drive is: | | | | | |
| My level of uncontrollable anger is: | | | | | |
| My level of calm relaxation is: | | | | | |

TABLE 3

| PHYSICAL | well below average | below average | average | above average | well above average |
|---|---|---|---|---|---|
| My impulsivity is: | | | | | |
| The number of headaches I have is: | | | | | |
| The number of muscle aches, pains, soreness, joint tenderness is: | | | | | |
| My overall background level of pain is: | | | | | |
| My appetite stability (having an appetite that is roughly the same day in and day out) is: | | | | | |
| The number of times I get a nervous stomach is: | | | | | |
| My accident proneness is: | | | | | |
| The amount of bad physical feelings I have is: | | | | | |

| SPIRITUAL | well below average | below average | average | above average | well above average |
|---|---|---|---|---|---|
| My sense of emptiness is: | | | | | |
| My sense of a Loss of Meaning about life is: | | | | | |
| My sense of doubt about myself and the meaning of what I do is: | | | | | |
| The number of times in which I feel like a martyr (feeling like a victim) is: | | | | | |
| The number of times I find myself wishing for or looking for a "magical" solution is: | | | | | |
| The number of times I am somewhat "hard" and unforgiving of others is: | | | | | |
| My sense of a Loss of Direction is: | | | | | |
| My Need to Prove myself is: | | | | | |
| My cynicism (distrust, pessimism, skepticism) is: | | | | | |
| My apathy (indifference, lack of concern) is: | | | | | |

| MEMORY | well below average | below average | average | above average | well above average |
|---|---|---|---|---|---|
| My short-term memory is: | | | | | |
| My immediate recall (the ability to recall a word, a name, event, date, etc.) is: | | | | | |
| My ability to concentrate and learn is: | | | | | |
| My ability to retain what I have read or heard is: | | | | | |
| The ease with which I learn is: | | | | | |
| My interest in reading is: | | | | | |
| My interest in studying my schoolwork or for my job is: | | | | | |

After thousands of years of speculation about the nature of alcoholism and other impulsive, addictive, compulsive behaviors, and half a century of intensifying research into their causes, a consensus is beginning to emerge that is agreed to by most scientists in the field: craving for abusable substances is a malfunction of the reward centers of the brain involving the neurotransmitters the enzymes that control them and that certain other repetitive behaviors are due to imbalances of neurotransmitter systems.

As yet, this information has not led to dependable methods of prevention or cure. In the area of addiction, abstinence is still the only sure way to combat addiction to alcohol or drugs. But we now have adjuncts that make treatment easier. Tests are under development that will enable us more accurately to identify individuals at risk. The goal is to diagnose individuals "at risk" for RDS behaviors sufficiently early to prevent the impulsive, addictive, or compulsive behavior from becoming established and to diagnose them accurately enough to help in the removal of the treatment retarding "denial" phenomenon. An additional goal is to provide more targeted treatment in tertiary probands either for alcoholism with bromocryptine as a function of one's genome (Lawford et al., 1995) or for carbohydrate binging with chromium response as a function of one's genome (Blum et al., 1999). The important point to make here is that as we make progress with regard to understanding the human genome, and as we continue to identify genetic links to polymorphisms for many disease states the more refined treatment approaches will be derived from such knowledge. In fact we believe, a new scientific term will emerge in this new millennium— Pharmacogendmics. This area of endeavor will help define the role of our genome in terms of individual differences with regard to a number of drug responses including pharmacokinetics and pharmatherapeutics.

The relationships among a wide range of impulsive, addictive, compulsive behaviors—from alcoholism to drug addiction to food abnormalities to attention deficit disorder—are now beginning to be understood, and the door to effective therapies is beginning to open wide.

The first definitive insight grew out of the discovery that addiction-free behavior is facilitated by an adequate supply of neurotransmitters; the availability of enzymes to regulate the supply of such brain chemicals and maintain balance among them; and the presence of receptors to give neurotransmitters access to the neurons that determine feelings of well-being. A malfunction in any of these areas may trigger a biogenic behavioral disorder.

The second definitive insight was that these various RDS disorders involve complex interactions of neurotransmitters.

In alcoholism, for example, we may see the progressive involvement of serotonin, opioid peptides, GABA, dopamine, and—in some instances—norepinephrine. Each in its turn initiates or promotes changes in the brain's biochemistry.

The third definitive insight grew out of the discovery of an association between a severe form of alcoholism and defects in the $D_2$ gene in the reward area of the brain and other dopaminergic genes (i.e. the dopamine transporter gene and the dopamine P-hydroxylase gene). This genetic defect leads to such behavioral disorders, as severe alcoholism, polysubstance abuse/dependence, attention deficit disorder, and carbohydrate binging, severe gambling, nicotine abuse among other behavioral abnormalities.

The fourth definitive insight was that these physiological conditions constitute a somatopsychological syndrome: sequential changes in brain chemistry that cause or trigger changes in feelings, beliefs, and behaviors. Just as emotional and mental disturbances can lead to physical illness as in psychosomatic medical theory, so somatic deficiencies or imbalances can cause emotional and mental disturbances including compulsive diseases, anxiety, hostility, depression, or anti-social attitudes. If a genetic defect is the original cause of the behavioral anomaly, somatopsychological responses may be the mind's way of coping with or adapting to the problem in the gene. The recent scientific literature continues to support this definitive insight (see meta analyses by Uhl et al., 1993; Blum et al., 1995; and, Noble, 1998).

The initial work opening the way to an understanding of common causes underlying compulsive behaviors was carried out by the present inventor and associates in 1990. A variant of the $D_2$ gene was shown to be associated with a severe form of alcoholism. This sparked numerous studies of similar associations of gene variants with a wide spectrum of related compulsive disorders.

As previously discussed, numerous studies found significantly high prevalence of the $D_2$ variant gene in subjects with ADHD, Tourette's Disorder, conduct disorder, and posttraumatic stress disorder (PTSD). One striking example was that 59 percent of Vietnam veterans with PTSD carried the $D_2$ gene variant, compared with only 5 percent of those who did not. These results suggest that not only do drug abuse, ADHD, Tourette's Disorder, conduct disorder, and PTSD have a common genetic origin, but that the $D_2$ gene is one of the primary causative factors.

Given the widespread prevalence of ADHD in children and the frequent association of ADHD with substance use disorder and a wide range of other behavioral disorders, it seems reasonable to suggest that childhood ADHD may be a predisposing cause in these other anormalies or at least a pre-existing condition.

Gittleman (1985), for example, found a significant correlation between ADHD and adult substance use disorder. Studies by Comings (1991) showed an intimate relationship between Tourette's Disorder and ADHD. In his various studies, 50 percent to 80 percent of persons with Tourette's Disorder had ADHD, and 20 percent to 60 percent of their relatives, who themselves had Tourette's Disorder, also had ADHD.

While the exact identity of the genes causing ADHD and Tourette's Disorder are still unknown, mutations of genes affecting dopamine function have been strongly implicated. Certainly, the $D_2$ gene appears to be one of the primary genes involved. One of its variants seems to lower the number of $D_2$ receptors, thereby affecting dopamine function, and perhaps playing the role of risk factor for ADHD, Tourette's disorder, conduct disorder, anti-social personality disorder, food binging, smoking behavior, post-traumatic stress disorder, pathological gambling, and polysubstance dependence, including severe alcoholism.

While other genes playing a role in these interrelated disorders are still to be identified, the concept of a "Reward Deficiency Syndrome" (RDS), first proposed by KB, unites addictive, impulsive, and compulsive behaviors and may explain for the first time the way in which simple genetic anomalies give rise to complex aberrant behavior.

As Milam (1992) pointed out in his landmark paper, "The Alcoholism Revolution", which may serve the addiction field best by providing a blueprint for action: "---- meanwhile, the ugly battle for control will continue in the political arena. The public has heard the hostile allegations (Fingeratte 1988) that nobody understands alcoholism, that alcoholism does not exist, that it is merely willful misbehavior, that since treatment does not work anyway, only the briefest and least expensive should be funded. ". . . every word they say chagrins us" . . . because all of these criticisms are true of the bankrupt psychogenic approach to alcoholism; none, however, is true of the biogenic approach."

In a more modern approach to treat or prevent the onset of RDS behaviors, we know that premorbid behaviors to substance use disorder, including nicotine dependence, food addiction, violence, sexual deviancy, acting out in a variety of uncontrollable type behaviors, potentially could be treated with behavioral therapy, along with amino acid therapies, pharmaceuticals, electrical therapies, acupuncture type therapies, subluxation correction, biofeedback therapies, which all work on the neurophysiological mechanisms controlled by our brain. This novel approach will short circuit the genetic roots to this premorbid trait and reduce RDS behaviors.

It is the hope of the inventor that, through rigorous scientific exploration in both animals and humans, still unsolved mysteries about our "addictive brains" will become less mysterious. However, at this juncture we believe that great progress already has been made and it is time to move from the bench to the clinic and begin to apply our present knowledge base. In this regard we are working, in different ways, toward the development of standard diagnosis and treatment of "Reward Deficiency Syndrome".

The inventor is hopeful that he will find an optimal amino-acid composition which will constitute the core of the short-term intravenous bolus therapy similar to what has been proposed in this provisional application.

The inventor is convinced that treatment of RDS associated behaviors should consist of:

physiological and psychological diagnosis (based on genetic testing, brain electrophysiological mapping and psychometric testing);

re-balancing the neurotransmitters (through pharmacotherapies and amino acid based therapies)

neurotransmitter activation (through biofeedback, cranial electro stimulation, acu puncture/auriculotherapy and perhaps chiropractic induced subluxation); and, traditional therapies (including psychotherapy, self-help groups, structured aftercare programs, etc.).

They also are convinced the treatment of RDS behaviors in the future will include the development of a wide variety of treatment settings which include development of community out-patient clinics, day hospitals, inpatient treatment programs, etc. These treatment programs will have programs geared for all the subtypes of behavioral problems under one-roof similar to the a one-stop shopping network. All of the RDS behaviors will be treated together in one location (alcoholism, substance use disorder, smoking, eating disorders-carbohydrate bingers, pathological gambling, sex addiction, violent offenders, and attention deficit hyperactivity disorder).

It is the goal of the inventors to continue the search for solutions to the world's oldest dilemia our addictive brains and we believe through sound scientific exploration as described herein, we will as humans begin to learn how to ease oue "legacy of pain".

In Alcohol and the Addictive Brain (1991) *Blum* (in collabration with Payne) stated: "In the remainder of this century and the early decades of the century to come, I think that we will see neurobiology, neuropharmacology, biogenetics, psychiatry, and medicine moving forward in close coordination to reduce the devastating behavioral and social costs of faulty brain function. My vision of the future is a world in which the chemical and electrical functions of the brain are understood; the problem of chemical imbalances as they affect behavior has been solved; the role of genetic anomalies in defective brain chemistry is understood; pharmaceutical and nutritional intervention as an adjunct to Twelve-Step programs and professional treatment is precise and effective; and the technique of defective-gene replacement has been perfected, enabling us to break (or repair) the genetic chain of inherited addiction. In this world, each individual will be able to enjoy the inborn legacy of reward and pleasure without having the need for addictive substances, without having to pay the price of addiction and pain.

Currently, due to poorly distributed knowledge regarding the etiology of the variety of RDS behaviors, all the treatment categories listed above are treated separately. We the inventors, believe that with the knowledge base described in this patent application the rationale of developing standard protocols for the treatment of all RDS behaviors (Intravenous amino-acid bolus short-term therapy) in integrated groups is clear and clearly will be cost effective. This should give all of us involved in the diagnosis and treatment of impulsive, addictive, compulsive disorders hope for the future.

Moreover, it is important to realize that awarding of this invention is important because the commercialization of this knowledge will positively benefit millions here in America and around the globe. For example, in the United States alone there are 18 million alcoholics, 28 million children of alcoholics, 6 million cocaine adicts, 14.9 million people who abuse other substances, 25 million people addicted to nicotine, 54 million who are at least 20 pounds overweight, 3.5 million school-aged children with ADHD or Tourette's syndrome, and about 3.7 million compulsive gamblers. The inventors believe that using amino-acid bolus intravenous therapy on a short term and repeated basis coupled with genotyping humans for the alleles of the DRD2 gene as well as: other genes (described in Blum's PCT application) related to psychological disorders in the present invention is indeed the first steps toward rational treatment for a devastating problem in society.

The invention first provides intravenous compositions for the treatment of RDS behaviors in a subject. In certain aspects this composition comprises the following:

Composition A.

A composition comprising of an intravenous amount of any polar or non-polar substance known to inhibit the enzymatic-destruction of an opiate/peptidyl opiate or opioid. The intravenous solution must contain an opiate destruction-inhibiting amount of at least one substance which inhibits the enzymatic destruction of a neuropeptidyl opiate, the substance being either amino acids, peptides, and structural analogues or derivatives thereof and zinc/zinc complexes.

Composition B.

A composition comprising of an intravenous amount of any polar or non-polar substance known to act as a neurotransmitter synthesis-promoting amount of at least one neurotransmitter precursor, the neurotransmitter precursor being either a dopamine precursor such as L-Tyr, L-phe and L-dopa, a serotonin precursor such as l-Trp and 5-hydroxytrytophan, or a gamma amino butryic acid (GABA) precursor such as L-glutamine, L-glutamic acid, and L-glutamate.

Composition C.

A composition comprising of an intravenous tryptophan concentration enhancing amount of the mineral chromium. The chromium utilized includes but is not limited to chromium piccolinate or chromium nicotinate or polynicotinate salts or other chelates.

Composition D.

A composition comprising of an intravenous polar or non-polar compound known to cause the release of neuronal opiate peptides/peptidyl opiates/opioid peptides such as enkephaline. The enkephaline releaser being, but not limited to, a peptide, and preferably a D-amino acid containing peptide.

Composition E.

A composition comprising of an intravenous polar or non-polar compound known to promote the synthesis and enhance the functional activity of serotonin, opioid peptides, and catecholamines (dopamine and norepinephrine) selected from the group Rhodiola or huperzine, but not limited to these substances.

Composition F

A composition comprising of a intravenous compound known to promote neuronal dopamine release in the nucleus accumbens, selected from the group consisting of ethanol and calcium, but not limited to these substances.

The type of enkephalinase inhibitors, the neurotransmitter precursor, chromium compound, enkephalinase releaser and neurotransmitter synthesis promoting substance and enhancer of neurotransmitter functional activity alone or combined (combining at least one composition A–E), in addition to the compounds specifically listed above, are further described herein in this application and are encompassed by this invention. In certain preferred aspects of the invention, the composition is preferably used in the treatment of SUD and other preferred embodiments such as smoking behavior, carbohydrate bingeing and even ADHD, attentional processing and/or memory, and stress. As used herein "derivative" may refer to a chemically modified compound, and "anolog" refers to a different compound that has similar properties or structure to the compound it is being compared.

In certain aspects of the invention, these intravenous compositions which have never been used before as short-term bolus therapy, may be used in the treatment of all RDS related behaviors previously disclosed in Blum's published PCT application of Apr. 29, 1998 which has: been nationalized in numerous countries on Oct. 29, 1999 and Nov. 29, 1999. RDS behaviors are those behaviors related to a chemical imbalance which manifests itself as one or more behavioral disorders related to an individual's feeling of well-being with anxiety, SUD, smoking, Body Mass Index, Obesity, carbohydrate binging, pathological gambling, sexual deviancy, axis II diagnosis, Schizoid avoidant behavioral cluster, ADD/ADHD, conduct disorder, Tourettes Syndrome, family history of SUD, and obesity as well others previously defined as well as other non-RDS disorders as defined herein.

The inventor believes that various psychological disorders are linked by a common biological substrate, a "hard-wired" system in the brain that provides pleasure in the process of rewarding certain behavior. The inventors propose in this invention that an inborn chemical inbalance that alters the intracellular signaling in the nucleus accumbens or other limbic reward regions could supplant an individual's feeling of well-being with anxiety, anger or a craving for a substance (i.e. alcohol) that can alleviate the negative emotions. This chemical inbalance manifests itself as one or more behavioral disorders for which the term "Reward deficiency Syndrome" has been coined (Blum et al. 1996a).

While a major aspect of this invention involves the use of an intravenous amino-acid based bolus composition for the short-term treatment of RDS behaviors as well as other non-RDS behaviors, disorders or diseases, certain aspects of this invention does involve the coupling of intravenous administration with gene testing. The gene testing aspect has already been applied for via a previous PCT application (Apr. 29, 1998). In order to be complete it is important to realize that in RDS, genetic defects in the reward pathways is best understood as a polygenic disorder, and genetic testing would require the testing of multiple genes. The earlier PCT identified the correlation between predisposition to RDS and alleles of a number of genes including but not limited to the dopaminergic genes DRD1, DRD2, DRD3, DRD4, DRD5, dopamine transporter gene (DAT1); serotonin genes HTT, HTRA, HTRDb, HTRA, HTRC, HTIA, 5HT2R, tryptophan 2,3-hydroxylase (TD02); Norepinephrine genes, DbH, ADRAA, ADRAC, NT; Catecholamine metabolizing genes, MAOA, COMT; GABA genes, GABRAA, GABRAB; Canabinoid receptor gene, CNR; Nicotinic cholinergic, CHRNA; NMDA receptor gene, NMDAR; Enkephalin genes. PENK: Androgen receptor gene, AR; Interfereron gamma gene, INFG, CDA; Presenilin, PS; CRF gene, CRF; obesity genes, OB, leptin recteor gene; catechol-O methyl-transferase (COMT) gene; the neuronal nitric oxide gene synthase gene (nNOS1α); Apolipo protein-D (APO-D) and, uncoupling protein (UCP1 and UCP2) among others.

Enkephalins and endorphins are opiate-like substances which have been found to be endogenous in various animal species and man, whereby the general term endorphins includes but is not limited to Beta-endorphin, methionine-enkephalin, leucine-enkephalin and dynorphins. These substances are peptides or polypeptides which are normally found in the brain and in the periphery as well.

As pointed out in U.S. Pat. No. 4,439,452, it has been observed that both enkephalins and endorphins have an ability to act as a biologically active pain killer when administered by even intracerebral injections. However, the major drawbacks of utilizing the endogenous substances directly for therapeutic purposes, including intravenous therapy to treat RDS or non-RDS disorders, are their extremely labile nature and poor penetration into the brain via oral administration and their ability to induce addiction. It is known that the destruction of the endognous enkephalins and or endorphines is due to the actions of certain enzymes which resemble carboxypeptidase or endopeptidase (catelepsin), respectively. These and other enzymes which inactivate enkephalins and endorphins are known collectively as enkephalins and endorphinases. An enkephalinase F inhibitor is a substance which inhibits a class of enzymes known as enkephalinases and endophinases known to destroy these neuropeptides in both animals and humans.

Pharmaceutical Compositions

Aqueous compositions of the present invention comprise an effective amount of the various compounds disclosed to treat RDS related disorders, including substance use disorder, obesity, ADHD, Tourettes syndrome, PMS, smoking, any other related behavior described herein, dissolve or dispersed in a pharmaceutically or pharmacologically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

A preferred chromium salt, in addition to those previously mentioned, is chromium niacin-glycerate. Clyclodextrin maybe added to composition in the kits of the present invention. This clyclodextrin could aide in the absorption of many of the various components in the composition. The kits also preferably contain a reward deficiency syndrome related scale. This scale allows the patient to gage the degree of his RDS problems.

Each of the several embodiments of the invention hereinafter to be described not only reduces intake of alcohol, cocaine, heroin, nicotine, glucose but reduces all known RDS behaviors. The following examples of compositions is provided to best describe the invention herein:

Example I

Composition A

The invention includes the intravenous administration of a new class of anti-craving compositions provided by substances which inhibit the breakdown of endogenous substances such as enkephalins and endorphins. Specifically, D-phenylalanine, DL-phenylalanine, D-Leucine, DL-Leucine, and hydocinnamic acid, each in an intravenous solution in sufficient concentration to bring about enkephalinase inhibition which would significantly lower alcohol intake in animals and humans. The anti-alcohol desire effect has been observed in animals genetically prone to choose alcohol over water, but this effect has never been observed via the intravenous route. The inventors believe that the intravenous route would be advantageous since the dose needed would be much less than what is required by the oral dose. In a series of experiments the exact dose will be determined in both humans and animals to at least reduce alcohol or drug intake. In this invention only and not in limitation, the term enkephalin inhibitors includes D-phenylalnine (DPA), DL-PA, hydrocinnamic acid and D-amino acids such as D-leucine. It is anticipated that other enkephalinase inhibitors (depending on ability to place the substance into a safe and effective intravenous solution) selected from a group consisting of certain protein synthesis inhibitors (bacitracin, bestatin, and puromycin); and peptide amino acids (mono free form amino acids in the D-form; thiol benzyl amino acids (2-[mercapto-3-phenyl-propanoyl]-L-leucine; carboxyalkyl methyl esters, N-[(R, S)-2 carbethoxy-3-phenyl propanol]-L-leucine; as well as a number of other structurally unrelated compounds such as secobarbital, pyrophosphate, o-phenanthroline, phosphamidon, Z-Ieucine-NHOH, and Z-glycine-NHOH.

The potencies will be determined by trial and error, but a starting point for the various enkephalinase inhibitors in vitro range from 10 nM to nM amounts and, therefore, the anticipated human dosage range is from milligrams to micrograms per kilogram based on a 80 kilogram man. It is understood that the daily, recommended dosage is to be sufficient to alter the activity of enkephalinase and/or opioid receptor function so as to reduce the craving for euporiants such as alcohol, cocaine, heroin, marijuana, nicotine, glucose as well as behavioral acts including but not limited to pathological gambling and sexual deviancy. It is further anticipated that the broad range of dosage will be provided in the final application due to both pharmacogenetic and pharmacogenomic elements. It is also important for this invention, that these substances alone, in equal dosages are less efficatious enkephalinase or endorphinase inhibitors in reducing craving but should be synergistic when used in combination with said inhibitors and other precursor aminoacids and even when combined with intravenous ethanol solutions.

An intravenous solution of D-Phenylalanine 16500 mg For example, without testing, it is anticipated, that the range of the daily dosage of D-amino acid like D-leucine is between 15–5000 mg but a more definitive amount will be determined. The intravenous solution could be expanded to include any substance which inhibits enkephalinases, endorphinases and or dynorphinases. It is also anticipated that intravenous solutions could also contain the DL-forms as well.

Example II

Composition B

The inventor believes that the substrate for RDS behaviors is mediated by regions in the brain's "pleasure center" or "reward centers" which are high in a number of neurotransmitters including dopamine. These regions include the dopamine—containing nucleus accumbens, and its projection to limbic structures and frontal cortex. It has been observed that if dopamine projections to limbic and cortical areas are lessioned the self-administration of psychoactive drugs which release dopamine (e.g. alcohol, cocaine, heroin, nicotine etc) by animals are greatly reduced. Moreover, selective dopamine receptor antagonists, like haloperidol, atenuate or block alcohol and cocaine self-administration in animals. Similarly, in humans, pretreatment with dopamine receptor antagonits will block stimulant-induced "euphoria". Additionally, dopamine receptor agonists e.g. bromocryptine, apomorphine etc) have rewarding actions. These and other studies suggest that the lack of "reward" as observed in RDS subjects is due to a deficiency of certain neurotransmitters involved in the mediation of dopamine release and function.

A second step in the invention is to induce restoration and balance within the limbic structures of important neurotransmitters. This is accomplished by utilizing the brain's own natural biochemical mechanisms involved in the synthesis of individual chemical messengers such as serotonin, Gamma-amino-butryic acid (GABA) and the catecholamines (dopamine norepinephrine and epinephrine). In understanding the chemistry involved, these neurotransmitters of the monoamine type are derived via enzymatic actions concerned with known precursor amino acids.

Catecholamine are compounds which passes two adjacent hydroxyl (OH) groups; on a benzene ring. In the body, such substances are synthesized from the aromatic amino acid L-tyrosine, which is hydroxylated to L-3,4-dihydoxyphenylalanine (L-DOPA) by the enzyme tyrosine hydroxylase. L-trosine is actively taken up into noradrenergic nerve terminals. L-phenylalanine is a precursor of L-Tyrosine. In the cytoplasm, L-DOPA is decarboxylated to dopamine by L-aromatic amino acid decarboxylase, an enzyme which requires pyridoxal phosphate (vitamin B6) as a cofactor. The dopamine is actively taken up into granular storage vesicles in which the dopamine is hydroxylated to form norepinephrine by the enzyme dopamine-beta-hydroxylase.

It is known that dopamine is the precursor of norepinephrine and epinephrine, and each of these three neurotransmitters have distinct functions in the central nervous system and at some ganlia in the autonomic nervous system. Dopamine is stored in storage granules where the catecholamine is complexed with chromogranins, divalent metal ions and ATP. Dopamine is believed to be released into the syneptic cleft by exocytosis. As with norepinephrine, this is a calcium dependent process and occurs in response to action potentials reaching nerve terminals or to drugs. The following drugs/substances can induce a dopamine release—they include: alcohol, cocaine, amphetamine, methyamphetamine, amantadine, morphine, heroin, phentermine, nicotine, marijauna, glucose to name a few.

The use of these precursors may be supplemented at appropriate stages of treatment of an RDS subject following the short-term bolus intravenous therapy. These include dopaminergic releasers, blockers, agonists or antagonists or agents affecting the reuptake or degradation of dopamine, norepinephrine or epinephrine. However, it should be understood that the entire range of dopaminergic activity including synthesis, and release is regulated to some degree by certain opioid peptides (e.g. enkephalins and endorphins). Centrally administered opioid peptides produce elevations in levels of catecholamines in blood plasma in animals and humans (Clouet Ann: N.Y. Acad. Sci., 398; 130–139, 1982). In fact, blockade of presynaptic dopaminergic receptors results in an enhancement of B-endorphin release, showing a unique reciprocal relationship.

Serotonin (5-HT) is a CNS neurotransmitter. It is also found in the enterochromaffin system of the intestine, and in blood platelets. This neurochemical is biosynthesized by first hydroxylating the precursor amino acid L-Tryptophan to obtain 5-hdroxytryptophan and then decarboxylating the latter to obtain serotonin. The hydroxylation (the rate limiting step) is performed by the enxyme tryptophan hydroxylase, while the decarboxylation is accomplished by the ubiquitous enzyme L-aromatic acid decarboxylase. This enzyme requires pyridoxal phosphate as acofactor.

Unlike tyrosine hydroxylase, tryptophan hydroxylase, under normal physiological conditions, is not saturated, therefore, the enzyme is not working to full capacity and thus tryptophan hydroxylase activity is significantly affected by 1-tryptophan. The amount of available free tryptophan is dependent on a number of factors including the concentration of circulating L-7 tryptophan in the plasma at the rate of its uptake in the brain and presynaptic terminals. We contemplate using L-tryptophan or 5-hdroxytryptophan, to restore the serotonergic system disrupted by either genes or other environmental elements.

There is come controversy concerning the usefulness of another amino acid precursor, 5-hydroxytryptophan, which is about 20 times more potent than L-tryptophan. The rate of entry of L-tryptophan into the brain depends upon the ratio of free-bound tryptophan in the plasma, and this ratio is influenced by the concentration in the blood of neutral amino acids, insulin, glucose levels, and pharmaceutic agents, which compete for plasma protein binding sites, as well as for the tryptophan-uptake sites. Also 5-hdroxytryptophan is taken up by neurons other than just serotoninergic neurons; therefore the increases in serotonin synthesis are not selectively limited to serotoninergic neurons. Since the inventors plan to utilize the intravenous compositions via an FDA approved drug drug, and since in the United States physicians are allowed to subscribe or utilize L-tryptophan, the preferred embodiment is the L-tryptophan precursor rather than the L-5-hydroxytryptophan amino-acid.

Serotonin can be released into the synaptic cleft by the process of exocytosis in response to action potentials and to certain drugs/substances. Facilitation of serotonin release is accomplished with cocaine, alcohol, amphetamine, metamphetamine, fenfluramine, chlorimipramine and others. GABA is an inhibitory neurotransmitter which controls the release of dopamine (Gessa et al. 4th World Congress on Biological Psychiatry 459 No. 620:10 1985).

The main synthetic pathway to gamma-aminobutyric acid is via decarboxylation of L-Glutamic acid by glutamic acid decarboxylase (GAD). Like other amino acid decarboxylases, this enzyme needs pyridoxal phosphate or vitamin B6. GAD is found exclusively in the cytoplasm of an synaptic GABA nerve terminals. The basic control of GABA synthesis is GAD, which is the rate limiting step. Saturation concentrations of L-glutamic acid are present in the presynaptic neurons: thus, increased substrate concentrations do not normally affect the rate of GABA synthesis. Therefore, the exogenous administration of L-glutamic acid may not significantly increase GABA levels, unless the L-glutamic levels are abnormally low. However, it has been shown that a 10 day administration of 1-glutamine (@ 500 ng/kg per day) with the drinking water to adult albino rats resulted in significant increase in the content of glutamate, GABA and taurine in the brain. Glutamine is an active intermediate in transport of ammonia from brain and therefore may greatly affect metabolism of different amino acid acids in nervous tissue. After deamination, glutamine may become a precursor of glutamate and, accordingly, GABA. (Thawki et al. J. Neurochem. 41:611–617, 1983).

Changes in affinity of GABA receptors for GABA, the benzodiazepine-binding sites for benzodiazepines and/or barbiturate binding site for barbiturates is regulated by a protein "GABA-modulin". No reports have indicated that the use of GABA precursors can postively affect RDS behaviors in the short-term. However, the inventors believe, that since in a number of RDS behaviors there is a significant association of stress and/or anxiety the addition of L-glutamine may act to increase GABA, which in turn could stimulate the benzodiazepine-ionophor complex and reduce anxiety through this mechanism, even on a short time period for initial interaction via the intravenous route.

It will also be recognized that while this invention is directed to the use of a substance which inhibits the destruction of endogenous neuropeptidyl opiates (as described in Example 1), especially in combination with dopamine, serotonin and/or GABA precursors, it may also be beneficial to add certain soluble neurotransmitter agonists, blockers, antagonists, releasers, or degradation inhibitors into one intravenous solution if desired or if proven to effect the efficacy of the base composition.

There are other substances which could also effect the activity of neurotransmitters and brain cell dynamics which can be contemplated as well in this invention. For example, calcium; is a required substance for proper neurotransmitter release and function. Zinc is essential for protein synthesis and can inhibit enzymes involved in the destruction of endogenous opiates. Thiamine promotes the synthesis of niacinamide and enhances oxidative metabolism of brain cells. Riboflavin is a cofactor which acts as a hydrogen acceptor and promotes the conversion of tryptophan to niacinamide. Niacinamide is an essential part of the enzyme system concerned with the efficient use of oxygen by neurons and promotes brain cell respiration. Pantothenic acid is a vital substance involved in cellular metabolism. It is believed that the combination of riboflavin, niacinamide, and pantothenic acid reduce irritability, restlessness and fatigue. Cyanocobalamine is a cofactor/coenzyme for both chemical synthesis and neuronal electrical activity. Ascorbic acid is involved in the metabolism of phenylalanine and tyrosine and can reduce drug-induced withdrawal reactions. Follic acid promotes oxidation in the blood as a hematopoietic agent. D-Ribose is a cardiac protector and may play a role in memory.

An example of the precursor amino-acids in treating RDS behaviors as an intravenous composition is as follows:

In an intravenous solution these amino-acid precursors could be given alone or in any combination with any of the other precursor amino-acid at the specified dosage range.
L-phenylalanine 5 mg–5,000 mg daily dose.
L-Tyrosine 5 mg–5,000 mg daily dose.
L-Tryptophan 9–90,0000 mg daily dose.
L-5-hydroxytryptophan 0.9–9,000 mg daily dose.
L-Glutamine 3–30,000 mg daily dose.
One preferred embodiment is as follows:

| Amino Acid Precursor Formulation Daily Dose | |
| --- | --- |
| L-Phenylalanine | 1500 mg |
| L-Tyrosine | 900 mg |
| L-Tryptophan | 500 mg |
| L-Glutamine | 300 mg |
| Pyridoxal Phosphate | 20 mg |

Note:
While the foregoing doses are preferred, it is contemplated that the quantities of each ingredient may be varied by an order of magnitude (10% to 1000%). Because of the interactions of the various neurotransmitters, an increase in the amount of one ingredient may facilitate the reduction of another ingredient. Also, other substances of similar activity, as noted above in the text of this invention, may be substituted for those of the Example.

Example III

Composition C

In this composition the inventors are including a tryptophan concentration enhancing amount of all salts and chelates of chromium (e.g. picolinate, nicotinate, ablion chelate etc).
Background on Chromium Body cells need chromium to keep insulin working properly as well as a host of other important biological actions. Scientists agree, that insulin directs the movement of digested food into the body's cells and affects how that food is used. When insulin doesn't act as intended, blood glucose and fat aren't stored and used properly. This malfunction leads to obesity, heart disease, or diabetes.

Our diets contain little chromium, and what chromium we do eat is often in a form that is difficult for the body to absorb. Therefore, chromium must be combined with a substance that will allow this substance to enter the bloodstream. A number of forms include picolinate, polynicotinate as well as Ablion chelate. Dozens of studies have proven that chromium, in the form of chromium picolinate, helps control blood fat, blood glucose, body fat, food cravings, and age-related bone weakening or osteoporosis, lowers blood pressure and reduces both total and LDL cholesterol, and induce higher levels of HDL cholesterol.

Dietary chromium is an essential nutrient whose value in human nutrition has been conclusively documented. Interest in chromium stems from the view that because chromium is an essential trace mineral and a cofacactor to insulin, it could play a role in glucose, lipid, and amino acid metabolism by it's potentiating effects on insulin action. Supporting this argument is the observation that chromium deficiency results in impaired glucose tolerance, insulin resistance, elevated blood glucose levels, and symptoms of type 11 diabetes; in addition, adequate amounts of physiogically active forms of chromium can reduce insulin requirements in humans (Kaats et al. 1996).

The National Academy of Sciences has classified chromium as an essential trace mineral and recommends daily intakes of 50 to 200 micrograms. However, the most reliable studies report that among Americans (which is similar for other countries) is suboptimal—only 40% of the minimum for women and 60% for men. There are more than 25 human studies documenting the beneficial effects of supplemental chromium on subjects living at home including improvements in glucose, insulin, and lipid levels: impaired glucose tolerance; adults with elevated cholesterol levels; insulin and hypoglycemic patients (Mertz, 1992).

To increase the bioavailability of chromium, several studies have suggested using picolinate acid, a naturally occurring metabolic derivative of tryptophan. Picolinate acid appears to combine with trace metal ions in the intestines and blood which facilitates the collection and use of essential trace metals (Evans & Brown, 1992). We are in this invention, only interested in the intravenous use of chromium. We will explore the absorption of unsalted chromium compared to various salts and chelated forms in terms of absorption and potency using typical studies involving glucose sensitivity and tolerance as a measure of biological activity.

Enhancing Brain Tryptophan

Because deposition of body fat appears in part by insulin, improvements in insulin utilization should lead to reductions in fat deposition. Enhancing the effects of insulin can also have positive effects on muscle tissue because insulin directs amino acids into muscle cells; once amino acids enter the muscle cells, they are assembled into proteins through insulin's effect on the cell's genetic material, that is, DNA and ribonucleic acid. This effect of chromium is important for this invention, since by doing so it reduces required amounts of the amino acid tryptophan (Wurtman, 1982). By enhancing tryptophan, this will lead to an enhanced synthesis of serotonin. The newly synthesized serotonin, will stimulate dopamine release via an indirect action on enkephalinergic neurons resulting in GABA inhibition, and through this mechanism enhance dopamine release at the nucleus accumbens. This would therefore benefit RDS behaviors, including substance use disorder, carbohydrate binging, pathological gambling, sexual deviancy, ADHD among other known and defined RDS behavioral subtypes.

Moreover, chromium can potentially facilitate the maintenance or addition of fat-free mass (FFM). It has been suggested that if chromium can lower insulin resistance it can improve body composition, as insulin resistance or deficiency results in impaired entry of glucose and amino acids into muscle cells, and increased catabolism of muscle protein as well as insulin deficiency's potential to accelerate lipid disposition (Kaats et al. 1996). Other references indicate that insulin resistance may help stabilize body fat in the obese patient, albeit at an obese level, acting much like a "set point" to prevent further weight gain (Eckel, 1992).

Why Intravenous

In general, although animal studies have supported this contention (Liarn et al, 1993), one human study found positive changes in body composition with chromium supplements (Hasten et al. 1992), another reported positive, although not statistically significant changes in body composition (Hallmark et al. 1993), and a third failed to find any positive changes in body composition with chromium supplementation (Clancey et al. 1994). The controversial nature of the literature reveals that most human studies used small numbers of subjects, and patients often followed exercise or conditioning programs that could increase the need for chromium at amounts higher than amounts provided in these studies. Previous work observing concurrent chromium supplementation and exercise training has been restricted to effects on body weight and composition, with conflicting results (Clancy et al, 1994; Evans et al 1989; Evans et al, 1993; Hallmark; et al. 1996; Hasten et al. 1992). Chromium Picolinate is the most heavily used, studied and promoted compound, but in vitro work suggests that chromium nicotinate may be also viable in the area of weight loss and changes in body composition. In this regard, very recent work by Grant et al. (1197), suggests that the nicotinate salt may be even more important than the picolinate salt.

While there still is controversy regarding the effects of chromium salts (picolinate and nicotinate) on body composition and weight loss in general, recent work seems to support the positive change in body composition in humans. Considering the work of Lawford, et al. (1995), showing a selective positive effect of bromocryptine, a $D_2$ agonist, in reducing relapse rates in alcoholics as a function of dopamine $D_2$ receptor genotype, one of us (KB) embarked on a similar phamacogenomic study with CrP (see below).

Recently, there was concern over the demonstration that, at concentrations thousands of times higher than physiological levels, trivalent chromium can break chromosomes in cell culture. It is the inventor's position that this finding is not relevant to nutritional supplementation. In this regard, a prediction that CrP will accumulate in tissues to dangerous levels during long-term supplementation is based on an inappropriate pharmacokinetic model and is at odds with data from long-term rat feeding studies. Furthermore, clastgenicity is not equivalent to either mutagenicity or carcinogenicity and studies in animals reveal that any effects observed with regard to clastogenicity of trivalent chromium is only relevant to cell culture studies, not to living animals or humans. Moreover, the therapeutic-toxic-dose ratio for trivalent chromium is 1:10,000 and the Environmental Protection Agency in the United States has established a "Reference Dose" for nutritional chromium that is 350 times higher than the upper end of the nutritional range. Considering the wide margin of safety for trivalent chromium, as well as its picolinate salt, we believe large scale, worldwide use of CrP is justified as an important dietary supplement to assist in reducing obesity.

Thus, it can be seen that effects of chromium supplementation on different subject populations (obese and lean) were variable with respect to changes in body composition regardless of dose. Given the comparable study designs for most studies, the results taken together suggest that a subset of responders in each study may account for the observed variability among studies.

In order to resolve the issue of non-responders, the inventor decided to test the hypothesis that typing the obese patients by genotyping the DRD2 gene prior to treatment with CrP would result in a differential treatment outcome. This was based on previous research which indicated that the DRD2 TaqA1 allele associated with obesity in general; the BMI; carbohydrate binging; co-morbid substance use disorder; and contributed to the overall variance of percent body fat in the present population at the high rate of 45.9 percent (Blum et al. unpublished). One of us (KB) predicted carriers of the DRD2 A2 allele would retain the positive metabolic effects of P, but in contrast the DRD2 A1 carriers, because there is a proclivity to increased carbohydrate binging, would possibly mask the metabolic effects of CrP on weight loss and change in body fat attenuating any positive effects. One prophetic example as described earlier (see page 48):

The inventor genotyped 130 obese subjects for the dopamine $D_2$ receptor gene (DRD2) utilizing standard PCR techniques. The subjects were assessed for scale weight and for percent body fat using dual energy X-ray absorptiometry (DEXAR). The subjects were divided into matched placebo and chromium picolinate (CrP) groups (400μg. per day). The sample was separated into two independent groups; those with either an A1/A1 or A1/A2 allele and those with only the A2/A2 allelic pattern. Each of these groups was tested separately for differences between placebo and treatment means for a variety of measures of weight change. These measures consisted of calculations of the percent of fat weight change; the change in fat weight; the change in body weight; the change in free mass, the percent change of fat weight; the body composition index; and the body weight change in kilograms. T-analysis revealed that carriers of the DRD2 A2 allele were more responsive to the effects of CrP than were the DRD2 A1 allele carriers. The measures of the change in fat weight ($p<0.041$), change in body weight ($p<0.017$), the percent change in weight ($p<0.044$), and the body weight change in kilograms ($p<0.012$) were all significant, whereas no significance was found for any parameter for those subjects possessing a DRD2 A1 allele.

These results suggest that the dopaminergic system, specifically the density of the $D_2$ receptors, confers a significant differential therapeutic effect of CrP in terms of weight loss and change in body fat. Moreover, we propose for the first time that mixed effects now observed with CrP administration in terms of body composition, may be resolved by typing the patient via DRD2 genotyping prior to treatment with chromium salts.

The point here is that, depending on a number of important factors, genetic make-up as well as absorption results obtained with any chromium supplement are equivocal. It is the intent of this invention to resolve this controversy by administering the chromium via the intravenous route either alone (25–10,000 μg), or in combination with Composition B as specified above.

| Amino Acid Precursor Formulation Daily Dose | |
|---|---|
| L-Phenylalanine | 1500 mg |
| L-Tyrosine | 900 mg |
| L-Tryptophan | 500 mg |
| L-Glutamine | 300 mg |
| Pyridoxal Phosphate | 20 mg |

-continued

| Amino Acid Precursor Formulation Daily Dose | |
|---|---|
| Chromium (picolinate, or nicotinate) | 400 ug |

Note:
While the foregoing doses are preferred, it is contemplated that the quantities of each ingredient may be varied by an order of magnitude (10% to 1000%). Because of the interactions of the various neurotransmitters, an increase in the amount of one ingredient may facilitate the reduction of another ingredient. Also, other substances of similar activity, as noted above in the text of this invention, may be substituted for those of the Example.

Example IV

Composition D

In this composition the prime element is the use of an enkephalinase releasing substance which is known to release neuronal endorphins or enkephalins, said substance being selected from the group consisting of polypeptides or amino-acids.

The inventor believes that an important embodiment is the inclusion of a opioidergic releasing agent. Therefore, a further enhancement of the intravenous composition, is to combine an enkephalinase inhibitor with an enkephalin releasing agent. The rationale for this is that by doing so we could significantly enhance the effect of enkephalin on its respective opiate receptor sites (e.g. delta or mu). To accomplish this aim, we would prefer to use the peptide Tyr-Arg (Kyotorphin), or its stable analog, Tyr-D-arg, which has been shown to be analgesic and to enhance intracellular calcium in synaptosomes in rat brain slices. These substances appear to be putative methionine-enkephalin releases acting by an unknown mechanism (Udeda et al. Biochem,. Biophy. Res. Comum. 137:897, 1986).

To provide both enkephalinase inhibition as well as enhanced neuronal enkephalinase release the substance Kyotorphin may be used as a daily dosage range of 15 micrograms −15 milograms orally. In our experiments to come, the inventors will provide the best dose for the intravenous composition preferred. (Takagi et al. Eur. J. Pharm. 55:109, 1979). The more stable analog Tyr-D-Arg, at a daily dosage range could be substituted as an enkephalin releaser and it to will be studied in terms of it's appropriate effective and safe intravenous dose (Tajima et al. Chem. Pharm, Bull. 28:1935, 1980); Ueda, et al. Biochem. Biophys. Res. Commun., 137: 897–902, 1986).

Thus, an enkephalin releaser may be combined with an enkephalinase inhibitor to achieve a high degree of enkephalinergic activity at the synapse to further augment the release of neuronal dopamine. This will act as a form of bolus short term "replacement therapy" and produce a surprising long-term reduction in aberrant craving behavior for a number of addictions.

| Amino Acid Precursor Formulation Daily Dose | |
|---|---|
| L-Phenylalanine | 1500 mg |
| L-Tyrosine | 900 mg |
| L-Tryptophan | 500 mg |
| L-Glutamine | 300 mg |
| Pyridoxal Phosphate | 20 mg |

| Amino Acid Precursor Formulation Daily Dose | |
| --- | --- |
| Chromium (picolinate, or nicotinate) | 400 ug |
| Tyr-D-Arg | 15 ug |

Note:
While the foregoing doses are preferred, it is contemplated that the quantities of each ingredient may be varied by an order of magnitude (10% to 1000%). Because of the interactions of the various neurotransmitters, an increase in the amount of one ingredient may facilitate the reduction of another ingredient. Also, other substances of similar activity, as noted above in the text of this invention, may be substituted for those of the Example.

Example V

Composition E

A composition comprising of an intravenous polar or non-polar compound known to promote the synthesis and enhance the functional activity of serotonin, opioid peptides, and catecholamines (dopamine and norepinephrine) selected from the group Rhodiola or huperzine, but not limited to these substances.

Rhodiola rosea, or Golden Root, is a perennial herbaceous plant of the Orpine (Crasssulaceae) family, growing in the Polar Arctic and Alpine regions. In the altai mountains, in Eastern Siberia, Tien-sdhein and in the Far East, the cultivation of Rhodiola rosea has, been successfully mastered.

The rhizomes contain phenolic compounds, among them the most important are p-oxyphenylethanol (tyrasol) and its glycoside salidoside determining the biological activity of the Rhodiola preparations (Saratikav et al. 1968). Rhodiola possess stimulative and adatogenic characteristics. It is thought that this compound improves the ability to perform physical work; reduce fatigue; shorten the recovery period after prolonged muscular workloads; and normalize cardiovascular activity. During intensive muscular work, Rhodiola prevents loss of phosphates in brain and muscles by optimization of the processes of oxidative phosphorylation, stabilizing the muscular activity of lipids; improving the indicators of metabolism (activation of aminacyl-t-RNA-synthetase) in the skeletal muscles, increase of the RNA content, and increasing the blood supply to the muscles, especially to the brain.

Rhodiola can increase attention span, memory; improve mental work and enhance performed work. The area of the brain involved in this activity is the thalamocortical and posterior hypothalamus (Marina et al. 1973). Various other actions have been noted for Rhodiola and include prevent development of hyper-and hypoglycemia, leukocytosis and leukopenia, erythrocytosis and erythropenia, hypoxia; reduce stress and bring about a cardio-protective action. The stress-regulative effect of Rhodiola involves it's normalizing effect on the hypophyso-adrenal and opioidergic system. It has also been found that Rhodiola increases the anti-tumor resistance of the organism. It significantly inhibits the growth of experimental tumors, decreases the frequency of their metastasises; prolongs the life expectancy of animals with recidivistic tumors, and decreases the outcome of spontaneous tumors (Dementyeva and Yaremnko, 1983). There is some evidence that this compound also reduces neurosis and fights exhaustion (Saratikov, 1977).

Salidosid (an extract of Rhodiola) [SAL], at 30 mg/kg prevented disulfuram-induced decrease of NE in the brain of animals. SAL influences brain NE by virtue of it's ability to inhibit the activity of COMT and MAO. SAL does not decrease the permeability of the Blood Brain Barrier (BBB) for precursors of the catecholamines and serotonin, and this property makes it useful for the intravenous composition to treat RDS behaviors. Administration of rhodosine (which contains: SAL, aglycone p-tyrosol and rosavin) at 2 mg/kg increases the brain concentration of DOPA, dopamine, and serotonin in the cortex and a decrease of the level of NE in the caudate nucleus in the brain of the intact mice, 30 min after subcutaneous injection. Others have shown that SAL did not alter the levels of epinephrine and DOPA: at a dose of 30 mg/kg, it decreased the content of NE by 26% and of 5-HT by 15%; at a dose of 100 mg/kg, it decreased the concentration of NE, Dopamine and serotonin by 20, 28, and 23% respectively. Studies involving the administration of L-Dopa (50 mg/kg) and 5-HTP (100 mg/kg) to mice showed that SAL (30 mg/Kg) increases the rise in exogenous DOPA and serotonin in animals by 26 and 13%, respectively, compared to saline-dopa-5-HT-controls. These data indicate that the preparation increased the permeability of the blood-brain barrier for the catecholamine precursor.

Moreover, from the research of Petrov (1981) indicates that SAL decreases MAO activity and inhibits COMT activity thereby, slowing the inactivity of Catecholamines by o-methylation and oxidative deamination. Moreover, studies have shown that SAL does not alter the activity of 5-HTP decarboxylase. Consequently, it does not influence the synthesis of serotonin from 5-HTP, but may slow the biotransformation of the amine, by slightly inhibiting MAO. Evidently the increase in the rise of serotonin in the brain studies involving the combined administration of 5-HTP and SAL is governed by the capacity of the latter to increase the permeability of the blood brain barrier for 5-HTP.

The effects of Rhodiola in rats was studied using several methods of active avoidance with negative and positive reinforcement (Petrov et al. 1986). Using the maze-method with negative reinforcement, it has been found that Rhodiola extract in a single dose of 0.10 ml per rat improves learning and retention after 24 hours. In terms of the bolus therapy, it is of interest that significant improvements of the long-term memory is also established in memory tests after 10 day treatment with the same dose of the extract. Other work on the positive effects of Rhodiola on learning and memory has been noted (Lazarova et al. 1986).

Huperzine is a compound belonging to a class known as acetylcholinesterase inhibitors. It has been shown to inhibit the enzyme that is responsible for the breakdown of acetylcholine, an important neurotransmitter, or brain chemical, which is critical in not only memory and/or learning but is critical in peripheral nervous system as well. This could have a beneficial effect in the disorder known as Myastenia Gravis. Huperzine is a naturally occurring compound that: was originally isolated from the club moss Huperzine Serrata. It has been used in Chinese folk medicine and more recently in limited clinical trials conducted in China as a treatment for age-related memory disorders. Results suggest that it improves learning and memory in certain patients. However, these suggested results have not been substantiated by clinical trials. This natural substance is contemplated for use with the composition of matter claimed in this patent application (provisional) to affect attentional processing. In humans the recommended oral dose to enhance memory is 150 micrograms daily (the therapeutic range is 1.5 to 1,500 mcg daily). We will determine the best intravenous dose via experimentation alone and in combination with the claimed compositions.

Huperzine A, a novel potent, reversible, and selective acetylcholinesterase (AchE) inhibitor has been expected to be superior to other AchE inhibitors now known for the treatment of memory deficits in patients with Alzheimer's disease. The compound has been studied by a number of investigators including Zhi and associates (1995) with very positive results. In fact huperzine A is superior in activity to Cognex$^R$, the first drug licensed in the USA for Alzheimer's disease. The drug also blocked glutamate-induced cellular death of neurons. The duration of action of Huperzine A at 3 hours is superior to Cognex$^R$ (2 hours) and physostigmine (30 min.). In behavioral studies of learning and memory enhancement in animals, the difference between amounts of the extract effective for memory and learning and the non-toxic-effect dose was 30–100 fold. These data strongly suggest that Huperzine A can be useful in treating Alzheimer's disease with minimal side effects.

Toxicology and efficacy studies of Huperzine A show it to be non-toxic even when administered at 50–100 times the human therapeutic dose. The extract is active for six hours at a dose of 2 micrograms/kg with no remarkable side effects.

| Amino Acid Precursor Formulation Daily Dose | |
|---|---|
| L-Phenylalanine | 1500 mg |
| L-Tyrosine | 900 mg |
| L-Tryptophan | 500 mg |
| L-Glutamine | 300 mg |
| Pyridoxal Phosphate | 20 mg |
| Chromium (picolinate, or nicotinate) | 400 ug |
| Tyr-D-Arg | 15 ug |
| *Rhodiola rosea* and/or | 25 mg |
| Huperzine A | 10 ug |

Note:
While the foregoing doses are preferred, it is contemplated that the quantities of each ingredient may be varied by an order of magnitude (10% to 1000%). Because of the interactions of the various neurotransmitters, an increase in the amount of one ingredient may facilitate the reduction of another ingredient. Also, other substances of similar activity, as noted above in the text of this invention, may be substituted for those of the Example.

Example VI

Composition F and Combined Therapy

In one such example the inventors propose the combination of utilizing compositions A-E, with the patented method of treating alcohol dependence by Bonin (patent # 5,418,225 incorporated by reference into the present invention) issued in 1995.

The Bonin invention relates to a treatment for alcohol dependence involving intravenous infusion of an alcohol solution. In the present invention, the inventors propose to expand the use to all RDS behaviors. The rational here is that Bonin never appreciated the fact that alcohol like other substances of abuse such as nicotine, heroin, cocaine, marijauna, glucose to name a few, all release neuronal dopamine at the "reward site" in the brain. It is anticipated then that by using alcohol to induce dopamine release, the subject would overcome potential genetic deficits as outlined in this application and induce, for example, proliferation of dopamine D2 receptors, thereby reducing generalized craving behavior as seen in most RDS subjects. Therefore, this short-term approach may even be useful in ADHD, Tourettes, pathological gambling and even sexual deviancy.

It is the intent of the inventor to determine the potential optimal and wide spread utility of this intravenous approach as first proposed by Bonin (specific for alcohol dependence). The inventor will also determine the best composition (A-E) described herein to combine with the ethanol solution.

The Bonin invention is a method of treating alcohol dependence in which an ethanol solution is infused intravenously into a patient. Typically, for the new patient, the treatment is continued for ten days, with a steady decrease in the amount of ethanol infused each day. It is preferred that about 40–50 ml of ethanol be initially administered in two separate aliquots, and that the volume of ethanol be decreased by about 2 to 4 ml per day for the first three days. On the fourth day, the volume of ethanol is decreased by about 20 ml and this volume is given in only one aliquot. From the fourth through the tenth day, the volume is again decreased by about 2 ml per day so that on the final day, preferably only about 4 ml of ethanol is infused in one aliquot.

The preferred concentration of ethanol in solution is about 10 to 20% by volume. However, the concentration and the total volume of solution infused can vary considerably (5% to 25%), depending primarily on the tolerance and weight of the patient. One suitable alcohol solution which is available in prepackaged form is manufactured by Kendall-McGraw Laboratories, Inc. And contains 5% dextrose and 10% ethanol in distilled water.

According to the Bonin patent, it has been found that after the initial treatment program, the patients who suffer recidivism (this can be checked against genotyping the individual for multiple polymorphisms such as the DRD2A1 allele-see tables presented herein), can often be effectively retreated by a six day course of alcohol infusion, rather than the full ten day treatment program. With this shorter program, the same volume of ethanol, i.e. about 40 to 50 ml, is initially administered, and it is then decreased following the same schedule described above for the ten day treatment. On the final day treatment, preferably about 12 ml of ethanol infused.

Initial Test:

Preferred solution includes the 5% dextrose and 10% ethanol solution, begins with 220 ml of solution twice daily on the first day. At least about two and one-half hours rest or waiting period should be given between successive infusions. Following the above-described treatment on the first day, the preferred treatment schedule, using the aforementioned 10% ethanol solution, is as follows:

Day two: 200 ml, twice daily;
Day Three: 180 ml, twice daily,
Day four: 160 ml, once daily;
Day five: 140 ml, once daily;
Day six: 120 ml, once daily;
Day seven: 100 ml, once daily;
Day eight: 80 ml, once daily;
Day nine: 60 ml, once daily;
Day ten: 40 ml. Once daily.

Recidivists can often be effectively re-treated. Preferably, if using the preferred 10% ethanol solution, 220 ml is administered twice on the first day. The amount of solution infused is then reduced as follows:

Day two: 200 ml, twice daily;
Day three: 180 ml, twice daily;
Day four: 160 ml, once daily;
Day five: 140 ml, once daily;
Day six: 120 ml, once daily.

If the shorter treatment program is not effective, a longer re-treatment program can be used. Further, the volume of solution, the rate of infusion, and the concentration can all be varied with the shorter program in the same manner, and subject to the same concentrations, in which they are varied in the longer ten day program.

Is the Preamble of the Bonin Patent Limiting in its Use?

In terms of expanded use, the inventors point out that Bonin was very specific in its specified use-alcohol dependence and alcohol craving. This is stated in the preamble of the claims and throughout the text. In fact Bonin;'s proposed mechanism is strictly directed to alcoholism. He states:

"A proposed explanation for the effectiveness of this treatment is that alcohol addiction is the result of an immune response to ethanol antigen. The intestine is lined by a great number of macrophage. Phagocytization of an antigen by macrophage is usually the first step in the immune response. Thus, when alcohol is introduced intravenously, it does not pass through the macrophage-rich intestine, and the immune response is substantially ameliorated. At the same time, however, this alcohol is available in the bloodstream to satisfy the needs of the central nervous system and abate the usual [alcohol induced] withdrawal symptoms. Because the amount of alcohol administered in gradually decreased, the patient is desensitized to the alcohol antigen, which caused the allergic-type reactions. Ultimately, the patient becomes immunologically non-reactive to alcohol, and the craving for it diminishes."

Therefore, if Bonin is correct the use of intravenous alcohol alone would have no effect on other substances of abuse and addiction i.e cocaine, heroin, nicotine, glucose, marijauna as well as other ZDS behaviors (ADHD, pathological gambling, sexual deviancy etc.)

The inventor expects to find a surprising and unexpected effect of ethanol infusions to reduce cravings for other drugs of abuse; this would be indeed a patentable advance. This coupled with the outlined amino-acid, herbal and mineral combinations would also provide a novel step in the treatment of RDS behaviors with short-term bolus intravenous therapy.

| Amino Acid Precursor Formulation Daily Dose | |
|---|---|
| L-Phenylalanine | 1500 mg |
| L-Tyrosine | 900 mg |
| L-Tryptophan | 500 mg |
| L-Glutamine | 300 mg |
| Pyridoxal Phosphate | 20 mg |
| Chromium (picolinate, or nicotinate) | 400 ug |
| Tyr-D-Arg | 15 ug |
| Rhodiola rosea and/or | 25 mg |
| Huperzine A | 10 ug |
| Ethanol | 10% |

Note:
While the foregoing doses are preferred, it is contemplated that the quantities of each ingredient may be varied by an order of magnitude (10% to 1000%). Because of the interactions of the various neurotransmitters, an increase in the amount of one ingredient may facilitate the reduction of another ingredient. Also, other substances of similar activity, as noted above in the text of this invention, may be substituted for those of the Example.

It is important the inventors will carry out certain pharmaconetic studies and mass spectrophotometry on the resultant compositions, especially as it relates to the biochemical interactions, if any, with ethanol and the amino-acids, herbals and minerals contained in the final preferred compositions.

It should be understood that the forgoing terms, expressions are exemplary only and not limiting, and that the scope of protection is defined only by the claims which follow and includes all equivalents of the subject matter of the claims.

REFERENCES

The following references as well as those cited elsewhere herein are incorporated by reference herein in pertinent part to supplement this disclosure.

The &mgr; opiate receptor as a candidate gene for pain: polymorphisms, variations in expression, nociception, and opiate responses.

UhI GR, Sora I, Wang Z.

Molecular Neurobiology Branch, Intramural Research Program, National Institute on Drug Abuse, National Institutes of Health, Baltimore, Md. 21224, USA.

There are differences between human individuals and between mouse strains in levels of &mgr; opiate receptor (&mgr;OR) expression, responses to painful stimuli, and responses to opiate drugs. One of the best candidates for contributing to these differences is variation at the &mgr;OR gene locus. Support for this idea comes from analyses of the human and murine &mgr;OR genes, Assessments of Individual differences in human &mgr;OR expression add further support. Studies with mice, including knockout-tranegenle, quahtltativo trait locus, and strain-comparison studies, also strongly support the possibility that &mgr;OR gene alleles would be strong candidates for contributing to individual differences in human nocleeption and oplate drug responses. This paper reviews current analyses of the murine and human &mgr;OR genes, their Important variants, and correlations between these variants and opiate Influences on pain McI Phermacol 1999 August; 56(2):434–47

Dopamine transporter: transmembrane phenylalanine mutations can selectively influence dopamine uptake and cocaine analog recognition.

Lin Z, Wang W, Kopajtic T, Revay RS, UhI GR

Molecular Neurobiology Branch, National Institute on Drug Abuse, Intramural Research Program, National Institutes of Health, Baltimore, Md.

Cocaine blocks the normal role of the dopamine traris~porter (DAT) in terminating doparriine signaling through molecular interactions that are only partially understood. Cocaine analog structure-activity studies have suggested roles for both cationic and aromatic interactions among DAT, dopemine, and cocaine. We hypothesized that phenylalanine residues lying in putative DAT tranemombrane (TM) domains wore good candidates to contribute to aromatic and/or cationic interactions among DAT, dopamine, and cocaine. To test this idea we characterized the influences of alanine substitution for each of 29 phenylalanine residues lying in or near a putative DAT TM domain. Cells express 22 mutartts at near wild-type levels, manifest by DAT immunohistochemistry and binding of the radiolabeled cocaine analog [(3) H](−)-2-beta-carbomethoxy-3-beta-(4.fluoroph5nyl)tropane © FT), Seven mutants fail to express at normal levels. Four mutations selectively reduce cocaine analog affinities. Alanine substitutions at Phe(76), Phe(98), Phe(390), and Phe(381) located In TM domains 1 and 2, the fourth extracelkilar loop near TM 4 and In TM 7, displayed normal affinities for dopan~Ine but 3- to 8-fold reductions in affinities for CFT. One TM 3 mutation, F(155) A, selectively decreased dopamine affinity to less than 3% of wild-type levels while reducing CPT affinity less than 3-told. In a current DAT structural model, each of the residues at which alanine substitution selectivefy reduces cocaine analog or dopamine affinitIes faces a central transporter cavity, whereas mutations that Influence expression levels are more likely to lie at potential helix|helix interfaces. Specific, overlapping sets of phenylalenine residues contribute selectively to DAT recognition of dopernine and cocaine.
J Camp Neural 1999 Jul. 26;410(2):197–210
Choilnergic axon terminals in the ventral tegrnental area target a subpopulauon of neurons expressing low levels of the dopamlne transporter.
Garzon M, Vaughan RA, UMh GR, Kuhar MJ, Plcl~el VM
Department of Neurology and Neuroscience, Cornell University Medical College, New York, N.Y. iOO2i, USA. mgarzon~mell.med.comell.edu ChoHnerglc activation of dopen~lnerglc neurons In the ventral tegmental area (VTA) Is thought to play a major role in ~ognltive functions and reward. These dopamlnergic neurons differentially project to cortical and limbic forebrain regions, wheretheir.terminsls differ In levels of expression of the plasrnalemmal dopamlne transporter (DAT). ThIs transporter selectively identifies dopaminergic neurons, Whereas Itie vesicular acetyictioline transporter (yAchT) is present only In the neurons that store arid release acetyicholine. We examined Immunogold labeling for DAT and immunoperoxidase localization of VAchT antipeptlde antisera in single sections of the rat VTA to determine whether dopaminefgic someta and dendrites in this region differ In their levels of expression of DAT and/or input from cholinergic terminals. VAchT immunoreactivity was prominently localized to membranes f small synaptic veslclee In unmyelinated axons and axon terminals. VAchT-immunoreactive terminals formed almost exclusively asyrnnietnc synapse s with dendrites. Of 159 dendrites that were Identified as cholinergic targets, 36% contained plasmalemmul DAT, and 65% were without detectable DAT immunoresetivity. The DAT-immunoreactive dendrites postsynaptic to VAchT-labeled terminals contained less than half the density of gold particles as Seen in other dendrites receiving Input only from unlabeled terminals. These results suggest selectIve targetIng of cholinergic afferents in the VTA to non-dopaminergic neurons and a subpopulation of dopaminergic neurons that have a limited capacity for plasmalemmal reuptake of dopamine, a characteristic of those that project to the frontal cortex.
EurJ Phermecol 1999 Feb~366(2–3):R3–5
Visceral chemical nociception in mice lacking mu-opioid receptors: effects of morphine, SNC80 and U-50A88.
Sara I, LI XF, Funada M, Kinsey S, UhI GR
Molecular Neurobiology Branch, Intramural Research Program, National Inetituta on Drug Abuse, National Institutes of Health, Baltimore, Md. 21224, USA.

Writhing responses to Intraperitoneal acetic acid administration and their modulation by mu-, kappa- and delta-oploid receptor agonists were compared in wild-typo and mu-opioid receptor knockout mice, Unpretreated homozygous knockout mice displayed less writhing than wildtype mIce. U-50,488 [trans-3,4-dlchloro-N-methyl-N-f2-(1-pyrolldlnyl)cyclohexyIJ-b~nze neacetamide]) reduced writhing responses in wIld-type and khockouts. Morphine and SNC8O ((4)4-[9.alpha-R)-alpha-(2S,5RO-4-ellyl-2-dlmethyI-I -piperaziny 1)-3-methoxybenzylj-N. Ndiethylbenzsmide] were effective in wild-type mice but ineffective in knockouts. Mu-opioid receptors appear to play Important roles In responses to this visceral nociceptlve stimulus and rt~modulation by mu- and delta-opioid receptor agonists.
Br J Pharmacol 1999 January; 126(2):451–6
Absence of Q-protsin activation by mu-opioid receptor agonists in the spinal cord of mu-opioid receptor knockout mice.
Narita M, Mlzoguchl H, NarIta M, Sora I, Uhl GR, Teeng LF
Department of Anesthesiology, Medical College of Wisconsin, Milwaukee, 53226, USA.
1. The ability of mu-opioid receptor agonists to activate G-proteins in the spinal cord of muopicici receptor knockout mice was examined by monitoring the binding to membranes of the non-hydrolyzable analogue of GTP, guanoslne-~AE-O-(3-t35$1thIo)trIphosphate (t36S1GTPgammaS). 2. In the receptor binding study, Soatchard analysis of [3H][DAa2,NHPh4,Gly-oflenkephaiin ([3H]DAMGO; mu-opioid receptor ligand) binding revealed that the heterozygous mu-knockout mice displayed approximately 40% reductIon in the number of mu-receptors as compared to the wild-type mice, The homozygous mu-knockout mIce showed no detectable mu-bindIng sites. 3. The newly Isolated mu-opioid peptides endomorphln-1 and -2, the synthetic selective mu-opiold receptor agonist DAMGO and the prototype of mu-oploid receptor agonist morphine each produced concentration-dependent Increases In [35S]GrPgammaS binding In wild-type mice. This stimulatIon was reduced by 55–70% of the wild-type level In heterozygous, and virtually ellmInated in homozygous knockout mica. 4 No differences in the [$^{35}$S]GTPgammaS binding stimulated b~E specific deftal-([D-Pen2,5]enkephalin), delta2-([D-Ale2]deltorphin II) or kappal-(U50,A~8t-1) oploid receptor egonlets were noted In mice of any of the three genotypes.
5. The data clearly indicate that mu-opioid receptor gene products play a key role in G-prdtein actr~uation by endomorphins, DAMGO and morphine in the mouse spinal cord, fl.~y support the idea that mu-op.Oid receptor densities could be rate-limiting steps in the G-proteln activation by muoplold receptor agoniats In the spinal cord. These thus indicate a limited phyelologlcal mureeeptdr reserve. Furthermore, little change in deital-, delta2-orkappal-oplold receptor-Gprotein complex appears to accompany mu-opioid recptor gene deletions in this region.
erain Re,s 1999 Mar. 13;821(2):480–6
Characterization of mechanical withdrawal responses and effects of mu-, delta- and kappoploid agonists in normal and mu-opioid receptor knockout mace.
Fuchs PN. Raze C, Sara I. Uhi G, Rain SN
Oepartment of Neurosurgery, Johns Hopkins School of Medicine, 600 North Wolfe Stre4 Meyer 5–109, Baltimore, Md. 21257, USA. fucha°uta.edu
Clinical and expenmental observations suggest that opiates can exert different influences on the perception of stimuli from distinct sensory modallties. Thermally-induced nociception is classically responsive to opiate ugonists. mu-Opioid receptor-deficient transgenic mice are more sensitive to thermal noclceptlve stimuli a,~d morphine faile to attenuate the nocloeptive responses to thermal stimuli in these animals. To enhance our understanding of opiate Influences on mechanical sensitMty, we have examined withdrawal responses to a sequence of ascending forces of mechanIcal stimuli In mice with normal (wild type), half-normal (heterozygous) and absent (honiozygous) mu-opioid receptor levels We report data from mice examined without drug pretreatment or following pretreatment with morphine, the selective kappa-oplold agonist, U5048811, end the selective delta-opio;d agonist, DPOPE. Salinepretreated mice of e8ch genotype displayed sInIlar, mnonotonIcally increasing frequency ofwithdrawal responses to the graded stimulI. Subcut.aneously admInIstered morphine produced a dose-dependent reduction in withdrawal responses in wild type and heterozygous mice, but had no significant effect in homozygous mice. Intraventricular administration of DPDPE also reduced the frequency of paw withdrawal (FPW) in wild type mice, but not in homozygous mice. In contrast, systemic U5Ci488H produced a dose-dependent attenuation of paw withdrawal in both wild type and horriozygous mice. These findings suggest that (1) interactions of endogenous peptides with mu-opioid receptors may not play a significant role in the response to mechanical stimuli in drug-free animals, and (2) deficiency of mu-apioid receptors has no functional consequence on the response to the prototypical kappa-opiold receptor agonist, but decreases responses to the prototypical mu- and delta-opioicl receptor agonists.

Neuropsychopharmecolo9y. 1 ~99 Jan; 20(1):3–9

Molecular genetics of substance abuse vulnerability: a vurrent approach.

UhI GR

Molecular Neurobiology Branch1 NatIonal Institute on Drug Abuse, NIH, BaltImore, Md., USA.

Molecular genetics of substance abuse vulnerabilIty: a current approach.

Nuropsychopharmacology. 1999 January;20(1):3–9. Review. No abstract available.

PMID: 9885780; UI: 99103166.

Publication Types:

Review

Review, tutorial

REFERENCES

The following references, to the extent that they provide exemplary procedural or other details supplementary to those set forth herein, are specifically incorporated herein by reference.

U.S. Pat. No. 4,761,429

U.S. Pat. No. 5,189,064

Abraham, Brooks, Eylath, "The effects of chromium supplementation on serum glucose and lipids in patients with and without non-insulin-dependent diabetes," *Metabolism,* 41:768–771, 1992.

Abraham and Dufy, "Computed EEG abnormalities in panic disorder with and without premorbid drug abuse," *Biol. Psychiatry,* 29:687–690, 1991.

Accili et al., "A new look at $D_3$ receptors," *Mol. Psychiatry,* 1:93–94, 1996.

Adams et al., "Neuropsychologicla deficits are correlated with frontal hypometabolism in positron emission tomography studies of older alcoholic patients," *Alcohol Clin. Exp. Res.,* 17:205–210, 1993.

Aggleton and Mishkin, The Amygdala: Sensory gateway to the emotions, In Plutchik and Kellerman (Eds.), *Emotion Theory, Research, and Experience,* pp.281–299, NY Adacemic Press, Inc., 1986.

Allen and Gorski, Sex differences in the bed nucleus of the stria terminalis of the human brain, *J. Comp. Neurol.,* 302:697–706, 1990.

American Psychiatric Association. Diagnostic and Statistical Manual of Mental Disorders (DSM-III), Washington, D.C. 1968.

American Psychological Association, Standards for Educational and Psychological Tests (Rev. Ed.), Washington, D.C. 1974.

American Psychiatric Association. Diagnostic and Statistical Manual of Mental Disorders (DSM-IU), Washington, D.C. 1980.

American Psychological Association, Ethical Principles of Psychologists (Rev.) American Psychologist, 36:633–638, 1981.

American Psychiatric Association. Diagnostic and Statistical Manual of Mental Disorders (DSM-III-R), Washington, D.C. 1987.

American Psychiatric Association Task Force: Quantitative electroencephalography: a report on the present state of computerized EEG techniques, *Am. J. Psychiatiy,* 148(7):961–964, 19911.

American Psychiatric Association. Diagnostic and Statistical Manual of Mental Disorders (DSM-IV), Washington, D.C. 1994.

Amit and Brown, "Actions of drugs of abuse on brain reward systems: A reconsideration with specific attention to alcohol," *Pharmacology Biochemistry and Behavior,* 17:233–238, 1982.

Amsterdam et al., *Life Sci.,* 33(1):109–112, 1983.

Anderson, "Chromium and parental nutrition," *Nutrition,* 11(Suppl. 1):83–86, 1995.

Anderson, Polansky, Bryder, Canary, "Supplementalchromium effects on glucose, insulin, glucagon and urinary chrormium losses in subjects consuming controlled low-chromium diets," *Am. J. Clin. Nutr.,* 54:909–916, 1991.

Aoki, Go, Venkatesan, Kurose, "Perikaryal and synaptic localization of alpha-2A-adrenergic receptor-like immunoractivity," *Brain Res.,* 650:181–204, 1994.

Arcot, Wang, Weber, Deiniger, Batzer, "Alu repeats: a source for the genesis of primate microsatellites," *Genomics,* 29:136–144, 1995.

Arden, J. Pharm., Pharmacol 24:905–911, 1972.

Arinami, Gao, Hamaguchi, Toru, "A functional polymorphism in the promoter region of the dopamine $D_2$ receptor gene is associated with schizophrenia," *Human Molecular Genetics,* 6:577–582, 1997

Arndt-Jovin, Udvardy, Garner, Ritter, Jovin, "Z-DNA binding and inhibition by GTP of Drosophilia topoisomerase II," *Biochemistry,* 32:4862–4872, 1993.

Amsten, "Catecholamine regulation of the prefrontal cortex," *J. Psychopharmacology.* 11:151–162, 1997.

Amsten, Steere, Hunt, "The contribution of $a_2$-noradrenergic mechanism to prefrontal cortical cognitive function. Potential significance for Attention-Deficit Hyperactivity Disorder," *Arch. Gen. Psychiatry,* 53:448–455, 1996.

Asghari et al, "Modulation of intercellular cyclic AMP levels by different human dopamine $D_4$ receptor variants" *J Neurochem,* 65:1157–1165, 1995.

Ashani, Grunwald, Kronman et al., "Roles of tyrosine 337 in the binding of Huperzine A to the active site of human acetylcholinesterase, *Mol. Pharmacol.,* 45:555–560, 1994.

Ashani, Peggins, Doctor, "Mechanism of inhibition of cholinesterase by Huperzine A," *Biochem. Biophys. Res. Commun.,* 184:719–726, 1992.

Aston-Jones et al, "Discharge of noradrenergic locus coeruleus neurons in behaving rats and monkeys suggest a role in vigilance" *Progress in Brain Res.,* 88:501–520, 1991.

Aston-Jones, Foote, Bloom, "Anatomy and physiology of locus coeruleus neurons: Functional implications," M. G. Ziegler (Ed.), In: *Frontiers of Clinical Neuroscience,* Vol 2, Baltimore, Williams and Williams, 1984.

August and Garfinkel, "Behavioral and Cognitive Subtypes of AD-HD," *J. Am. Acad Child Adoles. Psychiatry,* 28(5):739–748, 1989.

August et at., "Familial subtypes of childhood hyperactivity" *J Nerv. Ment. Dis.,* 171:362–368, 1972.

Bain, et al., "Naloxone attenuation of the effect of cocaine on rewarding brain stimulation," *Life Sciences,* 40:1119–1125, 1986.

Balagot, et al., In: *Advances in pain research and therapy*, (Bowica, EUJ, et al, Raven Press, New York, 5:289–293, 1983.

Balfour and Fagerström, "Pharmacology of nicotine and its therapeutic use in smoking cessation and neurodegenerative disorders," *Pharmac. Ther.*, 72:51–81, 1996.

Balldin et al., "Further neuroendocrine evidence for reduced D, dopamine receptor function in alcoholism, *Drug Alcoh. Dep.*, 32:159–162, 1993.

Ballenger et al, "Carbamazepine in manic-depressive illness: a new treatment," *Am. J. Psychiatry*, 137:782–790, 1980.

Banerjee and Grunberger, "Enhanced expression of the bacterial chloramphenicol acetyltransferase gene in mouse cells cotransfected with synthetic polynucleotides able to form Z-DNA," *Proc. Natl. Acad. Sci. USA*, 83:4988–4992, 1986.

Banerjee, Carethers, Grunberger, "Inhibition of the herpes simplex virus thymidine kinase gene transfection in Ltk-cells by potential Z-DNA forming polymers," *Nucl. Acids Res.*, 13:5111–5126, 1985.

Beckmann, et al., *J Neuronal Trans.*, 41:123–124, 1977.

Begleiter and Potjesz, "Potential biological markers in individuals at high risk for developing alcoholism", *Alcohol Clin. Exp. Res.*, 12:488493, 1988.

Begleiter and Porjesz, "Neuroelectric processes in individuals at risk for alcoholism," *Alcohol and Alcoholism*, 25:251–256, 1990.

Behnke and Wilmore, In: *Evaluation and Regulation of Body Build and Composition, Englewood Cliffs*; NJ, Prentice-Hall, 1974.

Benjamin, Li, Patterson, Greenberg, Murphy, Hamer, "Population and familial association between the D4 dopamine receptor gene and measures of novelty seeking," *Nature Genet.*, 12:81–84, 1996.

Bennett, Lucassen, Grough, Pewell, Undlien, Pritchard, Merriman, Kawaguchi, Dronsfeld, Pociot, Nerup, Bouzekri, Cambon-Thomsen, Ronning, Barnett, Bain, Todd, "Susceptibility to human type I diabetes at IDDM2 is determined by tandem repeat variation at the insulin gene minisatellite locus," *Nature Genet.*, 9:284–292, 1955.

Benuck, et al., *Biophys. Res. Comm.*, 107:1123–1129, 1982.

Berman et al., "EP reduced viso-spatial performance in children with the $D_2$ dopamine receptor $A_1$, allele" *Behav. Genet.*, 25:45–58, 1995.

Bernad, "EEG and pesticides," *Electroencephalography and Clinical Neurophysiology*, 20:IX-X, 1989.

Beyer and Feder, Sex steroids and afferent input: their roles in brain sexual differentiation, *Annu. Rev. Physiol.*, 49:349–364, 1987.

Biederman et al, "Evidence of familial association between attention disorder and major affective disorders" *Arch. Gen. Psychiatry*, 48:526–533, 1990a Biederman, Faraone, Keenan, Knee, Tsuang, "Family-genetic and psychosocial risk factors in DSM-III attention deficit disorder," *J. Amer. Acad Child Adolescent Psychiat.*, 29:526–533, 1990b.

Biederman, Newcom, Sprich, Comorbidity of attention deficit hyperactivity disorder with conduct, depressive, anxiety, and other disorders, *Am. J. Psychiatry*, 148:564–577, 1991.

Biederman, Faraone, Spencer, Wilens, Norman, Lapey, Mick, Lehman, Doyle, "Patterns of psychiatric comorbidity, cognition, and psychosocial functioning in adults with attention deficit hyperactivity disorder," *Am. J. Psychiatry*, 150:1792–1798, 1993.

Biggio et al, "Stimulation of dopamine synthesis in caudate nucleus by intrastiatial enkephalins and antagonism by naloxone," *Science*, 200:552–54, 1978.

Black, Chenz, Craig, Powell, "Dinucleotide repeat polymorphism at the MAOA locus," *Nucleic Acids Res.*, 19:689, 1991.

Blackburn and Kanders, eds., In: *Obesity Pathophysiology, Psychology and Treatment*, Chapman and Hall Series in Clinical Nutrition, New York, N.Y., Chapman and Hall, 1994.

Bloom et al., *Proc. Natl. Acad. Sci., USA*, 75:1591–1595, 1978.

Bloom, In: *The Pharmacological Basis Of Therapeutics*, 247–248, (Goodman, et al., eds., 1985).

Blum, Wallace, Geller, "Synergy of ethanol and putative neurotransmitters: Glycine and serine," *Science*, 176:292–294, 1972.

Blum, Hamilton, Wallace, *Alcohol and opiates: A review of common neurochemical and behavioral mechanisms*, Editor: K. Blum, (pp. 203), Academic Press, New York, 1977.

Blum et al., "Methionine enkephalinase as a possible neuromodulator of regional cerebral blood flow," *Experimentia*, 41:932–933, 1985.

Blum, Allison, Trachtenberg, Williams, Loeblich, "Reduction of both drug hunger and withdrawal against advice rate of cocaine abusers in a 30-day inpatient treatment program by the neuronutrient Tropamine," *Current Therapeutic Research*, 43:1204–1214, 1988.

Blum, "A commentary on neurotransmitter restoration as a common mode of treatment for alcohol, cocaine and opiate abuse," Integrative Psychiatry, 6:199–204, 1989a.

Blum, Briggs, Trachtenberg, "Ethanol ingestive behavior as a function of central neurotransmission (Review)," Experientia, 45:444452, 1989b.

Blum, Trachtenberg, Elliott, Dingler, Sexton, Samuels, Cataldie, "Enkephalinase inhibition and precursor amino acid loading improves inpatient treatment of alcohol and polydrug abusers: Double-blind placebo-controlled study of the nutritional adjunct," *SAAVE. Alcohol.* 5:481–493, 1989c.

Blum and Kozlowski, "Ethanol and neuromodulator interactions: A cascade model of reward," Ollat et al. (Eds), In: *Progress Alcohol Research II* (pp. 131–149), VSP Utrecht, 1990a.

Blum, Noble, Sheridan, Montgomery, Ritchie, Jagadeeswaren, Nogami, Briggs, Cohns, "Allelic association of human dopamine $D_2$ receptor gene in alcoholism," *Journal of the American Medical Association*, 263:2055–2060, 1990b.

Blum, Trachtenberg, Cook, "Neuronutrient effect on weight loss in carbohydrate bingers: an open clinical trial," *Current Therap. Res.*, 48:217–223, 1990c.

Blum and Payne, *Alcohol and the Addictive Brain*, Free Press, New York, 1991 a

Blum, Noble, Sheridan, Finley, Montgomery, Ritchie, Ozkavagoz, Fitch, Sadlack, F., Sheffield, Dahlmann, Halbardier, Nogami, "Association of the A1 allele of the $D_2$ dopamine receptor gene with severe alcoholism," *Alcohol*, 8:407416, 1991b.

Blum, Noble, Sheridan, Montgomery, Ritchie, Ozkavagoz, Fitch, Wood, Finley, Sadlack, "Genetic predisposition in alcoholism: association of the $D_2$ dopamine receptor TaqI $B_1$ RFLP with severe alcoholism," *Alcohol*, 10:59–67, 1993.

Blum, Braverman, Dinardo, Wood, Sheridan, "Prolonged P300 latency in a neuropsychiatric population with the $D_2$ dopamine receptor $A_1$ allele," *Pharmacogenetics*, 4:313–322, 1994a.

Blum et al, "Prolonged P300 latency in a neuropsychiatric polulation with the D₂ dopamine A, allele," *Pharmacogenetics*, 4:313–322, 1994b.

Blum, Braverman, Wood, et al., "Increased prevalence of the TaqI A₁ of the dopamine receptor gene (DRD2) in obesity with comorbid substance use disorder: a preliminary report," *Pharmacogenetics*, 6:297–305, 1995a Blum, Sheridan, Wood, Braverman, Chen, Comings, "Dopamine D₂ receptor gene variants: Association and linkage studies in impulsive-addictive-compulsive behaviors," *Pharmacogenetics*, 5:121–141, 1995b.

Blum, Cull, Braverman, Comings, "Reward deficiency syndrome," *Am. Scientist*, 114:132–145, 1.996a Blum et al, "Reward deficiency syndrome," American Scientist, 84:132–145, 1996.

Blum et al., "The D₂ dopamine receptor gene as a determinant of reward deficiency syndrome," *J Royal Soc. Of Med.*, 89:396–400, 1996b.

Blum et al., "Increased prevalence of the TaqI A, allele of the dopamine receptor gene (DRD2) in obesity with comorbid substance use disorder: a preliminary report," *Pharmacogenetics*, 6:297–305, 1996c.

Blum, Braverman, Wu, Cull, etal., "Association of polymorphisms of dopamine D₂receptor (DRD2) and dopamine transporter (DAT1) genes with Schizoid Avoidant behaviors (SAB)," *Molecular Psychiaty*, 2:239–246, 1997a.

Blum, Cull, Chen, et al, "Clinical evidence for effectiveness of Phencal in maintaining weight loss in an open label controlled 2-year study," *Current Therap. Res.*, 58:745–763, 1997b.

Blum et al, "Generational Association Studies of Dopaminigic Genes in Attention-Deficit-Hyperactivity (ADHD) probands of Multiple Family Members up to four Generations," *J. Neurotherapy [Abstract]*, 1998.

Bradford and McClean, Sexual offenders, violence and testosterone: A clinical study, *Can. J. Psychiatry*, 29:335–343, 1984.

Braun, Little, Reuter, Müller-Mysok, Köster, "Improved analysis of microsatellites using mass spectrometry," *Genomics*, 46:18–23, 1997a.

Braun, Little, Köster, "Detecting CFTR gene mutations by using primer oligo base extension and mass spectrometry," *Clin. Chem.*, 43:1151–1158, 1997b.

Braverman, "Brain electrical activity mapping in treatment resistant schizophrenics," *Journal of Orthomolecular Medicine*, 5:4648, 1990a.

Braverman et al., "A commentary on brain mapping in 60 substance abusers: can the potential for drug abuse be predicted and prevented by treatment?" *Cur. Ther. Res.*, 48:549–585, 1990b.

Braverman, Smith, Smayda, Blum, "Modification of P300 amplitude and other electrophysiological parameters of drug abuse by cranial electrical stimulation," *Current Therapeutic Research*, 48:586–596, 1990c.

Braverman and Blurn, "Substance use disorder exacerbates brain electrophysiological abnormalities in a psychiatrically-ill population," *Clin. EEG.*, 27(4supplement): 1028, 1996a.

Braverman and Blum, "Substance use disorder exacerbates brain electrophysiological abnormalities in a psychiatrically ill population" 148 Annual American Psychiatric Society, New York 1996b (Abstract).

Brown, Ebert, Goyer, Jimerson, Klein, Bunney, Goodwin, Aggression, suicide and serotonin relationships to CSF amine metabolism, *Amer. J Psychiat.*, 139:741–746, 1982.

Brown, "Teacher ratings and the assessment of attention deficit disordered children," *J. Learn. Disabil.*, 19(2):95–100, 1986.

Brown, Goss, Lubahan, Joseph, Wilson, French, Willard, Androgen receptor locus on the human X chromosome: regional localizatin to Xq11-12 and description of a DNA polymorphism, *Am. J. Hum. Genet.*, 44:264269, 1989.

Brown, Blum, Tractenberg, "Neurodynamics of release prevention: A neuronutrient approach to outpatient DUI offenders," *J. of Psychoactive Drugs*, 22(2), 173–187, 1990.

Brown et al., "Alcoholism and affective disorder: clinical course of depressive symptoms," *Am. J. Psychiatry*, 152:45–52, 1994.

Bruckner and Hausch, "Amino acids as ubiquitous constituents in fermented foods, G. Lubec and Rosenthal (Eds.), In: *Amino Acids—Chemistry, Biology and Medicine*. (pp. 1172–1182). Leiden: ESCOM Science Publication.

Brunner, Nelen, van Zandvoort, Abeling, van Gennip, Wolters, Kuiper, Ropers, van Oost, "X-linked borderline mental retardation with prominent behavioral disturbance: phenotype, genetic localization and evidence for disturbed monoamine metabolism," *Am. J. Hum. Genet.*, 52:1032–1039, 1993.

Brunner, Helen, Breakefield, Ropers, van Oost, "Abnormal behavior linked to a point mutation in the structural gene for monamine oxidase A," *Psychiat. Genet.*, 3:122, 1993.

Buchsbaum, Coursey, Murphy, "The biochemical high-risk paradigm: behavioral and familial correlates of low platelet monoamine oxidase activity," *Science*, 194:339–341, 1976.

Buchsbaum, Haier, Murphy, "Suicide attempts, platelet monamine oxidase and the average evoked response," *Acta Psychiatr. Scand*, 56:69–79, 1977.

Buchsbaum, Rigal, Coppola, Cappelletti, King, Johnson, "A new system for gray-level surface distribution maps of electrical activity," *Electroencephalography and Clinical Neurophysiology*, 53:237–242, 1982.

Buchsbaum and Wender, "Average evoked responses in normal and minimally brain dysfunctional children treated with amphetamine," *Archives of General Psychiatry*, 29:764–770, 1993.

Bulbulian, Pringle, Liddy, "Chromium picolinate supplementation in male and female swimmers," *Med. Sci. Sports Exerc.*, 28:s11 (abstract), 1996.

Burke, Enghild, Martin, Jou, Myers, Roses, Vance, Strittmatter, "Huntington and DRPLA proteins selectively interact with the enzyme GAPDH," *Nature Med.*, 2:347–350, 1996.

Butler et al., "Biogenic amine metabolism in Tourette syndrome" *Ann. Neurol*, 37–39, 1979.

Butzow, Shin, Eichhorn, "Effect of template conversion from the B to the Z conformation on RNA polymerase activity," *Biochemistry*, 23:48374843, 1984.

Cabot and Serfontein, "Quantitative electroencephalographic profiles of children with Attention Deficit Disorder," *Biol. Psychiatry*, 40:951–963, 1996.

Cadoret et al., "Psychopathology in adopted away of biological parents with antisocial behavior," *Arch. Gen. Psychiatry*, 35:175–184, 1978.

Cahill, Ernst, Janknecht, Nordheim, "Regulatory squelching," *FEBS Lett.*, 344:105–108, 1994.

Campuzano, Montemini, Moltò, Pianese, Cosséé, Cavalcanti, Monros, Rodius, Ducilos, Monticelli, Zara, Cafizares, Koutnikoa, Bidichandani, Gellera, Brice, Trouillas, Michele, Filla, Frutos, Palau, Patel, DiDonate, Mandel, Cocozza, Koenig, Pandolfo, "Friedreich's ataxia: autosomal recessive disease caused by an intronic GAA triplet repeat expansion," *Science*, 271:1423–1427, 1996.

Cantwell, "Psychiatric illness in the families of hyperactive children," *Arch. Gen. Psychiatry*, 27:414–417, 1972.

Capon, Chen, Levinson, Seeburg, Goeddel, "Complete nucleotide sequences of the T24 human bladder carcinoma oncogene and its normal homologue," *Nature*, 302:33–37, 1983.

Carenzie, Biasini, Frigeni, Della Bella, "On the enzymatic degradation of enkephalins: Pharmacological implications", In: *Neural peptides and neuronal communication*, E. Costa and M. Trabucci (Eds)., (pp. 237–246), New York: Raven press, 1980.

Carey and Williamson, "Linkage analysis of quantitative traits: increased power by using selected samples," *Am. J. Hum. Genet.*, 49:786–796, 1991.

Caskey, Pizzuti, Fu, Fenwick, Nelson, "Triplet repeat mutations in human disease," *Science*, 256:784–789, 1992.

Cassel et al., "Serotonergic modulation of cholinergic function in the central nervous system: cognitive implications," *Neurosci*, 69:141, 1995.

Castellanos et al., "Cerebrospinal fluid homovanillic acid predicts behavioral response to stimulants in 45 boys with attention deficit/hyperactivity disorder," *Neuropsychopharmacology*, 14:125–137, 1996.

Castelli, Garrison, Wilson, Abbott, Kalousdian, Kannel, "Incidence of coronary heart disease and lipoprotein cholesterol levels," *JAMA*, 256:2835–2838, 1986.

Chamberlain, Driver, Miesdeld, The length and location of CAG trinucleotide repeats in the androgen receptor N-terminal domain affect transactivation function, *Nucleic Acids Res.*, 22:3181–3186, 1994.

Cheng, Ren, Tang, "Huperine A, a novel promising acetylcholinesterase inhibitor," *Neuroreport*, 8:97–101, 1996.

Choong, Kemppainen, Zhou, Wilson, Reduced androngen receptor gene expression with first exon CAG repeat expansion," *Molec. Endocr.*, 10:1527–1535, 1996.

Christian et al., "Associations of dopamine $D_2$ polymorphisms with brain electrophysiology," *Alcoholism*, 18:178, 1994.

Clancy, Clarkson, DeCheke, Nosaka, Freedson, Cunningham, Valentine, "Effects of chromium picolinate supplementation on body composition, strength, and urinary chromium loss in football players," *Inter. J. Sport Nutr.*, 4:142–153, 1994.

Cloninger et al., "Psychobiological model or temperament and character," *Arch. Gen. Psych.*, 50:975–990, 1993.

Cloninger, "Genetic and environmental factors in the development of alcoholism" *J. Psychiat. Treat. Eval.*, 5:487496, 1983.

Cloninger and Gottesman, Genetic and environmental factors in antisocial behavioral disorders. In *Mednick; Moffitt, Stack* (Eds.), *The Causes of Crime* (pp. 92–109). New York, N.Y., Cambridge Univ. Press, 1986.

Cloninger, "$D_2$ dopamine receptor gene is associated bu not linked with alcoholism," *JAMA*, 266:1833–1834, 1991.

Clouet, "A biochemical and neurophysicalogical comparison of opioids and antipsychotics, *Annals New York Acad. of Sci.*, 398:130–137, 1982.

Clouet et al, "Catecholamine bisynthesis in brains of rats treated with morphine," *Science*, 168:854–855, 1970.

Coccaro, Central serotonin and impulsive aggression, *Br. J. Psychiatry*, 155 (suppl 8):52–62, 1989.

Cochran, "Some methods for strengthening the common $X^2$ tests," Biometrics, 10:417–454, 1954.

Coetzee and Ross, Prostate cancer and the androgen receptor," *J. Nat. Cancer Inst.*, 86:872–873, 1994.

Coffey, *Prostate Cancer. UICC Technical Report Series Vol* 48. Geneva: International Union Against Cancer. 1979.

Coger, Moe, Serafetinides, "Attention deficit disorder in adults and nicotine dependence: Psychobiological factors in resistance to recovery," *J. Psychoactive Drugs*, 28:229–240, 1996.

Cohen et al, "Central biogenic amine metabolism in children with the syndrome of chronic multiple tics of Gilles de la tourette: Norepinephrine, serotonin and dopamine," *J. Am. Acad. Child Psychiatry*, 118:320–341, 1979.

Cohen, Semple, Gross, Nordahl, DeLisi, Holcomb, King, Morihisa, Pickar, "Dysfunction in a prefrontal substrate of sustained attention in schizophrenia," *Life Sciences.*, 40:2031–2039, 1987a.

Cohen, Walter, Levinson, "A repetitive sequence element 3' of the human c-Ha-ras, gene has enhancer activity," *J. Cell. Physiol.*, 5:75–81, 1987b.

Collick, Dunn, Jeffreys, "Minisatellite binding protein Msbp-1 is a sequence-specific single-stranded DNA-binding protein," *Nucl. Acids Res.*, 19:6399–6404, 1991.

Collier, Stöber, Li, Heils, Catalano, DiBella, Arranz, Murray, Vallada, Bengel, Müller, Roberts, Smeraldi, Kirov, Sham, Lesch, "A novel functional polymorphism within the promoter of the serotonin transporter gene: possible role in susceptability to affective disorders," *Molecular Psychiatry*, 1:453–460, 1996

Comings and MacMurray, "Molecular heterosis," 1977.

Comings and Comings, "Tourette's syndrome and attention deficit disorder with hyperactivity: Are they genetically related." *J. Am. Acad. Child Psychiatry*, 23:138–146, 1984.

Comings and Comings, "A controlled study of Tourette syndrome. I–VII," *Am. J. Hum. Genet.*, 41':701–866, 1987.

Comings and Comings, "A controlled study of Tourette syndrome. I. Attention-deficit disorder, learning disorders, and school problems," *Am. J. Hum. Genet.*, 41:701–741, 1987.

Comings and Comings, A controlled family history study of Tourette syndrome. I. Attention deficit hyperactivity disorder, learning disorders and dyslexia, *J. Clin. Psychiat.*, 51:275–280, 1990a.

Comings, In: *Tourette Syndrome and Human Behavior*, Hope Press: Duarte, Calif., pp 1–828, 1990b.

Comings, Comings, Tacket, and Li, "The clonidine patch and behavioral problems," *J. Am. Acad. Child. Adolesc. Psychiatry.*, 29:667–668, 1990c.

Comings, Comings, Muhleman, Dietz, Shahbahrami, Tast, Knell, Kocsis, Baumgarten, Kovacs, Levy, Smith, Kane, Lieberman, Klein, MacMurray, Task, Sverd, Gysin, Flanagan, "The dopamine $D_2$ receptor locus as a modifying gene in neuropsychiatric disorders," *J. Am. Med. Assn.*, 266:1793–1800, 1991.

Comings et al., "Association between Tourett's syndrome and homozygosity at the dopamine-$D_3$ receptor gene," *Lancet*, 341:906, 1993a.

Comings and Comings, "Comorbid Behavioral Disorders," R Kurlan (Ed.), In: *Handbook of Tourette's Syndrome and Related Tic and Behavioral Disorders*, pp. 111–147, New York: Marcel-Decker, 1993b.

Comings, "Genetic factors in substance abuse based on studies of Tourette syndrome and ADHD probands and relatives. I. Drug abuse," *Drug and Alcohol Dependence*, 35:1–16, 1994a Comings, "Genetic factors in substance abuse based on studies of Tourette syndrome and ADHD probands and relatives. II. Alcohol abuse," *Drug and Alcohol Dependence*, 35:17–24, 1994b.

Comings, The role of genetic factors in human sexual behavior based on studies of Tourette syndrome and ADHD probands and their relatives, *Am. J. Med. Gen. (Neuropsych. Genet.)*, 54:227–241, 1994c.

Comings, "Candidate genes and association studies in psychiatry," (Letter to the editor), *Am. J. Med. Gen. (Neuropsych. Genet.)*, 54:324, 1994d.

Comings, Muhleman, Ahn, Gysin, Flanagan, "The dopamine D2 receptor gene: a genetic risk factor in substance abuse," *Drug Alcohd Depend.*, 214:175–180, 1994e.

Comings, "The role of genetic factors in conduct disorder based on studies of Tourette syndrome and ADHD probands and their relatives," *J. Dev. Behav. Pediatr.*, 16:142–157, 1995a Comings, "Tourette syndrome: A hereditary neuropsychiatric spectrum disorder," *Ann. Clin. Psychiatr*, 6:235–247, 1995b.

Comings, "Genetic factors in depression based on studies of Tourette syndrome and Attention Deficit Hyperactivity Disorder probands and relatives, *Am. J. Med. Gen. (Neuropsych. Genet.)*, 60:111–121, 1995c.

Comings, "The haplotype relative risk technique lacks power in polygenic inheritance," 1995 *World Congress Psychiatric Genetics*, 5:103, 1995d.

Comings et al., "Susuptability to post-tramatic stress disorder: a study of replication.," *Biochmeistry*, 40:368–372, 1996a.

Comings et al, "A study of the dopamine $D_2$ receptor in pathological gambling," *Pharmacogenetics*, 6:223–234, 1996b.

Comings, Gade, Muhleman, MacMurray, "Role of the HTRIA serotonin receptor gene in Tourette syndrome and conduct disorder," *Psychiat. Genet.*, 6:166, 1996c.

Comings, MacMurray, Gade, Muhleman, Peters, "Genetic variants of the human obesity gene: association with psychiatric symptoms and body mass index in young women, and interaction with the dopamine D2 receptor gene," *Mol. Psychiatry*, 1:325–335, 1996d.

Comings, Muhleman, Gade, Chiu, Wu, Dietz, Winn-Dean, Ferry, Rosenthal, Lesieur, Rugle, Sverd, Johnson, MacMurray, "Exon and intron mutations in the human tryptophan 2,3-dioxygenase gene and their potential association with Tourette syndrome, substance abuse and other psychiatric disorders," *Pharmacogenetics*, 6:307–318, 1996e.

Comings, Wu, Chiu, Muhleman, Sverd, "Studies of c-Harvey-Ras gene in psychiatric disorders," *Psychiatry Res.*, 63:25–32, 1996f Comings, Wu, Chiu, Ring, Dietz, and Muhleman, "Polygenic inheritance of Tourette syndrome, stuttering, ADHD, conduct and oppositional defiant disorder: The Additive and Subtractive Effect of the three dopaminergic genes-DRD2, DbH and DAT1," *Am. J. Med. Gen. (Neuropsych. Genet.)*, 67:264–288, 1996j.

Comings, "Polygenic inheritance and minisatellites," *Psychiat. Genet.*, 6:157–158, 1996k.

Comings, "Polygenetic inheritance of psycatric disorders," In: *Handbook of Psychiatric Genetics*, Blum K., Noble EP, Sparks RS, Sheridan PJ (Eds), CRC Press, Boca Raton, Fla., pp 235–260, 19961.

Comings, In: *Search for the Tourette Syndrome and Human Behavior Genes*, Hope Press: Duarte., CA, 1996m.

Comings, Gade, Wu, Chiu, Dietz, Muhleman, Saucier, Ferry, Burchete, Johnson, Verde, MacMurray, "Studies of the potential role of the dopamine $D_1$ receptor gene in addictive behaviors," *Mol. Psychiatry*, 2:4456, 1997a Comings, Muhleman, Gade, Johnson, Verde, Saucier, MacMurray, "Cannabinoid receptor gene (CNR1): association with IV drug use," *Mol. Psychiatry*, 2:161–168, 1997b.

Comings, Wu, Gonzalez, Muhleman, Gade, Blake, MacMurray, McGue, Lykken, "Association of the normal FRAXA and HTR2A genes with performance IQ in the general population," 1997.

Comings, "Polygenic inheritance and micro/minisatelites," *Mol. Psychiatry*, 3:21–31, 1998.

Conners, Levin, Sparrow, Hinton, Erhardt, Meck, Rose, March, "Nicotine and attention in adult attention deficit hyperactivity disorder (ADHD)," *Psychopharmacol. Bull.*, 32:67–73, 1996.

Cook, Stein, Krasowski, Cox, Olkon, Kieffer, Leventhal, "Association of attention-deficit disorder and the dopamine transporter gene," *Am. J. Hum. Genet.*, 56:993–998, 1995.

Corbetta, Miezin, Dobmeyer, Shulman, Petersen, "Selective and divided attention during visual discriminations of shape, color, and speed: functional anatomy by positron emission tomography," *Journal of Neuroscience.*, 11:2383–2402, 1991.

Corrigall and Coen, "Nicotine maintains robust self-administration in rats on a limited-access schedule," *Psychopharmacology (Berlin)*, 99:473478, 1989.

Corrigall and Coen, "Selective Dopamine Antagonists Reduce Nicotine Self-Administration," *Psychopharmacology (Berlin)*, 104:171–176, 1991.

Corrigall, Coen, Adamson, "Self-administered nicotine activates the mesolimbic dopamine system through the ventral tegmental area," *Brain Res.*, 653:278–284, 1994.

Costello, "A Report on the NIMH Diagnostic Interview Schedule for Children (DISC)," Paper presented at the Research Forum: Structured diagnostic instruments in child psychiatry, *Am. Acad. Child Psychiatry*, San Francisco, Calif., 1983.

Coy and Kastin, *J. Peptides*, 1:175–177, 1980.

Craddock, Daniels, Roberts, Rees, McGuffin, Owen, "No evidence for allelic association between bipolar disorder and monoamine oxidase A gene polymorphisms," *Am. J. Med., Gen. (Neuropsych. Genet.)*, 60:322–324, 1995.

Crocq et al., "Association between schizophrenia and homozygosity at the dopamine $D_3$ receptor gene," *J. Med. Genet.*, 29:858–860, 1992.

Curtis, Lehman, Zamore, "Translational regulation in development," *Cell*, 81:171–178, 1965.

d'Amato, Leboyer, Malafosse, Samolyk, Lamouroux, Junien, Mallet, "Two TaqI dimorphic sites at the human b-hydroxylase locus," *Nucleic Acids Res.*, 17:5871, 1989.

Davidson, *Clinical Diabetes Mellitus*, New York, N.Y., Thieme Medical Publishers, Inc., 1991.

Davis, Hurt, Morse, O'Brien, "Discrimanant analysis of the self-administered alcoholism screening test," *Alcoholism: Clinical & Experimental Research*, 11:269–273, 1987.

DeFrance, Schweitzer, Sands, Ginsberg, Sharma, "Age-Related Changes of Cognitive ERPs in Attention, 1995.

DeFrance, Ginsberg, Rosenberg, Sharma, "Topographical mapping of adolescent affective disorders," 1995

DeFrance, Hymel, Degioanni, Kutyna, Calkins, Estes, Schweitzer, "Evidence of temporal lobe activation by discriminative spatial orientation," *Brain Topography*, 6:137–142, 1993.

del Senno, Aguiari, Piva, Dinucleotide repeat polymorphism in the human estrogen receptor (ESR) gene, *Hum. Mol. Genet.*, 1:354, 1992.

Della Bella, Carenzie, Frigeni, "Effect of carboxypeptidase inhibition on in vitro and in vow pharmacological properties of morphine enkephalins," *Neuropharmacology*, 18:719–721, 1979.

Dementyeva and Yaremenko, Bul. Sib. Dep. Of the Academy of Science of the USSR, 6:7077, 1983.

Devor, Cloninger, Hoffman, Tabakoff, "Association of monoamine oxidase (MAO) activity with alcoholism and alcoholic subtypes," *Am. J. Med. Genet.*, 48:209–213, 1994.

*Diagnostic and Statistical Manual of Mental Disorders,* 3rd Ed, revised, American Psychiatric Association: Washington, D.C., 1987.

*Diagnostic and Statistical Manual of the American Psychiatric Assn.* IV. Washington, D.C.: American Psychiatric Assn., 1994.

DiChiara and Imperato, "Drugs abused by humans preferentially increase synaptic dopamine concentrations in the mesolimbic system of freely moving rats," *Proc. Natl. Acad. Sci. USA,* 85:5274–5278, 1988.

Dienstbier, "Arousal and physiological toughness: Implication for mental and physical health", *Psychological Rev.,* 96:84–100, 1989.

Djordjevic, Dimitrijevic, Maksimovic, Vivic, Vucetic, "Application of organic bound chrome in disturbed glycoregulation therapy," Transplant. Proc., 27:3333–3334, 1995.

Donaldson, Lee, Smith, Rennefl, "Glucose tolerance and plasma lipid distribution in rats fed a high sucrose, high cholesterol, low Cr diet," *Metabolism,* 34:1086–1093, 1985.

Donchin, Callaway, Cooper, Desmedt, Goff, Hillyard, Suton, "Publication criteria for studies of evoked potentials (EP) in man. Report of the methodology committee," Desmedt (Ed.), In: *Attention, voluntary contraction and event related cerebral potentials,* Progress in clinical neurophysiology, (pp. 1–11), Basel, Karger, 1977.

Donnelly, Rapoport, Potter, Oliver, Keysor, Murphy, "Fenfluramine and dextroamphetamine treatment of childhood hyperactivity," *Arch. Gen. Psychiatry,* 46:205–212, 1989.

Duffy et al., "Status of quantitative EEG (QEEG) in clinical practice," *Clinical EEG,* 25(1), 1994.

Duffy, Albert, McAnulty, "Brain electrical activity in patients with presenile and senile dementia of the Alzheimer Type," *Annals of Neurology,* 16:439–448, 1984.

Duffy, Bartels, Burchfield, "Significance Probability Mapping: An Aid in the Topographical Analysis of Brain Electrical Activity," *Electroencephalography and Clinical Neurophysiology,* 51:455462, 1981.

Durstine and Haskell, "Effects of exercise training on plasma lipids and lipoproteins," In: *Exercise and Sport Sciences Reviews,* Volume 22, J. O. Holloszy (ed), Baltimore, Md., Williams and Wilkins, 1994.

Dykman, Ackerman, Oglesby, "Selective and sustained attention in hyperactive learning disabled and normal boys," *J. Nerv. Ment. Dis.,* 167:288–297, 1979.

Ebstein, Novick, Umansky, Priel, Osher, Blaine, Bennett, Nemanov, Katz, Belmaker, "Dopamine D4 receptor (D4DR) exon III polymorphism associated with the human personality trait of novelty seeking," *Nature Genet.,* 12:78–80, 1996.

Eckel, "Insulin resistance: an adaption for weight maintenance," *Lancet* 340:1452–1453, 1992.

Edwards, Hammond, Jin, Caskey, Chakaborty, Genetic variation at five trimeric and tetameric tandem repeat loci in four human population groups, *Genomics,* 12:241–253, 1992.

Egger and Flytin, Effects of electrical stimulation of the amygdala on hyopthalamically elicited attack behavior in cats, *J. Neurophysiol.,* 26:705–720, 1963.

Eggers, Kurth, Kurth, "Allele frequencies of dopamine receptors DRD$_1$ and DRD$_2$ in Parkinson's disease populations," *Am. J. Hum. Genet.,* 57:A162, 1995.

Ehrenpreis et al., In: *Advances in endogenous and exogenous opioids*: Proc. Intl. Narcotic Res. Conf., Kodancha, Tokyo, 279–281, 1981.

Ehrenpreis, Balagot, Comaty, Myles, "Naloxone reversible analgesia in mice produced by D-phenylalanine and hydrocinnamic acid, inhibitors of carboxypeptidase A," Bonica et al. (Eds.), In: *Advances in pain and research therapy* (pp 479488). New York: Raven Press, 1979.

Ehrenpreis et al., *Pharmacologist* 20:168, 1978

Epplen, Kyas, Mäueler, "Genomic simple repetitive DNAs are targets for differential binding of nuclear proteins," *FEBS Lett.,* 389:92–95, 1996.

Evans, "The role of picolinic acid in mineral metabolism," *Life Chem. Rpts.,* 1:5767, 1982.

Evans and Press "Cholesterol and glucose lowering effect of chromium picolinate," *FASEB. J.,* 3:A3101, 1989a Evans, "The effect of chromium picolinate on insulin controlled parameters in humans," *Int. J. Biosoc. Med. Res.,* 11:163–180, 1989b.

Evans and Bowman, "Chromium picolinate increases membrane fluidity and rate of insulin internalization," *J. Inorgan. Biochem.,* 46:243–250, 1992a.

Evans and Meyer, "Chromium picolinate increases longevity," *Age,* 15:134, 1992b.

Evans and Pouchnik, "Composition and biological activity of chromium-pyridine carboxylate complexes," *J. Inorg. Biochem.,* 49:177–187, 1993a.

Evans, "Chromium picolinate is an efficacious and safe supplement," *Int. J. Sport Nutr.,* 3:117–122, 1993b.

Falk and Rubinstein, "Haplotype relative risks: an easy reliable way to construct a proper control sample for risk calculations," *Ann. Hum. Genet.,* 51:227–233, 1987.

Farde et al., "D$_2$ dopamine receptors and personality traits" *Nature,* 385:590, 1997.

Farone et al., "Evidence for the independent famial transmission of attention deficit hyperactivity disorder and learning disabilities: Results from a family genetic study," *Am. J. Psychiatry,* 150:891–895, 1993a.

Farone et al., "Family-genetic and psycholsocial risk factors in DSMIII attention deficit disorder," *Am. J. Psychiatry,* 150:1792–1798, 1993b.

Felig, "Amino acid metabolism in man," *Ann. Rev. Biochem.,* 44:933–955, 1975.

Felig, "Insulin is the mediator of feeding-related thermogenesis: Insulin resistance and/or deficiency results in a thermogenic deficit which contributes to the pathogenesis of obesity," *Clin. Physiol.* 4:267–273, 1984.

Fernstrom and Wurtman, *Science,* 174:1023, 1971.

Fink, Bores, Effland et al., "Synthesis and evaluation of 5-amino-5,6,7,8-tetrahydroquinolinones as potential agents for the treatment of Alzheimer's disease," *J. Med. Chem.,* 38:3645–3651, 1995.

Fitz et al., *J. Am. Soc. Pharmacol. Therap.,* 271:1574–1582, 1994.

Fowler, Tipton, MacKay, Youdin, "Human platelet monoamine oxidase-a useful enzyme in the study of psychiatric disorders," *Neuroscience,* 7:1577–1594, 1982.

Friedman, Carson, Larsson, DeMarco, A polymorphism in the coding region of the vasopressin type 2 receptor (AVPR$_2$) gene, *Hum. Mol. Genet.,* 2:1746, 1993.

Gade, Blake, MacMurray, Muhleman, Johnson, Verde, Comings, "Relationship of the GABRB$_3$ gene to adult ADHD and personality traits in Caucasian and African-American samples," *Psychiat. Genet.,* 6:164–165, 1996.

Gade, Muhleman, Blake, MacMurray, Johnson, Verde, Saucier, McGue, Lykken, Comings, "Correlation of length of VNTR alleles are the X-linked MAOA gene and phenotypic effect in Tourette syndrome and drug abuse," *Mol. Psychiatry,* 3:50–60, 1997.

Gadow and Sprafkin, In: *Child Symptom Inventories Manual,* Checkmate Plus Ltd: Stony Brook, N.Y., pp 1–115, 1994.

Gail et al., *J. Pharmacol. Exp. Therap.,* 226:111 33–38, 1983.

Galen and Gambino, "Beyond Norrality," In: *The Predictive Value and The Efficiency of Medical Diagnosis, NY, Wiley Biomedical,* 1975.

Geib, Tuckmantel, Kozikowski, "Huperzine A-a potent acetylcholinesterase inhibitor of use in the treatment of Alzheimer's disease," *Acta Crystalogr C.,* 47:824–827, 1991.

Gelemter, "Genetic association studies in psychiatry: recent history. Chapter 2, In *Handbook of Psychiatric Genetics* (Eds. K. Blum and E. P. Noble), CRC Press, Boca Raton, pp 25–36, 1997.

Gelemter, Krazler, Satel, Rao, "Genetic association between dopemine transporter protein alleles and cocaine-induced paranoia," *Neuropsychopharmacology,* 11:195–200, 1994.

Gelemter et al., "Exclusion of close linkage of Tourette's syndrome to D1 dopamine receptor," *Am. J. Psychiatry,* 150:449–453, 1993.

Geller et al, 1970.

Geller, Hartmann, Blum, "The effects of low-dose combinations of D-amphetamine and cocaine on experimentally induced conflict in the rat," *Current Therapeutic Research,* 14:220–224, 1972.

Gessa et al., 4th World Congress on Biological Psychiatry, 459(620):10, 1985.

Gill, Daly, Heron, Hawi, Fitzgerald, "Confirmation of association between attention deficit disorder and a dopamine transporter polymorphism," *Molecular Psychiatry,* 2:311–313, 1997.

Gillis, Gigler, Pennington, DeFries, "Attention deficit disorder in reading-disabled twins: Evidence for a genetic etiology," *J. Abnorm. Child. Psychol.,* 20:343–348, 1992.

Gillman et al., *J. Neurochem.,* 37:410, 1981.

Gillman et al., "Cerebellar and frontal hypometabolism in alcoholic cerebellar degeneration studies with positron emission tomography," *Annals. Neurology,* 28:775–785, 1990.

Giovannucci, Stampfer, Krithivas, Brown, Brufsky, Hennekens, Kantoff, The CAG repeat within the androgen receptor gene and its relationship to prostate cancer, *Proc. Natl. Acad. Sci. USA,* 94:3320–3323, 1997.

Girardi, Shaywitz, Shaywitz, Marchione, Fleischman, Jones, Tamborlane, "Blunted catecholamine responses after glucose ingestion in children with attention deficit disorder," *Pediatr. Res.,* 38:539–542, 1995.

Giros et al., "Hyperlocomotion and indifference to cocaine and amphetamine in mice lacking dopamine transporter," *Nature,* 379:606612, 1996.

Glinsmann and Mertz, "Effect of trivalent chromium on glucose tolerance," *Metabolism,* 15:510–515, 1966.

Goldman-Rakic, "Topolography of cognition: Parallel distributed networks in primate association cortex," *Annu. Rev. Neurosci.,* 11:137–156, 1988.

Goldman-Rakie, In: *Plum and Mountcasle(Eds) Handbook of Physiology,* The Nervous System V. Bethesda M. D,:*Am. Physiol. Soc.,* 373–417, 1987.

Goldstein et al, "Psychiatric disorders in relatives of probands with panic disorder and/major depression," *Archives Gen. Psychiatry,* 51:383–394, 1994.

Gorski, Critical role for the medial preoptic area in the sexual differentiation of the brain, *Prog. Brain Res.,* 61:129–146, 1984.

Gottfries, Oreland, Wiberg, Winblad, "Lowered monoamine oxidase activity in brains from alcoholic suicides," *J. Neurochem.,* 25:667–673, 1975.

Gottlieb, Trifiro, Lumbroso, Pinsky, The angroden receptor gene mutation database, *Nucleic Acids Res.,* 25:158–162, 1977.

Grandy, Marchionni, Makam, Stofko, Alfano, Frothingham, Fisher, Burke-Howie, Bunzow, Server, Civelli, "Cloning of the cDNA and gene for a human $D_2$ dopamine receptor," *Proc. Natl. Acad. Sci. USA,* 86:9762–9766, 1989a Grandy, Lilt, Allen, Bunzow, Marchiormi, Makam, Reed, Magenis, Civelli, The human dopamine $D_2$ receptor gene is located on chromosome 11 at q22–q23 and identifies a TaqI RFLP, *Am. J. Hum. Genet.,* 45:778–785, 1989b.

Granon, Poucet, Thinus-Blanc, Changeux, Vidal, "Nicotinic and muscarinic receptor in the rat prefrontal cortex: Differential roles in working memory, response selection and effortful processing," *Psychopharmacology (Berlin),* 119:139–144, 1995.

Grant et. al, *Med. Sci. Sports Exerc.,* 29:992–998, 1997.

Grayson and Carlson, "The utility of a DSM-M-R based checklist in screening child psychiatric patients," *J. Am. Acad. Child. Adolec. Psychiatry,* 30:669–673, 1991.

Green and Krontiris, "Alleleic variations of reporter gene activation by the HRAS 1 minisatellite," *Genomics,* 17:429434, 1993.

Greenberg, Hodge, Vieland, Spence, "Affecteds-only linkage methods are not a panacea," *Am. J. Hum. Genet.,* 58:892–895, 1996.

Grice, Leekman, Pauls, Kurlan, Kidd, Pakstis, Chang, Buxbaum, Cohen, Gelernter, "Linkage disequilibrium of an allele at the dopamine D4 receptor locus with Tourette's syndrome by TDT," *Am. J. Hum. Genet.,* 59:644–652, 1996.

Grimsby, Chen, Wang, Lan, Shih, "Human monamine oxidase A and B genes exhibit identical exon-intron organization," *Proc. Natl. Acad. Sci. USA,* 88:3637–3641, 1991.

Grompe, "The rapid detection of unknown mutations in nucleic acids," *Nature Genet.,* 5:111–117, 1993.

Grunwald, Raveh, Doctor, et al., "Huperzine A as a pretreatment candidate drug against nerve agent toxicity," *Life Sci.,* 54:991–997, 1994.

Guan, Chen, Lu, et al, "Effects of Huperzine A on eletroencephalography power spectrum in rabbits," *Chung Kuo Yao Li Hsueh Pao,* 10:496–500 (article in Chinese), 1989.

Guipponi, Baldy-Moulinier, Malafosse, "A fokl polymorphism in the human neuronal nicotinic acetylcholine receptor a4 subunit gene," *Clin. Genetics,* 51:78–79, 1997.

Halgren and Smith, "Cognitive evoked potentials as modulatory processes in human memory formation and retrieval," *Human Neurobiology,* 6:129–139, 1987.

Halgren, Squires, Wilson, Rohrbaugh, Babb, Crandall, "Endogenous potentials generated in the human hippocampal formation and amygdala by infrequent events," *Science,* 210:803, 1980.

Halikas, Nugent, Crosby, Carlson, "1990–1991 survey of pharmacotherapies used in the treatment of cocaine abuse," *J. Addictive Diseases,* 12:129–139, 1993.

Hall et al., "Distribution of D, and $D_2$-dopamine receptors, and dopamine and its metabolites in the human brain," *Neuropsychopharmacol.,* 14:245–256, 1994a Hall, Antoniou, Wang, Cheung, Arbus, Olson, Lu, Kau, Marsden, "Structural organization of the human neuronal nitric oxide synthase gene (NOS)," *J. Biol. Chem.,* 269:33082–33090, 1994b.

Halliday, Rosenthal, Naylor, Callaway, "Averaged evoked potential predictors of clinical improvement in hyperactive children treated with methyphenidate: an initial study and replication," *Psychophysiology,* 13:429–440, 1976.

Hallmark, Reynolds, DeSouza, Dotson, Anderson, Rogers, "Effects of chromium and resistive training on muscle strength and body composition," *Med. Sci. Sports Exerc.,* 28:139–144, 1996.

Hallmark, Reynolds, Desouza et al., "Effects of chromium supplementation and resistive training on musclar strength and lean body mass in untrained men," *Med. Sci. Sports Exerc.,* 25 (Suppl. 5) S101 (abstract), 1993.

Halperin, Newcom, Koda, Pick, McKay, Knott, "Noradrenergic mechanisms in ADHD children with and without reading disabilities. A replication and extension," *J. Am. Acad. Child Adolesc. Psychiatry,* 36:1688–1696, 1997.

Halperin, Newcom, Schwartz, McKay, Bedi, Sharma, "Plasma catecholamine metabolites in ADHD boys with and without reading disabilities," *J. Clin. Child. Psychol.,* 22:219–225, 1993.

Hamada and Kakunaga, "Potential Z-DNA sequences are highly dispersed in the human genome," *Molec. Cell Biol.,* 4:26102621, 1984.

Hamada, Petrino, Kakunaga, A novel repeated element with Z-DNA-forming potential is widely found in evolutionarily diverse eukaryotic genomes, *Proc. Natl. Acad. Sci. USA,* 79:6465–6469, 1982.

Hammer, Jr. et al., *Soci., Neuroscience Abstracts,* 13(21):85 No. 2710, 1987.

Hammond-Kosack and Docherty, "A consensus repeat sequence from the human insulin gene linked polymorphic region adopts multiple quadriplex DNA structures, " *FEBS Lett.,* 301:79–82, 1992.

Hammond-Kosack, Dobrinski, Lurz, Docherty, Kilpatrick, "The human insulin gene linked polymorphic region exhibits an altered DNA structure," *Nucl. Acids Res.,* 20:231–236, 1992.

Haniford and Pulleybank, "Facile transition of poly[d(TG) .d(CA)] into a left-handed helix in physiological conditions," *Nature,* 302:632–634, 1983.

Hanin, Tang, Kindel, Kozikowski, "Natural and synthetic Huperzine. An effect on cholinergic function in vitro and in vivo," *Ann. NY Acad. Sci.,* 695:304–306, 1993.

Hanna, Omitz, Hariharan, "Urinary epinephrine excretion during intelligence testing in attention-deficit hyperactivity disorder and normal boys," *Biol. Psychiatry,* 40:553–555, 1996.

Hao, Gong, Qin, "Effects of Huperzine A on cholinesterase isoenzymes in plasma of mice and dogs," *Chung Kuo Yao Li Hsueh Pao* 9:312–316 (article in Chinese), 1988.

Hardy, Scher, Bodenreider, Sabbatini, Zhang, Namus, CaRemil, Androgen receptor CAG repeat lengths in prostate cancer: correlation with age of onset, *J. Clin. Endocrinol. Metab.,* 81:4400–4405, 1996.

Harley, "Noradrenergic and Locus modulation of the preforant path-evoked potential in rat dsentate gyrus supports a role for the locus coeruleus in attentional procession and memorial processes," *Progress in Brain Res.,* 88:307–321, 1988.

Hartruck and Lipscomb, In: *Carboxypeptidase A: in THE ENZYMES,* 1–56, Boyer, ed., Academic Press, New York, 1971

Haskell, "The influence of exercise training on plasma lipids and lipoproteins in health and disease," *Acta. Med. Scan.,* (Suppl.) 711:25–37, 1986.

Hasten et. al., *Int. J. Sports Nutr.,* 2:343–350, 1992.

Hasten, Rome, Franks, Haysted, "Effect of chromium picolinate on beginning weight training students," *Int. J. Sports Nutr.,* 2:343–350, 1992.

Hasten, Siver, Fomea, et al., "Dosage effects of chromium picolinate on body composition," *FASEB J,* 8(4):A194, 1994.

Heath, Gavin, Hinderliter, Hagberg, Bloomfield, Holloszy, "Effects of exercise and lack of exercise on glucose tolerance and insulin action," *J. Appl. Physiol.,* 55:512–517, 1983.

Hechman, "Genetic and neurobiological aspects of attention deficit hyperactivity disorder: a review," *J. Psychiatry Neurosci.,* 19:193–201, 1994.

Heils, Teufel, Petri, Seeman, Bengel, Batling, Riederer, Lesch, Functional promoter and polyadenylation site mapping of the human serotonin (5-HT) transporter gene, *J. Neural. Transm.,* 102:247–254, 1995.

Heils, Teufel, Petri, Stöber, Bengel, Lesch, Allelic variation of human serotonin transporter gene expression, J. Neurochem., 66:2621–2624, 1996.

Hérault, Perrot, Barthélérny, Büchlar, Cherpi, Leboyer, Sauvage, Lelord, Mallet, Müh, "Possible association of C-Harvey-Ras-I (HRAS-1) marker with autism," i Psychiatry Res., 46:261–267, 1993.

Herbert and Rich, "The biology of left-handed Z-DNA," *J. Biol. Chem.,* 271:11595–11598, 1996.

Herbert, "RNA editing, introns and evolution," *Trends Genet.,* 12:6–9, 1996.

Herbert, Lowenhaupt, Spitzner, Rich, "Chicken double-stranded RNA adenosine deaminase has apparent specificity for Z-DNA," *Proc. Natl. Acad. Sci. USA,* 92:7550–7554, 1995.

Hejanic and Campbell, "Differentiating psychiatrically disturbed children on the basis of a structured interview,"*J. Abnorm. Child Psychology,* 5:127–134, 1977.

Hemandez-Rodriquez and Chagoya, "Brain serotonin synthesis and $NA^+$, $K^+$-ATPase activity are increased postnatally after prenatal administration of L-tiyptophan," *Developmental Brain Research,* 25:221–226, 1989.

Hernandez, Lee, Hoebel, "Microdialysis in the nucleus accumbens during feeding or drugs of abuse: amphetamine, cocaine, and phencyclidine,". Kalivas and Nemeroff (Eds.), In: *The Mesocorticolimbic Dopamine System* (pp. 508–511), New York: New York Academy of Sciences, 1988.

Hersh, *Biochem.,* 20:2345–2350, 1981.

Hexum et al., *LifeSci,* 24:1211–1216, 1980.

Hi, Yi, Xi, "Huperzine A ameliorates the spatial working memory impairments induced by AF64A," *Neuroreport,* 6:2221–2224, 1995.

Higuchi, Muramatsu, Matsushita, Arai, Sasaki, "Presenilin-I polymorphism and Alzheimer's disease," *Lancet,* 347:1186, 1996

Hill and Neiswanger, "The value of narrow psychiatric phenotypes and super normal controls," Chapter 3. In *Handbook of Psychiatric Genetics* (Eds. K. Blum and E. P. Noble), CRC Press, Boca Raton, pp 3748, 1997.

Hillyard, Hink, Schwent, Picton, "Electrical signs of selective attention in the human brain," *Science,* 182:177–180, 1973.

Hinds, Hendricks, Craig, Chen, "Characterization of a highly polymorphic region near the first exon of the human MAOA gene containing a GT dinucleotide and a novel VNTR motif," *Genomics,* 13:896–897, 1992.

Hirschi and Hindelang, "Intelligence and delinquency: A revisionist review," *Am. Socialog. Rev.,* 42:571–587, 1977.

Hodgins and Guebaly, "More data on the Addiction Severity Index. Reliability and validity with the mentally ill substance abuser," *J Nerv. Ment Dis.,* 180:197–201, 1992.

Hoge and Biederman, "A case of Tourette's syndrome with symptorms of attention deficit disorder treated with desipirame," *J. Clin. Psychiatry*, 47:478–479, 1986.

Hosobuchi, et al., In: *Neural Peptides and Neuronal Communications*, 563, 1980.

Hotamisligil and Breakefield, "Human monoamine oxidase A gene determines levels of enzyme activity," *Am. J. Hum. Genet*, 49:383–392, 1994.

Hudson, "Drug abuse increases among U.S. teenagers beliefs about drugs' dangers soften," Psychiatric *Times*, 35–36, 1995.

Huhtaniemi, Haier, Fedio, Buchsbaum, "Neuropsychological characteristics of college males who show attention dysfunction," *Perceptual and Motor Skills*, 57:399406, 1983.

Hunt, Minderaa, Cohen, "Clonidine benefits children with attention deficit disorder and hyperactivity: Report of a double-blind placebo-crossover therapeutic trial," *J. Amer. Acad. Child Psychiat.*, 24:617–629, 1985.

Huntington's Disease Collaborative Research Group, "A novel gene containing a trinucleotide repeat that is expanded and unstable on Huntington's disease chromosomes," *Cell*, 72:971–983, 1993.

Huston et al., "Sequence-specific effects of neurokinin substance P on memory, reinforcment, and brain dopamine activity," Psychopharmacology, 103:143–149, 1991.

Imagawa, Ishikawa, Shimano, Osada, Nishihara, "CTG triplet repeat in mouse growth inhibitory factor/metallothionein Im gene promoter represses the transcriptional activity of the heterologous promoters," *J. Biol. Chem.*, 270:20898–20900, 1995.

Irenwasser, Jacocks, Rosenberger, Cox, "Nicotine indirectly inhibits [3H] dopamine uptake at concentrations that do not directly promote [3H] dopamine release in rat striatum," *J. Neurochemistry*, 56:603–610, 1991.

Irvine, Yu, Ross, Coetzee, The CAG and GGC microsatellites of the androgen receptor gene are in linkage disequilibrium in men with prostate cancer, *Cancer. Res.*, 55:1937–1940, 1995.

Iwatsubo, et al., *Biochem, Pharmacol.*, 24:1495–1503, 1975.

Jasper, "Report to the committee on methods of clinical examination in electroencephalography. Appendix: The ten-twenty system of the International Federation," *Electroencephalography and Clinical Neurophysiology*, 102:371–375, 1958.

Jeejeehboy, Chu, Marliss, Grun, Bruce-Robertson, "Chromium deficiency, glucose intolerance and neuropathy reversed by chromium supplementation in a patient receiving long-term parenteral nutrition," *Am. J. Clin. Nutr.*, 30:531–538, 1977.

Jeffreys, Royle, Wilson, Wong, "Spontaneous mutation rates to new length alleles at tandem-repetitive hypervariable loci in human DNA," *Nature*, 332:278–281, 1987.

Jensen "Linkage analysis of schizophrenia: The $D_1$ dopamine receptor gene and several flanking DNA markers," *Human Heredity*, 43:58–62, 1993.

Johnson, Jr. and Fedio, "P300 activity in patients following unilateral temporal lobectomy: a preliminary report. In: *Cerebral Psychophysiology: Studies in Event-Related Potentials*, W. C. McMcCallum, R. Zappoti, F. Denoth (Eds.), EEG Suppl. 38, Elsevier, Amsterdam, 552–557, 1986.

Johnson, Muhleman, MacMurray, Gade, Verde, Ask, Kelley, Comings, "Association between the cannabinoid receptor gene (CNR1), and the P300 wave of event-related potentials, and: drug dependence," *Mol. Psychiatry*, 2:169–171, 1997.

Jonidas et al., *Nature*, 369:623–625, 1993.

Jonsson et al., "Dopamine-related genes and their relationship to monoamine metabolites in CSF,": *Biol. Psychiatry*, 40:1032–1043, 1996.

Jurinke, van den Boom, Collazo, Jacob, Köster, "Recovery of nucleic acids from immobilized biotin-strepavidin complexes using ammonium hydroxide and application in MALDI-TOF mass spectrometry," *Anal. Chem.*, 69:904–910, 1997.

Kaats et al., 1990.

Kaats, Fisher, Blum, "The effects of chromium picolinate supplementation on body composition in different age groups," Abstract, American Aging Association 21st annual meeting, Denver, Colo., October, 1991.

Kaats et al., "The short-term therapy efficacy of treating obesity with a plan of improved nutrition and moderate caloric restriction" *Curr. Ther. Res.* 51:261–274, 1992.

Kaats, Blum, Fisher, Adelman, "Effects of chromium picolinate supplementation on body composition:
a randomized dobule-masked placebo-controlled study," *Current Therap. Res.*, 10:747–756, 1996.

Kannel and McGee, "Diabetes and cardiovascular risk factors," *The Framingham Study. Circulation*, 59:8–13, 1979.

Kauck, Poustka, Benner, Speiler, Lesch, Poustka, Association of the serotonin transporter (5-HTT) promoter long variant with autism, *Am. J. Hum. Genet.*, 61:A280, 1997.

Kaye, Ebert, Gwirtsman, et al., "Differences in brain serotonergic metabolism between non-bulimic and bulimic patients with anorexia nervosa," *Am. J. Psychiatry*, 141:1598–1601, 1984.

Kennedy, German, Rutter, "The minisatellite in the diabetes susceptibility locus IDDM2 regulates insulin transcription," *Nature Genet.*, 9:293–298, 1995.

Khan and Dekirmenjian, "Urinary excretion of catecholamine metabolites in hyperkenetic child syndrome," *Am. J. Psychiatry*, 138:108–112, 1981.

Kimberg et al., 1997.

Kitchalong, Fernandez, Bunting et al., "Chromium picolinate supplementation in lamb rations. Effects on performance, nitrogen balance, endocrine and metabolic parameters," *J. Animal Sci.*, 71 (Suppl 1)291, 1993.

Klinteberg and Magnusson, "Aggressiveness and hyperactive behavior as related to adrenaline excretion. Special Issue: Personality and aggression," *Eur. J. Personality*, 3:81–93, 1989.

Knell and Comings, Tourette syndrome and attention deficit hyperactivity disorder: Evidence for a genetic relationship, *J. Clin. Psychiat.*, 54:331–337, 1993.

Kochersperger, Parker, Sicillano, Darlington, Denney, "Assignment of genes for human monamine oxidase A and B to the X chromosome," *J. Neurosci. Res.*, 18:601–619, 1986.

Kokkevi and Stefanis, "Drug abuse and psychiatric comorbidity," *Com. Psychiatr.*, 36:329–337, 1995.

Koob and Bloom, "Cellular and molecular mechanisms of drug dependence," *Science*, 242:715–723, 1988.

Kozikowski, Miller, Yamada, et al., "Delineating the pharmacophoric elements of Huperzine A: importance of the unsaturated three-carbon bridge to its ACHE inhibitory activity, " *J. Med. Chem.*, 34:3399–3402, 1991.

Kreuz and Rose, Assessment of aggressive behavior and plasma testosterone in a young criminal population, *Psychosomatic Medicine*, 34:321–332, 1972.

Krontiris, Devlin, Karp, Robert, Risch, "An association between the risk of cancer and mutations in the Hras 1 minisatellite locus," *New Eng. J. Med.*, 329:517–523, 1993.

Krontiris, DiMartino, Colb, Parkinson, "Unique allelic restriction fragments of the human Ha-ras locus in leukocyte and tumor DNAs of cancer patients," Nature, 313:369–374, 1985.

Kuperman et al., "Enzyme activity and behavior in hyperactive children grown up," Biol. Psychiatry, 24:375–383, 1988.

La Spada, Wilson, Lubahn, Harding, Fischbeck, Clark, Kelly, Smith, Fairweather, Brown, Johnston, Haites, Androgen receptor gene mutations in X-linked spinal and bulbar muscular atrophy prenatal diagnosis for dystrophia myotonica using the polymerase chain reaction, Nature, 11:467–470, 1991.

Laganiere, Corey, Tang, Wulfert, Hanin, "Acute and chronic studies with the anticholinesterase Huperzine A: effect on central nervous system cholinergic parameters," Neuropharmacology, 30(7):763–768, 1991.

Lahey, Schaughency, Frame, Strauss, "Teacher ratings of attention problems in children experimentally classified as exhibiting attention deficit disorder with and without hyperactivity," J. Am. Acad. Child Psychiatry, 24(5):613616, 1985.

Lahey, Schaughency, Strauss, Frame, "Are Attention Deficit Disorders With And Without Hyperactivity Similar Or Dissimilar Disorders?" J. Am. Acad. Child Psychiatry, 23:302–309, 1984.

Lahoste, Swanson, Wigal, Glabe, Wigal, King, Kennedy, "Dopamine D4 receptor gene polymorphism is associated with attention deficit hyperactivity disorder," Mol. Psychiatry, 1:121–124, 1996.

Lallement, Veyret, Masqueliez, et al, "Efficacy of hyperine in preventing soman-induced seizures, neuropathological changes and lethality," Fundam. Clin. Pharmacol., 11:387–397, 1997.

Lan, Heinzmann, Gal, Klisak, Orth, Lai, Grimsley, Sparkes, Mohandas, Shih, "Human monamine oxidase A and B genes map to Xp11.23 and are deleted in a patient with Norrie disease," Genomics, 4:552–559, 1989

Lapin, Maker, Sershen, Lajtha, "Action of nicotine on accumbens dopamine and attenutation with repeated administration," Eur. J. Pharmacology, 160:53–59, 1989.

Lario, Calls, Cases, Orila, Torras, Rivera, "Msp I identifies a biallelic polymorphism in the promoter region of the alpha 2A-adrenergic receptor gene," Clin. Genetics, 51:129–130, 1997.

Lawford, Young, Rowell, Qualichefski, et al, "Bromocriptine in the treatment of alcoholics with D2 dopamine receptor A1 allele," Nature Med., 1:337–341, 1995.

Lazarova et. al., Methods & Findings in Experimental & Clinical Pharmacology, 8(9):547–552, 1986.

LeDoux, "Emotional memory systems in the brain," Behavior Brain Research, 20:69–79, 1993.

Lee and Reasner, "Beneficial effect of chromium supplementation on serum triglyceride levels in NIDDM," Diabetes Care, 17:1449–1452, 1994.

Leibowitz and Hor, "Endorphinergic and noradrenergic systems in the paraventricular nucleus: Effects on eating behavior," Peptides, 3:421428, 1982.

Leibowitz, "Brain neurotransmitters and appetite regulation," Psychopharmacological Bull., 21:412–418, 1985.

Leiner et al., "Reappraising the cerebellum: what does the hindbrain contribute to the forebrain?" Behav. Neurosci., 103:998–1008, 1989.

LeMoal and Simon, "Mesocorticolimbic dopaminergic network: functional and regulatory roles," Physiol. Rev., 71:155–234, 1991.

Lemoal et al, "Radiofrequency lesions of the ventral mesencephalic tegmentum: Neurological and behavioral considerations," Exp. Neurol., 50:521–535, 1976.

Leppert, Anderson, Quattlebaum, Stauffer, O'Connell, Nakamura, Laouel, White, "Benign familial neonatal convulsions linked to genetic markers on chromosome 20," Nature, 337:647–648, 1989.

Lesch, Bengel, Heils, Sabol, Greenberg, Petri, Benjamin, Muller, Hamer, Murphy, Association of anxiety-related traits with a polymorphism in the serotonin transporter gene regulatory region, Science, 274:1527–1531, 1996.

Levin et al., "Cholinergic-dopaminergic interactions in cognitive performance," Behavioal Neural. Biology, 54:271–299, 1990.

Levin and Rose, "Acute and chronic nicotinic interactions with dopamine systems and working memory performance,"Annals. NYAcad. Sci., 757:245–252, 1995.

Levin, Conners, Sparrow, Hinton, Erhardt, Meck, Rose, Marck, "Nicotine effects on adults: with attention-deficit/hyperactivity disorder," Psychopharmacology (Berlin), 123:55–63, 1996.

Levine, Streeten, Doisy, "Effects of oral chromium supplementation on the glucose tolerance of elderly human subjects," Metabolism, 17:114–125, 1968.

Levine and Manley, "Transcriptional repression of eukaryotic promoters," Cell, 59:405408, 1989.

Li and Chung, "Isolation and Structure of an Untriakontapeptide with Opiate Activity from Camel Pituitary Glands," Proc. Nat. Acad. Sci. USA; 73:1145–1148, 1976.

Li, Li, Sharp, Nucifora, Schilling, Lanahen, Worley, Snyder, Ross, "A huntingtin-associated protein enriched in brain with implications for pathology of Huntington's disease," Nature, 378:398, 1995.

Li, Tang, Little, Köster, Hunter, McIver Jr., "High-resolution MALDI fourier transform mass spectrometry of oligonucleotides," Anal. Chem., 68:2090–2096, 1996.

Liam, Chen, Chen, Wu, "The effects of various levels of chromium picolinate on growth and serum traits 1 of pigs," J. Chin Soc. Anim. Aci., 22(4):349–357, 1993.

Lichter, Barr, Kennedy, Van Tol, Kidd, Livak, "A hypervariable segment in the human dopemine receptor (DRD4) gene," Hum. Mol. Genet, 2:767–773, 1993.

Lieberman et al., J Psych. Res., 17:135, 1983.

Lin, Powell, Murray, Gill, "Monoamine oxidase A gene and bipolar affective disorder," Am. J. Hum. Genet., 54:1122–1124, 1994.

Lindberg, Asberg, Sundqvist-Stensman, 5-hydroxyindole acetic acid levels in attempted suicides who have killed their children, Lancet., 2:928, 1984.

Lindemann, Wood, Harper, Kornegay, "Chromium picolinate additions to diets of growing-finishing pigs," J Animal Sci., 71 (Suppl 1):167, 1993.

Little, Cornish, O'Donnell, Braun, Cotter, Köster, "MALDI on a chip: Analysis of arrays of low-femtomole to subfemtomole quantities of synthetic oligonucletides and DNA diagnostic products dispensed by a piezoelectric pipet," Anal. Biochem., 69:4540–4546, 1997.

Liu and Liu, "Intelligence promoting Chinese materia medica," Chung Kuo Chung Hsi I Chieh Ho Tsa Chih, 15:59–61 (article in Chinese), 1995a.

Liu, Sobell, Heston, Sommer, "Screening the dopamine D, receptor gene in 131 schizophrenics and eight alcoholics: identification of polymorphisms but lack of functionally significant sequence changes," Am. J. Med. Gen. (Neuropsych. Genet.), 60:165–171, 1995b.

Lou, "Dopamine precursors and brain function in phenylalanine hydroxylase deficiency," Acta. Paediatrica., (Suppl) 407:86–88, 1994.

Lovinger and Grant, "Alcohol neurotoxicity: effects and mechanisms," Handbook of Neurotoxicology, Marcel Dekker, Publishers, New York, 1995.

Lu, Shou, Tang, "Improving effect of Huperzine A on discrimination performance in aged rats and adult rats with experimental cognitive impairment," Chung Kuo Yao Li Hsueh Pao, 9:11–15 (article in Chinese), 1988.

Lyoo et al, "The corpus callosum and lateral ventricles in children with Attention-Deficit Hyperactivity Disorder. A brain magnetic resonance imaging study," Biol. Psychiatry, 40:1060–1063, 1996.

Mackintosh, "A theory of attention: Variations in the associability of stimuli with reinforcement," Psychology Review, 82:276–298, 1975.

MacLusky and Naftolin, Sexual differentiation of the central nervous system, Science, 211:1294–1303, 1981.

MacMurray, Saucier, Muhleman, Gade, Chiu, Wu, Blake, Ferry, Johnson, Comings, "Polygenic prediction of parity: $GABA_A$-b3 and dopamine $DRD_4$ gene markers," Psychiat. Genet., 6:161, 1996.

Mahaer and Wurtman, "L-threonine administration increases glycine concentrations in the rat central nervous system," Life Science, 26(26):1283–1286, 1980.

Maison et al., "$^{123}$b-Cit Spect imaging of straital dopamine transporter binding Tourette's disorder," Am. J. Psychiatry, 152:1359–1361, 1995.

Malafosse, Leboyer, Dulac, Navalet, Plouin, Beck, Laklou, Mouchnino, Grandscene, Vallee, Guilloud-Bataille, Samolyk, Baldy-Moulinier, Feingold Mallet, "Confirmation of linkage of benign familial neonatal convulsion to D20S19 and D20S20," Hum. Genet., 89:5458, 1992.

Malhotra et al., "The association between the dopamine $D_4$ 16 amino acid repeat polymorphisms and novelty seeking," Mol. Psychiatry, 1:388–389, 1996.

Mann and Stanley, "Postmortem monoamine oxidase enzyme kinetics in the frontal cortex of suicide victims and controls" Acta Psychiatr. Scand, 69:135–139, 1984.

Marina et al, "Izvestia Sib," Dep.of the Academy of Science of the USSR, Ser. Biol. Sciences, 3:85–89, 1973.

Mattsson, Schalling, Olweus, Löw, Svensson, Plasma testosterone, aggessive behavior, and personality dimensions in young male delinquents, J. Am. Acad. Child. Adolesc. Psychiatry, 19:476–480, 1980.

Maurer et al., "Topographic mapping of EEG and auditory evoked P3000 in neuropsychopharmacology (topographic pharmacor-EEG and pharmaco-AEp 300)," Pharmacopsychiatry, 21:338–342, 1988.

McCarty, "Homologous physiological effects of phenformin and chromium picolinate," Med. Hypoth., 41:316–324, 1993.

McConville, Sanberg, Fogelson et. al, "The effect of nicotine plus haloperidol compared to nicotine only and placebo only in reducing tic severity and frequency in Tourette's disorder," Biol. Psychiatry, 31:832–840, 1992.

McGee, Williams, Moffitt, Anderson, "A comparison of 13-year-old boys with attention deficit and/or reading disorder on neuropsychological measures," J. Abnorm. Child Psychol., 17:37–53, 1989.

McKinney, Miller, Yamada, et al., "Potencies and stereoselectivities of enantiomers of Huperzine!A for inhibtion of rat cortical acetylcholinesterase," Eur. J. Pharmacol., 203:303–305, 1991.

Mechelini, Urbanek, Dean, Goldman, "Polymorphism and genetic mapping of the human oxytocin receptor gene on chromosome 3," Am. J. Med. Genet, 60: 183–187, 1995.

Mefford, and Potter, "A neuroanatomical and biochemical basis for attention deficit disorder with hyperactivity in children: A defect in tonic adrenaline mediated inhibition of locus coeruleus stimulation," Med. Hypotheses., 29:33–42, 1989.

Meltzer and Arora, "Platelet markers of suicidality," Ann. N.Y. Acad. Sci., 487:271–280, 1986.

Mertz, Nutr., 123:626–633, 1992.

Migeon, Brown, Axelman, Migeon, Studies of the locus for androgen receptor: localization on the human X and evidence for momology with the Tfm locus in the mouse, Proc. Natl. Acad. Sci. USA, 78:6339–6343, 1981.

Mikines, Sonne, Farrell, Tronier, Gablo, "Effect of training on the dose-response relationship for insulin action in men," J. Appl. Physiol., 66:695–703, 1989.

Miller et al., "Overload: ADHD and the Additive Brain," Andrew McMeal, Kansas City, Mo., 1996.

Miller, "Neuropsychological perspectives on delinquency," Behav. Sci. Law, 6:409–428, 1988.

Misra, et al., "Stereospecific potentiation of opiate analgesia by cocaine: Predominant role of noradrenaline," Pain., 28:129–138, 1987.

Moffit and Silva, "IQ and delinquency: A direct test of the differential detection hypothesis," J. Abnormal Psychology, 97:330–333, 1988.

Moffitt, "Juvenile delinquency and attention deficit disorder: Boys' developmental trajectories from age 3 to age 15," Child Dev., 61:893–910, 1990.

Moffitt, Adolescence-limited and life-course-persistent antisocial behavior: A developmental taxonomy," Psychological Rev., 10:674–701, 1993a Moffitt, "The neuropsychology of conduct disorder," Dev. Psychopathology, 5:135–151, 1993b.

Moir and Eccleston, "The effects of precursos Ioding in the cerebral metabolism of 5-hydroxyindoles," J. Neurochem., 15:1093–1108, 1968.

Mooney and Cromwell "Effect of chromium picolinate on performance, carcass composition and tissue accretion in growing-finishing pigs," J. Animal Sci., 71(Suppl 1):167, 1993.

Morrison et al., "A family study of the hyperactive child syndrome," Bio. Psychiatry, 3:189–195, 1971.

Morrow et al., "Delay in P300 latency in patients with organic solvent exposure," Arch. Neurol., 49:315–320, 1992.

Mullis, Faloona, Scharf, Saiki, Horn, Erlich, "Specific enzymatic amplification of DNA in vitro: the polymerase chain reaction," Cold Spring Harbor Syrup Quant. Biol., 51:263–272, 1986.

Nadel, Weisman-Shomer, Fry, "The fragile X syndrome single strand $d(CGG)_n$ nucleotide repeats readily fold back to form unimolecular hairpin structures," J. Biol. Chem., 270:28970–28977, 1995.

Nauta, Limbic innervation of the striatum. In Friedhoff and Chase (Eds.), Gilles de la Tourette Syndrome (pp. 4147). New York: Raven Press, 1982.

Naylor and Clark, "d(TG)n.d(CA)n sequences upstream of the rat prolactin gene form Z-DNA and inhibit gene transcription," Nucl. Acids Res., 18:1595–1601, 1990.

Neiswagner, Hill, Kaplan, "Association between alcoholism and the TaqI A RFLP of the dopamine $D_2$ receptor gene in the absence of linkage," Psychiatr. Genet., 3:130 (abstract), 1995.

Neiswanger et al, "Association between alcoholism and the TaqI A RFLP of the dopamine $D_2$ receptor gene in absence of linkage" Am. J. Med. Genet. (Neuropsychiatr. Genet.), 60:267–271, 1995.

Nelson, Demas, Huang, Fishman, Dawson, Dawson, Snyder, "Behavioral abnormalities in male mice lacking neuronal nitric oxide synthase," Nature, 378:383–386, 1995.

Neshinge et al, "Event-related brain potentials as indicators of visual recognition and detection of criminals by their use," *Forensic Sci. Int.*, 51:95–103, 1991.

Newcorn, Halperin, Healey, O'Brien, Pascualvaca, Wolf, Morganstein, Sharma, Young, "Are ADDH and AD-HD the Same or Different?," *J. Am. Acad. Child Adoles. Psychiatry*, 28(5):734–738, 1989.

Noble, Blum, Ritchie, Montogomery, Sheridan, "Allelic association of the $D_2$ dopamine receptor gene with receptor-binding characteristics in alcoholism," *Arch. Gen. Psychiatry*, 48:648–654, 1991.

Noble, Blum, Khalsa, Ritchie, Montgomery, Wood, Fitch, Ozkaragoz, Sheridan, Anglin, Parades, Treiman, Sparkes, "Allelic association of the $D_2$ dopamine receptor gene with cocaine dependence," *Drug Alc. Dep.*, 33:271–285, 1993.

Noble et al, "Prolonged P300 latency in children with the $D_2$ dopamine receptor A, allele," *Am. J. Hum. Genet.*, 54:658–668, 1994.

Nobel et al., "$D_2$dopamine receptor polymorphism and brain regional glucose metabolism," *Am. J. Med. Gen.*, 74:1–5, 1997.

Nobel, "The $DRD_2$ Gene, Smoking, and Lung Cancer," *J. Natl. Cancer Inst.*, 90:343–363, 19 98.

Noldy et al., "Quantitative EEG and P300 in Cocaine withdrawal," *Brain Topography*, 3:262–263, 1990.

Nordheim, Tesser, Azorin, Kwon, Möler, Rich, "Isolation of Drosophilia proteins that bind selectively to left-handed Z-DNA," *Proc. Natl. Acad. Sci. USA*, 79:7729–7733, 1982.

Nordheim and Rich, "Negatively supercoiled simian virus 40 DNA containing Z-DNA segments within tanscriptional enhancer sequences," *Nature*, 303:674–679, 1983.

Nordheim and Rich, "The sequence (dC-dA)n.(dG-dT)n forms left-handed Z-DNA in negatively supercoiled plasmids," *Proc. Natl. Acad. Sci. USA*, 80:1821–1825, 1983.

Nöthen, Eggerman, Albus, Borrmann, Rietschel, Körner, Maier, Minges, Lichtermann, Franzek, Weigelt, Knapp, Propping, "Association analysis of the monamine oxidase A gene in bipolar affective disorder by using family-based internal controls," *Am. J. Hum. Genet.*, 57:975–977, 1995.

Nunes et al., "Treating anxiety in patients with alcoholism" *J. Clin. Psychiatry*, 56(Supp 2):3–9, 1995.

O'Donnell, Tang, Köster, Smith, Cantor, High-density, covalent attachment of DNA to silicon wafers for analysis by MALDI-TOF mass spectrometry," *Anal. Chem.*, 69:2438–2443, 1997.

Oades, "Attention deficit disorder with hyperactivity (ADHD): The contribution of catecholaminergic activity," *Prog. Neurobiol.*, 29:365–391, 1987.

Offenbacher and Pi-Sunyer, "Chromium in human nutrition," *Ann. Rev. Nutr.*, 8:543–563, 1988.

Ogawa, Lubahn, Korach, Pfaff, Aggressive behaviors of transgenic estrogen-receptor knockout male mice, *Ann. NY Acad. Sci.*, 794:384–385, 1996.

Ogilvie, Battersby, Bubb, Fink, Hamaar, Goodwin, Smith, "Polymorphism in serotonin transporter gene associated with susceptibility to major depression," *Lancet*, 347:731–733, 1996.

Ohshima, Kang, Larson, Wells, "Cloning, characterization and properties of seven triplet repeat DNA sequences," *J. Biol. Chem.*, 271:16773–16783, 1996.

Olds, "Pleasure centers in the brain," *Scientific American*, 195:5–116, 1956.

Oltmans, "Norepinephrine and dopamine levels in hypothalmic nuclei of the genetically obese mouse (ob/ob)," *Brain Res.*, 273:369–373, 1983.

Olweus, Stability of aggressive reaction panems in males: A review, *Psychological Bull.*, 86:852–875, 1988.

Olweus, Mattsson, Schalling, Low, Circulating testosteone levels and aggression in adolescent males: A casual analysis, *Psychosomatic Medicine*, 50:261–272, 1988.

Ostareck-Lederer, Ostareck, Standart, Thiele, "Translation of 15-lipoxygenase mRNA is inhibited by a protein that binds to a repeated sequence in the 3' untranslated region," *EMBO J.*, 13:1476–1481, 1994.

Ostrovsky, Substance Alc., Actions/Misuse, 5:247–253, 1984.

Owen and McGuffin, "Association and linkage: complementary strategies for complex disorders," *J. Med. Genet.*, 30:638–639, 1993.

Ozelius, Hus, Bruns, Powell, Chen, Weyler, Utterback, et al., "Human monamine oxidase gene (MAOA): chromosome position (Xp21-p11) and DNA polymorphism," *Genomics*, 3:53–58, 1988.

Page, Ward, Southern, "Effect of chromium picolinate on growth and carcass characteristics of growing-finishing pigs," *J. Am. Sci.*, 69(Suppl 1):403, 1991.

Page, Southern, Ward, et al., "Effect of chromium on growth serum and carcass traits, and organ weights of growing-finishing pigs from different ancestral sources," *J. Animal Sci.*, 70(Suppl 1):235, 1992.

Page, Southern, Ward, Thompson, "Effect of chromium picolinate on growth and serum carcass traits of growing finishing pigs," *J. Animal Sci.*, 71:656662, 1993.

Pandey, Dorus, Shaughnessy, Gaviria, Val, Davis, "Reduced platelet MAO activity and vulnerability to psychiatric disorders," *Psychiatry Res.*, 2:315–321, 1980.

Pandey, Sharma, Janicak, Davis, "Monamine oxidase and cortisol response in depression and schizophrenia," *Psychiatry Res.*, 44:1–8, 1992.

Pang and Kozikowski, "Prediction of the binding site of 1-benzyl[(5,& imethoxy-1-indanon-2-yl) methyl] piperidine in acetylcholinesterase by docking studies with the SYSDOC program," *J. Comput. Aided Mol. Des.*, 8:683–693, 1994a.

Pang and Kozikowski, "Prediction of the binding sites of huperzine A in acetylcholinesterase by docking studies," *J. Comput. Aided Mol. Des.*, 8:669681, 1994b.

Pardo, Fox, Raichle, "Localization of a human system for sustained attention by positron emission tomography," *Nature*, 349:6144, 1991.

Pauls et al., "Demonstration of vertical transmission of attention deficit disorder" *Ann. Neurol.*, 14:363, 1983.

Peck and Wang, "Transcriptional block caused by negative super-coiling induced structural change in an alternating CG sequence," *Cell*, 40:129–137, 1985.

Pennington, Groisser, Welsh, "Contrasting cognitive deficits in attention deficit hyperactivity disorder versus reading disability," *Dev. Psychol.*, 29:511–523, 1993.

Persico et al., "Polymorplisms of the $D_2$ dopamine receptor gene with receptor-binding characteristics in alcoholism," *Arch. Gen. Psych.*, 48:648–654, 1991.

Persico and Uhl, "Polymorphisms of the $D_2$ dopamine receptor gene in polysubstance abusers," Chapter 20, (Eds. Blum and Noble), CRC Press, Boca Raton, 353–366, 1997.

Peterson, Leekman, Scalaill, Naftolin, Keefe, Charest, Cohen, Steroid hormones and CNS sexual dimorphisms modulate symptom expression in Tourtte's syndrome, *Psychoneuroendocrinology*, 17:553–563, 1992.

Petkov and associates, *Acta Physiologica et Pharmacolgica Bulgarcia*, 12(1):3–16, 1986.

Phillips and Mulley, "SSCP variants within the a4 subunit of the neuronal nicotinic acetylcholine receptor gene," *Clin. Genetics*, 51:135–136, 1997.

Picton and Stuss, "The component structure of the human event-related potentials. In *Motivation, Motor and Sensory Processes of the Brain: Electrical Potentials, Behavior and Clinical Use*, H. H. Kornhuber and L. Keecke (Eds.), Progress in Research, New York: Elsevier, 54:17–49, 1980.

Pieretti, Zhang, Fu, Warren, Oostra, Caskey, Nelson, "Absence of expression of the FMR-1 gene in fragile X syndrome," *Cell,* 66:817–822, 1991.

Pliszka, Maas, Rogeness, Baker, "Urinary catecholamines in attention-deficit hyperactivity disorder with and without comorbid anxiety," *J. Am. Acad. Child. Adolesc. Psychiatry.,* 33:1165–1173, 1994.

Pliszka, Mccracken, Maas, "Catecholamines in attention-deficit hyperactivity disorder Current perspectives," *J. Am. Acad. Child. Adolesc. Psychiatry,* 35:264272, 1996.

Plomin, McClearn, Smith, Vignetti, Chorney, Chorney, Venditti, Kasarda, Thompson, Detterman, et. al, "DNA markers associated with high versus low IQ: The IQ Quantitative Trait Loci (QTL) project," *Behav. Genet.,* 24:107–118, 1994.

Pohjalainen etal., "Genetic determinant of human D, dopamine receptor binding characteristics in vivo," *Am. J. Human Gen.,* 59:2255, 1996.

Pollock and Schmidt, (eds.), In: *Heart Disease and Rehabilitation,* 3rd Ed., New York, N.Y., John Wiley and Sons, Inc., 1995.

Poloni el al., *Experientia,* 30:640, 1974.

Polozhy et al., "Biology of Siberian Plants Requiring Protection," *Novisibirisk,* 85–114.; 1985.

Polymeropoulos, Xiao, Rath, Merril, Tetranucleotide repeat polymorphism at the human aromatase cytochrome P450 gene (CYP19), *Nucleic Acids Res.,* 19:195, 1991.

Pontieri, Tanda, Orzi, DiChiara, "Effects of nicotine on the nucleus accumbens and similarity to those of addictive drugs," *Nature,* 382:255–257, 1996.

Pontius, "Dysfunction patterns analogous to frontal lobe system and caudate nucleus syndrome in some groups of minimal brain dysfunction," *J. Am. Med. Women's Assn.,* 26:285–292, 1973.

Porjesz et al., "N2 component of the event-related brain potential in abstinent alcoholics," *Electroencephalogr. Clin. Neurophysiol.,* 66:121–131, 1987.

Posner and Peterson, "The attention system of the human brain," *Annu. Rev. Neurosci.,* 13:25–42, 1990.

Posner, Cohen, and Rafal, "Neural systems control of spatial orienting," *Philosophical Transactions of the Royal Society of London,* 298:187–198; 1982.

Posner, Early, Reiman, Pardo, Dhawan, "Asymmetries in hemispheric control of attention in schizophrenia," *Archives of General Psychiatry,* 45, 814–821, 1988.

Press, Geller, Evans, "The effect of chromium picolinate on serum cholesterol and apolipoprotein fractions in human subjects," *West J. Med.,* 152:41–45, 1990.

Pricheps, Sutton, Hakerem, "Evoked potentials in hyperkinetic and normal children under certainty and uncertainty: a placebo and methylphenidate study," *Psychophysiology,* 13:419–428, 1976.

Propping, Rey, Friedl, Beckmann, "Platelet monamine oxidase in healthy subjects: the 'biochemical high-risk paradigm' revisited," *Arch. Psychiatr. Nervenkr.,* 230:209–219, 1981.

Pugliese, Zeller, Fewrnandez, Zalcberg, Bartlett, Ricordi, Pietropaolo, Eisenbarth, Bennett, Patel: "The insulin gene is transcribed in the human thymus and transcription levels correlate with allelic variation at the INY VNTR-IDDM2 susceptibility locus for type 1 diabetes," *Nature Genet.,* 15:293–297, 1997.

Qian, Wang, Zhou, Chen, Zhou, Chen, "Pharmacokinetics of tablet huperzine A in six volunteers," *Chung Kuo Yao Li Hsueh Pao,* 16(5):396–398 (in chinese), 1995.

Rapoport, Donnelly, Zametkin, Carrougher, "Situational Hyperactivity in a U.S. Clinical Setting," *J Child Psychol. Psychiatry,* 27(5):639–646, 1986.

Rapoport, Mickkelsen, Ebert, Brown, Weise, Kopin, "Urinary catecholamine and amphetamine excretion in hyperactive and normal boys, *J. Nerv. Ment. Dis.,* 66:731–735, 1978.

Raves Harel, Pang, Silman, Kozikowski, Sussman, "Structure of acetylcholinesterase complexed with the nootropic alkaloid, (−)-huperzine A," *Nat. Struct. Biol.,* 4(1):5763, 1997.

Regiawi, *Subs. Alc.,* Actions/Misuse 1:151–158, 1980.

Reith etal., "Sodium-Independent Binding of $^{3}H$ Cocaine in Mouse Striatum is Serotonin Related," Brain Research, 342(1):145–148, 1985.

Riales, "Chromium in Nutrition and Metabolism," New York, N.Y., Elsevier/North-Holland Biomedical Press, 1979.

Rich, Nordheim, Wang, The chemistry and biology of left-handed Z-DNA, *Annu. Rev. Biochem.,* 53:791–856, 1984.

Richards, Samuels, Turnure, Ysseldyke, "Sustained and selective attention in children with learning disabilities," *J. Learn. Disabil.,* 23:129–136, 1990.

Riess, Weber, Hayden, "(CA)n-dinucleotide repeat polymorphism at the locus for the alpha2C adrenergic receptor (ADRA2C) on 4q16," *Hum. Molec. Genet.,* 1:452, 1992.

Ringholz, "Inconsistent attention in chronic survivors of severe closed head injury," *Doctoral Dissertation,* University of Houston, 1989.

Risch and Botstein, "A manic depressive history," *Nature Genet.,* 12:351–353, 1996a.

Risch and Merikangas, "The future of genetic studies of complex human diseases," *Science,* 273:11516–1517, 1996b.

Risch and Zhang, "Mapping quantitative trait loci with extreme discordant sib pairs: Sample size considerations," *Am. J. Hum. Genet.,* 58:836–843, 1996.

Riviere and Bueno, "Origin of the stimulation of food intake by oral administration of enkephalinase inhibitors in sheep," *Life Sci.,* 41:333–339, 1987.

Robins, Deviant Children Grown Up, Baltimore: Williams and Wilkins, 1966.

Robins, Helzer, Croughan, Ratclif, "National Institute of Health diagnostic interview schedule," *Arch. Gen. Psychiatry.,* 38:381–389, 1981.

Roeback, Hla, Chambless, Fletcher, "Effects of chrormium supplementation on serum high-density lipoprotein cholesterol levels in men taking beta blockers," *Ann. Int. Med.,* 115:917–924, 1991.

Rogan, Stäubli, LeDoux, Fear conditioning induces associated long-term potentiation in the amygdala, *Nature,* 390:604–607, 1997.

Rogeness et. al., "Biochemical differences in children with conduct disorder socialized and undersocialized" *Am. J. Psychiatry,* 139:307–311, 1982.

Rogeness, Hernandez, Macedo, Mitchell, Amrung, Harris, "Clinical characteristics of emotionally disturbed boys with very low activities of dopamine b-hydroxylase," *J. Am. Acad. Child. Adolesc. Psychiatry.,* 23:203–208, 1984.

Rogeness et al., "Plasma dopamine-beta-hydroxylase and preschool behavior in children with conduct disorder" *Child Psychiatry Human Devel.,* 20:149–156, 1989a.

Rogeness, Maas, Javors, Macedo, Fischer, Harris, "Attention deficit disorder symptoms and urine catecholamines," *Psychiatry Res.,* 27:241–251, 1989b.

Roleda, Kaneko, Ehlers, "The effects of acute cocaine administration on auditory event-related potentials in rats," *Neuroscience Letters,* 160:4–8, 1993.

Rosvold, Mirsky, Sarason, Bransome, Beck, "A continuous performance test of brain damage," *Journal of Consulting Psychology,* 20:343–352, 1956.

Rourke, Bakker, Fisk, Strang, "Child neuropsychology: an introduction to theory, research, and clinical practice," NY, The Guilford Press, 389 pages, 1983.

Rourke, "Neuropsychology of Learning Disabilities: Essentials of Subtype Analysis," NY, The Guilford Press, 351 pages, 1985.

Rourke, Fisk, Strang, "Neuropsychological assessment of children: a treatment-oriented approach," NY, The Guilford Press, 286 pages, 1986.

Rourke, "Nonverbal Learning Disabilities: The Syndrome and the Model," NY, The Guilford Press, 253 pages, 1989.

Russchen, Bakst, Amaral, Price, The amydgalostriatial projections in the monkey. An anterograde tracing study, *Brain Res.,* 329:241–257, 1985.

Salzmann, Vidyasagar, Creutzfeldt, "Functional comparison of neuronal properties in the primate posterior hippocampus and parahippocampus (area TF/TH) during different behavioural paradigms involving memory and selective attention," *Behavior Brain Research,* 26:133–149, 1993.

Sanberg, Fogelson, Manderscheid, Parker, Norman, McConville, "Nicotine gum and haloperidol in Tourette's syndrome [letter]," *Lancet.,* 1:5921, 1988.

Sanberg, Silver, Shylle, Philipp, Cahill, Fogelson, McConville, "Nicotine for the treatment of Tourette's syndrome," *Pharmac. Ther.,* 74:21–25, 1997.

Sara et al., "Locus coerulues-evoked responses in behaving rats: a clue to the role of noradrenaline in memory" *Brain Research Bulletin,* 35(5–6):457–465, 1994.

Saratikav et. al., *Pharmazine Bd.,* 23:S203–305, 1968.

Saratikov, *Chem. Pharm. Mag.,* 4:56–59, 1977.

Saratikov and Krasnov, "Rhodiola rosea is a valuable medicinal plant," *Tomsk,* p. 252, 1987.

Saratikov, "Golden Root (Rhodiola rosea)," *Tomsk,* p. 155, 1974.

Saratikov et. al., "Izvestia Sib. Dep. Of the Academy of Science of the USSR," *Ser. Biolmed. Sciences,* 5(1):108–115, 1968.

Sarkar, Kapelner, Grandy, Marchionni, Civelli, Sobell, Heston, Sommer, "Direct sequencing of the dopemine D2 receptor (DRD2) in schizophrenics reveals three polymorphisms but no structural change in the receptor," *Genomics.,* 11:8–14, 1991.

Satterfield, and Schell, A prospective study of hyperactive boys with conduct problems and normal boys: Adolescent and adult criminality, *J. Am. Acad. Child Adolesc. Psychiatry,* 36:1726–1735, 1997.

Saxena, Qian, Kovach, Kozikowski, Pang, Vellom, Radic, Quinn, Taylor, Doctor, "Identification of amino acid residues involved in the binding of Huperzine A to cholinesterases," *Protein Sci.,* 3(10):17701778, 1994.

Scatton, Rauquier, Javoid-Agid, Agid, "Dopamine deficiency in the cerebral cortex in Parkinson's disease," *Neurology,* 32:1039–1040, 1982.

Schaal, Tremblay, Soussignan, Susman, Male testosterone linked to high social dominance but low physical aggression inearly adolescence, *J. Am. Acad. Child Adolesc. Psychiatry,* 34:1322–1330, 1998.

Schachar, Sandberg, Rutter, "Agreement between teacher ratings and observations of hyperactivity, inattentiveness, and defiance," *J. Abnorm. Child Psychology,* 14(2):331–345, 1986.

Schiavi, Theilgaard, Owne, White, Sex chromosome anomalies, hormones, and aggressivity, *Arch. Gen. Psychiatry,* 41:93–99, 1984.

Schneider and Shiffrin, "Controlled and automatic human information processing. I. Detection, search, and attention," *Psychology Review,* 84:1–66, 1977.

Schoepfer, Whiting, Esch, Blacher, Shimasaki, Lindstrom, "cDNA clones coding for the structural subunit of a chicken brain nicotinic acetylcholine receptor," *Neuron,* 1:241–248, 1988.

Schooler, Zahn, Murphy, Buchsbaum, "Psychological correlates of monoamine oxidase activity in normals," *J. Nerv. Ment. Dis.,* 166:177–186, 1978.

Schroth, Chou, Ho, Mapping Z-DNA in the human genome, *J. Biol. Chem.,* 267:11846–11855, 1992.

Schwartz and Mertz, "Chromium (1H) and the glucose tolerance factor," *Arch. Biochem. Biophys.,* 85:292–295, 1959.

Schwartz et al., *J. Pharm. Pharmol.* 24:900–906, 1992.

Schwartz, et al., *Adv Biochem Psychopharmacol.,* 22:219–235, 1980.

Schwartz, et al., *Fourth World Congress on Biological Psychiatry,* 418(600)2, 1985.

Schwartz, et al., "Modulation of Receptor Mechanisms in the CNS:Hyper and Hyposensitivity to Catecholamines," *Neuropharmacology,* 17:665–685, 1978.

Scourfield et al., "Substance abuse, comorbidity, and sensation seeking: gender differences," *Comp. Psychiatry,* 37:384392, 1996.

See et al., *Nature,* 258:577–580, 1975

Seiden and Sabol, "Neurotoxicity of methamphetamine-related drug and cocaine," *Handbook of Neurotoxicology,* Marcel Dekker, Publishers, New York, 1995.

Self et al., "Opposite modulation of cocaine seeking behavior by $D_1$ and $D_2$-like dopamine receptor agonists," *Science,* 271:1586–1589, 1996.

Shaikh, Brutus, Siegel, Siegel, Regulation of feline aggression by the bed nucleus of stria terminalis, *Brain Res. Bull.,* 16:179–182, 1986.

Sharma, "Effects of nonpharmacological intervention on insulin sensitivity," *J. Cardiovasc. Pharmacol.,* 20 Suppl, 11:S27–34, 1992.

Shawitz et al., "Paradoxical response to amphetamine in developing rats treated with 6-hydroxydopamine," *Nature,* 261:153–155, 1976.

Shawitz et al., "Selective brain dopamine depletion indeveloping rats: An experimental model of minimal brain dysfunction," *Science,* 191:305–307, 1976.

Shaywitz et al., "CSF monamine metabolites in children with minimal brain dysfuntion: Evidence for alteration of brain dopamine," *J. Pediatrics,* 90:67–71, 1977.

Shekim et al., "Urinary MHPG and HVA excretion in boys with attention deficit hyperactivity disorder and hyperactivity treated D-amphetamine," *Biol. Psychiatry,* 18:707–714, 1983.

Shekim, Bylund, Frankel, Alexson, Jones, Blue, Kirby, Corchoran, "Platelet MAO activity and personality variations in normals," *Psychiatry Res.,* 27:81–88, 1989.

Shekim, Dekirmenjian, Chapel, "Urinary MHPG excretion in minimal brain dsyfunction and its modification by d-amphetamine," *Am. J. Psychiatry,* 136:667–671, 1997.

Shekim, Javaid, Davis, Bylund, "Urinary MHPG and HVA excretion in boys with attention deficit hyperactivity disorder and hyperactivity treated with d-amphetamine," *Biol. Psychiatry,* 18:707–714, 1983.

Sherif, Marcusson, Oreland, "Brain gamma-aminobutyrate transaminanse and monoamine oxidase activities in suicide victims," *Eur. Arch. Psychiatry Clin. Neurosci.*, 241:139–144, 1991.

Sherman, Iacono, McGue, "Attention-deficit hyperactivity disorder dimensions: A twin study of inattention and impulsivity-hyperactivity," *J. Am. Acad. Child. Adolesc. Psychiatry.*, 36:745–753, 1997.

Sherman, McGue, Iacono, "Twin concordance for attention deficit hyperactivity disorder: A comparison of teachers', and mothers' reports," *Am. J. Psychiatry*, 154:532–535, 1997.

Sholl, Goy, Kim, Aromatase, 5-alpha-reductase, and androgen receptor levels in the fetal monkey brain during fetal development, *Endocrinology*, 124:627–634, 1989.

Shulman, "Intelligence and delinquency," *J. Criminal Law and Criminol.*, 41:763–781, 1951.

Sikich, and Todd, Are the neuordevelopmental effects of gonadal hormones related to sex differences in psychiatric illness, *Psychiair. Dev,* 4:277–309, 1988.

Silverstein, Smith, Johnston, "Effect of clonidine on platelet alpha 2-adrenoreceptors and plasma norepinephrine of children with Tourette syndrome," Dev. Med. Child Neurol, 27:793–799, 1985.

Simon, Vaughan, Ritter, "The scalp topography of potentials in auditory and visual discrimination tasks," *Electroencephalography and Clinical Neurophysiology,* 42:528–535, 1977.

Skekim, Davis, Bylund, Brunngraber, Fikes, Lanham, "Platelet MAO in children with attention deficit disorder and hyperactivity: a pilot study," *Am. J. Psychiaty,* 139:936–938, 1982.

Skolnick, "Old Chinese herbal medicine used for fever yields possible new Alzheimer disease therapy," *JAMA,* 277(10):776, 1997.

Sleator and Ullmann, *Clinical Pediatrics,* 1981.

Sleddens, Oostra Brinkman, Trapman, Trinucleotide repeat polymorphism in the androgen receptor (AR) gene, *Nucleic Acids Res.,* 20:1427, 1992.

Sleddens, Oostra, Brinkman, Trapman, Trinucleotide (GGN) repeat polymorphism in the human androgen receptor (AR) gene, *Hum. Molec. Genet.,* 2:493, 1993.

Smith, Stapleton, Moreno, Halgren, "The effects of anterior temporal lobectomy on endogenous EPs recorded during verbal recognition memory testing," *Society for Neuroscience, Abs.,* 11:527, 1985.

Smith, O'Hara, Persico et al., "Genetic vulnerability to drug abuse; the $D_2$ dopamine receptor TaqI $B_1$ restriction fragment length polymorphism appears more frequently in polysubstance abusers," *Arch. Gen. Psych.,* 49(9):723–727, 1992.

Smythe et al., "The extrinsic modulation of hippocampal synchrony (theta) depends on the coactivation of cholinergic and Gaba-ergic medial septal inputs," *Neurosci. BioBehav. Rev.,* 16:289–308, 1992.

Sobell, Heston, Sommer, "Delineation of genetic predisposition to multifactorial disease: a general approach on the threshold of feasibility," *Genomics,* 12:1–6, 1991.

Sostek, Buchsbaum, Rapoport, "Effects of amphetamine on vigilance performance in normal and hyperactive children," *Journal of Abnormal Child Psychology,* 8:491–500, 1980.

Spandidos and Holmes, "Transcriptional enhancer activity in the variable tandem repeat DNA sequence downstream of the human Ha-ras-1 gene," *FEBS Lett,* 218:41–46, 1987.

Spielman et al., "Transmission test for linkage disequilibrium: the insulin gene region and insulin-dependent diabetus mellitus," *Am. J. Hum. Genet.,* 52:506–516, 1993.

Stanzione, Fattapposta, Tagliati, D'Alessio, Marciani, Foti, Amabile, "Dopamergic pharmacological manipulations in normal humans confirm the specificity of the visual (PERG-VEP): and cognitive (P300) electrophysiological alternations in Parkinson's Disease," *Electroencephalography and Clinical Neurophysiology,* 44:447–448, 1990.

Starke, Montel, Gayk, Marker, "Comparison of the effects of clonidine on pre-and postsynaptic adrenoceptors in the rabbit pulmonary artery," *Naunyn-Schmiedeberg. Arch. Pharmacol.,* 285:133–150, 1974.

Stefanick, "Exercise and weight control," *In: Exercise and Sport Sciences Reviews,* Volume 21, J.O. Holloszy, (ed)., Baltimore, Md., Williams and Wilkins, 1993.

Steinlein, Anokhin, Mao, Schalt, Vogel, "Localization of a gene for the human low voltage EEG on 20q and genetic heterogenity," *Genomics,* 12:69–73, 1992.

Steinlein, Smigrodzki, Lindstrom, Anand, Köhler, Tocharentanaphol, Vogel, "Refinement of the localization of the gene for neuronal nicotinic acetylcholine receptor a4 subunit (CHRNA4) to human chromosome 20q13.2-a13.3," *Genomics,* 22:493495, 1994.

Steinlein, "Detection of a CfoI polymorphism within exon 5 of the human neuronal nicotinic acetylcholine receptor alpha 4 subunit gene (CHRNA4)," *Hum. Genet.,* 96:130, 1995.

Steinlein, Mulley, Propping, Wallace, Phillips, Sutherland, Scheffer, Berkovic, "A missense mutation in the neuronal nicotinic acetylcholine receptor a4 subunit is associated with autosomal dominant noctural frontal lobe epilepsy," *Nature Genet.,* 11:201–203, 1995.

Steinlein, Weiland, Stoodt, Propping, "Exon-intron structure of the human neuronal nicotinic acetylcholine receptor a4 subunit (CHRNA4)," *Genomics.,* 32:289–294, 1996.

Steinlein, Deckert, Nöthen, Franke, Maier, Beckman, Propping, "Neuronal nicotinic acetylcholine receptor a4 subunit (CHRNA4) and panic disorder An association study," *Am. J. Med. Gen.* (Neuropsych. Genet), 74:199–201, 1997a Steinlein, Magnusson, Stoodt, Bertrand, Weiland, Berkovic, Nakken, Propping, Bertrand, "An insertion mutation of the CHRNA4 gene in a family with autosomal dominant noctural frontal lobe epilepsy," *Hum. Molec. Genet.,* 6:943–947, 1997b.

Stevenson, Pennington, Gilger, DeFries, Gillis, "Hyperactivity and spelling disability: Testing for shared genetic etiology," *J. Child. Psychol. Psychiatry,* 34:1137–1152, 1993.

Stewart, Comings, Singer, Deblois, The overlap between hyperactive and unsocialized aggressive children, *J. Child Psychol Psychiatry,* 22:3545, 1981.

Stewart, Deblois, Comings, Psychiatric disorders in the parents of hypemctive boys and those with conduct disorder, J. Child Psychol. Psychiatry, 21:283–292, 1980.

Strandburg et al., "Continuous-processing-related event-related potentials in children with Attention-Deficit Hyperactivity Disorder," *Biol. Psychiatry,* 40:964–980, 1996.

Struve and Straumanis, "Separation of chronic marijuana (THC) users from nonusers: a discriminate function analysis using quantitative electroencephalographic variables," *Biol. Psychiatry,* 271:52A–53A, 1990.

Suarez, Parsian, Hampe et at, "Linkage disequilibria at the $D_2$ dopamine receptor locus ($DRD_2$) in alcoholics and controls", *Genomics,* 19:12–20, 1994.

Summar, The use of linkage analysis and the Centre d'Etude Polymorphisme Humain (CEPH) panel of DNA in the study of the arginine vasopressin, oxygtocin and prodynorphin gene loci, *Prog. Brain Res.,* 93:309–317, 1992.

Sutton, Braren, Zubin, John, "Evoked potential correlates of stimulus uncertainty," Science, 150:1961–1969, 1965.

Tabakoff, Hoffman, Lee, Saito, Willard, Leon-Jones, "Differences in platelet enzyme activity between alcoholics and nonalcoholics," New Eng. J. Med., 318:134–139, 1988.

Tajima, et al., Chem. Pharm. Bull., 28:1935, 1980.

Takagi, et at., Eur. J. Pharm., 55:109, 1979.

Tang, Han, Chen, et al., "Effects of Huperzine A on learning and the retrieval process of discrimination performance in rat," Chung Kuo Yao Li Hsueh Pao, 7:507–511 (article in Chinese), 1986.

Tang, De Sarno, Sugaya, et al., "Effect of Huperzine A, a new cholinesterase inhibitor, on the central cholinergic system of the rat" J. Neurosci. Res., 24:276–285, 1989.

Tang, Kindel, Kozikowski, Hanin, "Comparison of the effects of natural and synthetic huperzine-A on rat brain cholinergic function in vitro and in vivo.," J. Ethnopharmacol., 44(3):147–155, 1994a.

Tang, Xu., Feng, et al., "Effect of cholinesterase inhibition in vitro by Huperzine analogs," Chung Kuo Yao Li Hsueh, 15:107–110, 1994b.

Tang, Fu, Kötter, Cotter, Cantor, Köster, "Matrix-assisted laser desportion/ionization mass spectrometry of immobilized duplex DNA probes," Nucleic Acids Res., 23:3126–3131, 1995.

Thawki, et al., J. Veurochem., 41:611–617, 1983.

Thelu, Zarski, Froissart, Rachail, Seigneurin, "c-Ha-ras polymorphism in patients with hepatocellular carcinoma," Gastroenterol. Clin. Biol., 17:903–907, 1993.

Tivol, Shalish, Schuback, Hus, Breakefield, "Mutational analysis of the human MAOA gene," Am. J. Med. Gen. (Neuropsych. Genet.), 67:92–97, 1996.

Tobiessen and Karowe, 1969.

Trachtenberg and Blum, "Improvement of cocaine-induced neuromodulator deficits by neuronutrient tropamine," J. Psychoactive Drugs, 20:315–331, 1988.

Trepicchio and Krontiris, "Members of the rel/NF-KB family of transcriptional regulatory factors bind the HRAS 1 minisatellite DNA sequence," Nucl. Acids Res., 21:977–985, 1992.

Trepicchio and Krontiris, "IGH minisatellite suppression of USF-binding-site-and E$\mu$-mediated transcriptional activation of the adenovirus major late promoter," Nucl. Acids Res., 21:977–985, 1993.

Ueda, et al., Biochem. Biophys. Res. Commun., 137:897–902, 1986.

Uhl et al., "Substance abuse vulnerability at $D_2$ receptor genes," Trends Neurosci., 16:83–88, 1993.

Unwin, "Nicotmic acetylcholine receptor channel imaged in the open state," Nature, 373:3743, 1993.

Uusitupa, Mykkanen, Sitonen, Laakso, Sarlund, Kolehmainen, Rasanen, Kumpulainen, Pyorala, "Chromium supplementation in impaired glucose tolerance of the elderly: effects on blood glucose, plasma insulin, C-peptide and lipid levels," Br. J. Nutr., 68:209–216, 1992.

V. Petkov, 1981.

Vafiadis, Bennett, Todd, Nadeau, Grabs, Goodyer, Wickramasinghe, Colle, Polychronakos, "Insulin expression in human thymus is modulated by INS VNTR alleles at the IDDM2 locus," Nature Genet., 15:289–292, 1997.

Valzelli, Psychobiology of Aggression and Violence, New York: Raven Press, 1981.

van Praag, Serotonergic dysfunction and aggression control, Psychol. Med., 21:15–19, 1991.

Van Tol et al., "Multiple dopamine $D_4$ receptor variants in human population," Nature 358:149–152, 1992.

Vanyukov, Moss, Plail, Blackson, Mezzich, Tarter, "Antisocial symptoms in preadolescent boys and in their parents: associations with cortisol," Psychiatr. Res., 46:9–17, 1993.

Vasile, Duffy, McAnulty, Mooney, Bloomingdale, Schildkaut, "Abnormal flash visual evoked responses in melancholia: a replication study," Biological Psychiatry, 24:325–336 1992.

Vaughan and Arezzo, "The neural basis of event-related potentials. In T. W. Picton (Ed.), Human Event-Related Potentials, EEG Handbook, 3:45–96, 1988.

Ved, Koenig, Dave, et al., "Huperzine-A, a potential therapeutic agent for dementia, reduces neuronal cell death caused by glutamate," Neuroreport, 8:963–968, 1997.

Volkow et al., "Effects of methylphenedate on regional brain glucoes metabolism in humans: relationship to dopamine $D_2$ receptors," Am. J. Psychiatry, 154:50–55, 1996.

Volkow et al., "Is methylphenidate like cocaine? Studies on their pharmacoketics and distribution in human brain," Arch. Gen. Psychiatry, 52:456–463, 1995.

Vonknorring, Hallmann, Vonknorring, Oreland, "Platelet monoamine oxidase activity in type-1 and type-2 alcoholism," Alcohol Alcohol, 28:409–416, 1991.

Vonknorring, Oreland, Winblad, "Personality traits treated to monoamine oxidase activity in platelets," Psychiatry Res., 12:11–26, 1984.

Wada, Wada, Boulter, Deneris, Heinemann, Patrick, Swanson, "Distribution of alpha2, alpha3, alpha4, and beta2 neuronal nicotmic receptor subunit mRNAs in the central nervous system: A hybridization histochemical study in the rat," J. Comp. Neurol., 284:314–335, 1989.

Wahls, Swenson, Moore, "Two hypervariable minisatellite DNA binding proteins," Nucl. Acids Res., 19:3269–3274, 1991.

Waldmaqn, Rowe, Abramowitz, Kozel, Mohr, Sherman, Cleveland, Sanders, Stevens, "Association of the dopamine transporter gene (DAT 1) and attention deficit hyperactivity disorder," Am. J. Hum. Genet., 59:A25, 1996.

Wallberg-Henriksson, "Exercise and diabetes mellitus," In: Exercise and Sport Science Reviews, Volume 20, J. Q. Holloszy, (ed)., Baltimore, Md., Williams and Wilkins, 1992.

Wang, Amirhaeri, Kang, Wells, Griffith, "Preferential nucleosome assembly at DNA triplet repeats from the myotonic dystrophy gene," Science, 265:669–671, 1994.

Wang, Quigley, Kolpak, Crawford, van Boom, van der Marcl, Rich, "Molecular structure of a left-handed double helical DNA fragment at atomic resolution," Nature, 282:686–682, 1979.

Wang, Yue, Tang, "Anti-cholinesterase activity of Huperzine A," Chung Kuo Yao Li Hsueh Pao, 7:110–113 (article in Chinese), 1986.

Wang, Feng, Lu, et al., "Pharmacokinetics of Huperzine A in rates and mice," Chung Kuo Yao Li Hsueh Pao, 9:193–196 (article in Chinese), 1988.

Warburton, "Nicotine as a cognitive enhancer," Prog. Neuropsychopharmacol. Biol. Psychiatry, 16:181–191, 1992.

Weeks and Lange, "The affected-pedigree-member method: power to detect linkage," Am. J. Hum. Genet., 42:315–326, 1988.

Weeks and Lathrop, "Polygenic disease: methods for mapping complex disease traits," Trends Genet., 11:513–519, 1995.

Wei, Ramchand, Hemmings, "Possible control of dopemine O-hydroxylase via a codominant mechanism associated with polymorphic (GT)$_n$ repeat at this gene locus in healthy individuals," *Hum. Genet.,* 99:52–55, 1997.

Weiland and Steinlein, "Dincucleotide polymorphism in the first intron of the human neuronal nicotinic acetylcholine receptor a4 subunit gene (CHRNA4)," *Clin. Genetics,* 50:433434, 1996.

Weinberger et al., "Mescocortical dopaminergic function and human cognition," *Annals New York Acad. Sci.,* 537:330–338, 1988.

Weiner et al., "A controlled study of siblings of hyperactive children," *J. Nerv. Ment. Dis.,* 165:110–117, 1977.

Weintramb et al., "Long term weight control study (weeks 0 to 34)," *Clin. Pharmacol. Ther.,* 51:586–594, 1992.

Wells, "Molecular basis of genetic instability of triplet repeats," *J. Biol. Chem.,* 271:2875–2878, 1996.

Wesnes and Warburton, "Smoking, nicotine and human performance," *In: Nicotine and the Tobacco Smoking Habit, Sectin 114. The International Encyclopedia ofpharmacology and Therapeutics,* D. J. K. Balfour (Ed.), New York, Pergamon Press, pp. 133–152, 1984.

West, "Epidemiology of Diabetes and it's Vascular Lesions," New York, N.Y.: Elsevier, 1978.

Weyler, Hsu, Breakefield, "Biochemistry and genetics of monamine oxidase," *J. Pharmacol. Ther.,* 47:391417, 1990.

Whipple, Parker, Noble, "An atypical neurocognitive profile in alcoholic fathers and their sons," *Journal of Studies on Alcohol,* 49:240244, 1988.

White, "A triple dissociation of memory systems: hippocampus, amygdala, and dorsal striaturn," *Behavorial Neuroscience,* 107:3–22, 1993.

Whiting and Lindstrom, "Characterization of bovine and human nicotinic acetylcholine receptors using monoclonal antibodies," *J. Neurosci.,* 8:3395–3404, 1988.

Whiting, Schoepfer, Conroy, Gore, Keyser, Shimasaki, Esch, Lindstrom, "Expression of nicotinic acetylcholine receptor subtypes in brain and retina," *Mol. Brain Res.,* 10:61–70, 1991.

Wiberg, Gottfries, Oreland, "Low platelet monoamine oxidase activity in human alcoholics," *Med. Biol.,* 55:181–186, 1977.

Wilkins, Shallice, McCarthy, "Frontal lesions and sustained attention," *Neuropsychologia,* 25:359–365, 1987.

Williams et al., *Nature,* 376:572–675, 1995.

Williams, et al., "The structured clinical interview for DSM-III-R(SCID). II. Multisite Test-retest reliability," *Arch. Gen. Psychiatry,* 49:630636, 1992.

Williams, "Alcoholism: The Nutritional Approach," Austin: University of Texas Press, 1959.

Wills, In: *The Runaway Brain,* Basic Books, New York, N.Y., pp 1–358, 1993.

Wilson and Gondy, "Effects of chromium supplementation on fasting insulin and lipid parameters in healthy, nonoverweight young subjects," *Diabetes Res. Clin. Prac.,* 28:179–184, 1995.

Wise and Bozarth, "Action of abused drugs on reward systems in the brain, "In Blum and Manzo (Eds.), Neurotoxicology (pp. 111–133), New York: Marcel Dekker, 1985.

Wisler et al, 1981.

Wittig, Wölffl, Dorbic, Vahrson, Rich, "Transcription of human c-myc in permeabilized nuclei is associated with formation of Z-DNA in three discrete regions of the gene," *EMBO J,* 12:4653–4663, 1992.

Wolff, Plaetke, Jeffreys, White, "Unequal crossingover between homologous chromosomes is not the maior mechanism involved in the generation of new alleles at VNIR loci," *Genomics,* 5:382–384, 1989.

Wolff, Martinez, Rich, Majzoub, "Transcription of the human corticotropin-releasing hormone gene in NPLC cells is correlated with Z-DNA formation," *Proc. Natl. Acad. Sci. USA,* 93:3664–3668, 1996.

Wood, Allison, Goff, Williamson, Spencer, "On the origin of P30–0 in man," *In Kornhuber and Deecke* (Eds.), *Motivation, Motor and Sensory Processes of the Brain: Electrical Potentials, Behavior and Clinical Use. Progress in Brain Research.* Vol. 54), New York: Elsevier, 1980.

Wragg et al., *The Lancet,* 347:509–512, 1996.

Wright, "Mutation at VNTRS: are minisatellites the evolutionary progeny of microsatellites," *Genome,* 37:345–346, 1994.

Wu, Ikezono, Angus, Shelhamer, "Characterization of the promoter for the human 85 kDA cytosolic phospholipase A$_2$ gene," *Nucl. Acids Res.,* 22:5093–5098, 1994.

Wu, Muhleman, Comings, PCR amplification of the TaqI B1/B2 polymorphism at intron 5 of the dopamine b-hydroxylase gene," *Psychiat. Genet.,* 7:3940, 1997.

Wurtman and Fernstrom, "Control of brain neurotransmitter synthesis by precursor availability and nutritional state," *Biochemical Pharmacology,* 25, 1691–1696 1976.

Wurtman, Hefti, and Melamed, "Precursor control of neurotransmitter synthesis," *Pharmacological Review,* 32:315–335, 1981.

Wurtman, "Nutrients that modify brain function," *Sci. Am.,* 246:50–59, 1982.

Wurtman, "Food consumption, neurotransmitter synthesis, and human behavior," *Experientia,* 44:356–369, 1983.

Wurtman and Ritter-Walker, "Dietary Phenylalanine and Brain Function," *Boston: Birkhauser,* 1988.

Wyatt, Potkin, Murphy, "Platelet monamine oxidase activity in schizophrenia: a review of the data," *Am. J. Psychiatry,* 136:377–385, 1979.

Xiong and Tang, "Effect of Huperzine A, a novel acetylcholinesterase inhibitor, on radial maze performance in rates," *Pharmacol. Biochem. Behav.,* 51:415419, 1995.

Xiong, Tang, Lin, et al., "Effects of isovaniHuperzine A on cholinesterase and scioikanube-induced memory impairment," *Chung Kuo Yao Li Hsueh Pao,* 16:21–25 (in Chinese), 1995.

Xu, Gao, Weng, Du, Xu, Yang, Zhang, Tong, Fang, Chai et al., "Efficacy of tablet huperzine-A on memory, cognition, and behavior in Alzheimer's disease," *Chung Kuo Yao Li Hsueh Pao,* 16(5):391–395, 1995.

Yamazaki, Nomoto, Mishima, Kominami, "A 35-kDA protein binding to a cytosine-rich strand of hypervariable minisatellite DNA," *J. Biol. Chem.,* 267:12311–12316, 1992.

Yan, Lu, Lou, et al., "Effects of Huperzine A and B on skeletal muscle and the electoenephalogram," *Chung Kuo Yao Li Hsueh Pao,* 8:117–123, 1987.

Yaspelkis, Patterson, Anderla, Ding, Ivy, "Carbohydrate supplementation spares muscle glycogen during variable intensity exercise", *J. Appl. Physiol.,* 75:1477–1485, 1993.

Yoshida et al., "Molecular abnormality of an interactive aldehyde dehydrogenase variant commonly found in Orientals," *Proc. Natl. Acad. Sci. USA,* 81:258–261, 1984.

Yu-cum and Yu-feng, "Urinary 3-methoxy-4 hydroxyphenylglycol sulfate excretion in seventy-three schoolchildren with minimal brain dysfunction syndrome," *Biol. Psychiatry,* 19:861–868, 1984.

Zametkin, Karoum, Linnoila, Rapoport, Brown, Chuang, Wyatt, "Stimulants, urinary catecholamines, and indoleamines in hyperactivity. A comparison of methylphenidate and dextroamphetamine," *Arch. Gen. Psychiatry,* 42:251–255, 1985.

Zametkin et al., "Cerebral glucose metabolism in adults with hyperactivity of childhood onset," N. Engl. *J. Med.,* 323:1361–1366, 1990a.

Zametkin, Nordahl, Gross, King, Sample, Rumsey, Hamburger, Cohen, "Cerebral glucose metabolism in adults with hyperactivity of childhood onset," *N. Engl. J. Med.,* 323:1361–1366, 1990b.

Zhang, Wang, Zheng, et al., "Facilitation of cholinergic transmission by Huperzine A in; toad paravertebral ganglia in vitro," *Chung Kuo Yao Li Hsueh Pao,* 15:158–161 (article in Chinese), 1994.

Zhang, Tang, Han, et al., "Drug evaluation of Huperzine A in the treatment of senile memory disorders," *Chung Kuo Yao Li Hsueh Pao,* 12:250–252 (article in Chinese), 1991.

Zhi, Yi, XI, "Huperzine A ameliorates the spatial working memory impairments induced by AF64A," *Neuroreport,* 6(16):2221–2224, 1995.

Zhu and Giacobini, "Second generation choliesterase inhibitors: effect of (L)-Huperzine-A on cortical biogenic amines," *J. Neurosci. Res.,* 41:828–835, 1995.

Zhu and Tang, "Facilitatory effects of Huperzine A and B on learning and memory of spatial discrimination in mice," *Yao Hsueh Hsueh Pao,* 22:812–817 (article in Chinese), 1987.

Zhu and Tang, "Improvement of impaired memory in mice by Huperizine A and Huperzine B," *Chung Kuo Yao Li Hsueh Pao,* 9:492497 (article in Chinese), 1988.

Zhu, "Development of natural products as drugs acting on central nervous system," *Mem. Inst. Oswaldo Cruz,* 86:173–175, 1991.

Zola-Morgan, Squire, Alvarez-Royo, Clower, "Independence of memory functions and emotional behavior: separate contributions of the hippocampal formation and the amygdala," Hippocampus, 1,207–220, 1991.

What is claimed is:

1. A kit comprising a buccal swab suitable to obtain a subject's DNA sample for allelic analysis; and a composition for the treatment of RDS behaviors in a subject, the composition comprising:
  a) an opiate destruction-inhibiting amount of at least one substance which inhibits the enzymatic destruction of a neuropeptidyl opiate, said substance being selected from the group consisting of amino acids, peptides, and structural analogues or derivatives thereof;
  b) a neurotransmitter synthesis-promoting amount of at least one neurotransmitter precursor selected from the group consisting of dopamine precursors L-Tyr, L-Phe and L-dopa, serotonin precursors L-Trp and 5-hydroxytryptophan, and gamma amino butyric acid (GABA) precursors L-glutamine, L-glutamic acid, and L-glutamate; and
  c) a tryptophan concentration enhancing amount of chromium picolinate or chromium nicotinate, the amount of said substance and said neurotransmitter precursor and said chromium compound being effective in reducing the subject's RDS behaviors; and
  d) a neurotransmitter synthesis-promoting amount of at least one neurotransmitter synthesis promoting substance selected from the group consisting of Rhodiola and huberzine, wherein the amount of said substance and said neurotransmitter precursor and said chromium compound being chosen so that the composition is effective in reducing the Attention Deficits disorder, attentional processing, or memory.

2. A kit comprising a buccal swab suitable to obtain a subjects DNA sample for alleles analysis; and a composition for the prevention or treatment of unwanted weight gain comprising:
  a) an opiate destruction-inhibiting amount of at least one substance which inhibits the enzymatic destruction of a neuropeptidyl opiate, said substance being selected from the group consisting of amino acids, peptides, and structural analogues or derivatives thereof;
  b) a neurotransmitter synthesis-promoting amount of at least one neurotransmitter precursor selected from the group consisting of dopamine precursors L-Tyr, L-Phe and L-dopa, serotonin precursors L-Trp and 5-hydroxytryptophan, and gamma amino butyric acid (GABA) precursors L-glutamine, L-glutamic acid, and L-glutamate; and
  c) a tryptophan concentration enhancing amount of chromium picolinate or chromium nicotinate, the amount of said substance and said neurotransmitter precursor and said chromium compound being effective in reducing the subject's unwanted weight.

3. A kit comprising a buccal swab suitable to obtain a subjects DNA sample for allele analysis; and composition for the treatment of Attention Deficits disorder comprising:
  a) an opiate destruction-inhibiting amount of at least one substance which inhibits the enzymatic destruction of a neuropeptidyl opiate, said substance being selected from the group consisting of amino acids, peptides, and analogues or derivatives of amino acids or peptides;
  b) a neurotransmitter synthesis-promoting amount of at least one neurotransmitter precursor selected from the group consisting of dopamine precursors L-Tyr, L-Phe and L-DOPA, serotonin precursors L-Trp and 5-hydroxytryptophan, and gamma amino butyric acid (GABA) precursors L-glutamine, L-glutamic acid, and L-glutamate; and
  c) a tryptophan concentration enhancing amount of chromium salt; and
  d) a neurotransmitter synthesis-promoting amount of at least one neurotransmitter synthesis promoting substance selected from the group consisting of Rhodiola or huberzine the amount of said substance and said neurotransmitter precursor and said neurotransmitter synthesis-promoting substance being chosen so that the composition is effective in reducing the Attention Deficits disorder, attentional processing, or memory.

4. A kit comprising a buccal swab suitable to obtain a subjects DNA sample for allele analysis; and a composition for treating a subject with RDS behavior selected from the group consisting of SUD, Obesity, Smoking, Tourettes Syndrome, ADHD, Schizoid/Avoidant Behavior, Aggression, Posttraumatic stress syndrome, PMS or tobacco use, the composition comprising:
  a) an opiate destruction-inhibiting amount of at least one substance which inhibits the enzymatic destruction of a neuropeptidyl opiate, said substance being selected from the group consisting of amino acids, peptides, and structural analogues or derivatives thereof;
  b) a neurotransmitter synthesis-promoting amount of at least one neurotransmitter precursor selected from the group consisting of the dopamine precursors L-Tyr, L-Phe and L-dopa, the serotonin precursors L-Trp and 5-hydroxytryptophan, and the gamma amino butyric acid (GABA) precursors L-glutamine, L-glutamic acid, and L-glutamate; and
  c) a tryptophan concentration enhancing amount of chromium picolinate or chromium nicotinate.

5. The kit of claim 4, wherein said RDS behavior is Obesity.

6. The kit of claim 4, wherein said composition comprises a daily dietary consumption of about 460 mg DL-phenylalanine, 25 mg L-tryptophan, 25 mg L-glutamine, and the mixture further comprises 5 mg pyridoxal-5'-phosphate.

7. The kit of claim 4, wherein the subject has a family history of chemical dependency, wherein said family history confirms an improved likelihood for successful treatment.

8. The kit of claim 4, wherein said composition inhibits binge eating.

9. The kit of claim 4, wherein said composition inhibits craving.

10. The kit of claim 1, wherein at least one of the following alleles: $D_2$TaqI A1, B1, C1 or exon 6–7 haplotype HTR2A—C allele homozygous OB—homozygosity for <208 BP alleles of 1875 dinucleotide repeat polymorphism human chromosome 2 microsatellite polymorphism, APO-D—TaqI 2.2 or 2.7 BP, or OB gene D7S 1875 alleles is detected in DNA from the buccal swab.

11. The kit of claim 1, wherein said composition comprises an effective amount of a chromium salt, and wherein the presence in the subject of the DRD2 A1 allele indicates an improved likelihood of positive response to the composition.

12. The kit of claim 1, wherein said composition comprises an effective amount of chromium picolinate, and wherein the presence of a DRD2 A2 allele in the subject indicates an improved likelihood of positive response to the composition.

13. The kit of claim 1, wherein the presence in the subject of at least one of the following alleles: D1 (homozygosity of Dde A1), D2(TaqI A1) D4 (VNTR2), D5 (dimucleotide 13 alleles range 135–159 BP), DAT1 VNTR (10/10), DBH (TaqIB1allele) indicates an improved likelihood for a successful response to the composition.

14. The kit of claim 1, wherein said RDS behavior further includes Autism, Tourette's Syndrome or ADHD, and wherein said subject has at least one of the following alleles: D (homozygosity of Dde A), D(Taq), D (VNTR) D (dinucleotide allele range—BP) DAT VNTR (/) DBH (TaqB allele), MAOA(X), and the presence of at least one allele indicates an improved likelihood for a successful response to the composition.

15. The kit of claim 1, wherein said composition further comprises an effective amount of Rhodiola or huberzine.

16. The kit of claim 1, wherein said RDS behavior is Pathological gambling and wherein the presence in a subject of at least one of the following alleles: D (homozygosity of Dde A), D (Taq A, B, C), indicates an improved likelihood for a successful response.

17. The kit of claim 1, wherein said RDS behavior further comprises pathological violence, Schizoid/Avoidant (SAB), Aggression, Anger, Hostility, or Posttraumatic Stress Disorders, wherein the presence in the subject of at least one of the following alleles D (Taq A, B, C, exon), DAT (VNTR/), mNOISa—homozygosity for <BP allele indicates an improved likelihood for a successful response.

18. The kit of claim 1, wherein said RDS behavior is PMS, wherein the presence of at least one of the following alleles DAT1 VNTR (10/10) $D_2$TaqI A1, B1, C1 exon $^{6-7}$ haplotype, or alleles from the DRD1, DRD2, DRD4, HTT, HTRIA, TD02, DBH, MAO, COMT, GABRAB, GABRB3, PENk, ADRA2A or ADRA2C genes indicates an improved likelihood for a successful response.

19. The kit of claim 1, wherein said RDS behavior further comprises substance abuse disorder.

20. The kit of claim 1, wherein said RDS behavior is substance use disorder.

21. The kit of claim 1, where the allele detected is for at least one RDS behavior, and the allele is at least from one of DRD1, DRD2, DRD3, DRD4, DRD5, DAT1, HTT, HTRIA, TD02, DBH, ADRA2A, ADRA2C, NET, MAOA, COMT, GABRA3, GABRB3, CNR1, CNRA4, NMDAR1, PENK, AR, CRF, HTRIDB, HTR2A, HTR2C, interferon-γ, CD8A or PSI genes.

22. The kit of claim 21, wherein said RDS behavior is selected from the group consisting of mania, OCD, sexual, sleep, grade school behavior, gambling, learning, inattention, ADHID, ADDR, impulsivity, MDE, CD, hyperactivity, phobia, schizoid behavior, general anxiety, somatization, drugs, IV drugs, read, ODD, tics, alcohol, or tobacco use.

23. The kit of claim 22, wherein said allele is a VNTR polymorphism of a MAOA gene.

24. The kit of claim 21, wherein said RDS behavior is schizoid or Avoidant.

25. The kit of claim 24, wherein said allele is selected from the group consisting of the $DRD_2$ gene $A_1$ allele, the $DAT_1$ gene, VNTR 10/10 allele, or the DβH gene $B_1$ allele.

26. The kit of claim 21, wherein said RDS behavior is Drug Use.

27. The kit of claim 26, wherein said allele is an increased number of $(AAT)_n$ triplet repeats in the CNR1 gene.

28. The kit of claim 21, wherein said RDS behavior is selected from the group consisting of obesity, anxiety, depression, psychoses, hostility, paranoid ideation, obsessive-compulsive, symptom total, general symptom index, novelty seeking, overall total, neuroticism and conscientiousness.

29. The kit of claim 1, wherein said allele is selected from the group comprising an increased number of the D7S 1873, D7S 1875, D7S514 or D7S680 dinucleotide repeats in the OB gene.

30. The kit of claim 29, wherein the number of said D7S1875 dinucleotide repeats is greater than 225 bp in length in both copies of the CNR1 gene.

31. The kit of claim 30, wherein said allele is the $D_2$A1 allele of the DRD2 gene.

32. The kit of claim 1, wherein said allelic analysis is for determining the existence of the $D_2$A1 allele of the DRD2 gene and an allele selected from the group comprising the an increased number of the D7S 1873, D7S 1875, D7S514 or D7S680 dinucleotide repeats in the OB gene.

33. The kit of claim 1, 2, or 3 defined further as including an RDS inventory scale.

* * * * *

UNITED STATES PATENT AND TRADEMARK OFFICE
CERTIFICATE OF CORRECTION

PATENT NO. : 6,955,873 B1 Page 1 of 1
DATED : October 18, 2005
INVENTOR(S) : Kenneth Blum It is certified that error appears in the above-identified patent and that said Letters Patent is hereby corrected as shown below:

Column 121,
Lines 15-21, should read:
10. The kit of claim 1, wherein at least one of the following alleles: D2Taql A1, B1, C1 or exon 6-7 haplotype HTR2A—C allele homozygous OB—homozygosity for <208 BP alleles of 1875 dinucleotide repeat polymorphism human chromosome 2 microsatellite polymorphism, APO-E—Taql 2.2 or 2.7 BP, or OB gene D7S 1875 alleles is detected in DNA from the buccal swab.

Signed and Sealed this

Thirty-first Day of January, 2006

JON W. DUDAS
*Director of the United States Patent and Trademark Office*